US009452156B2

(12) United States Patent
Kleinman et al.

(10) Patent No.: US 9,452,156 B2
(45) Date of Patent: *Sep. 27, 2016

(54) FORMULATIONS AND METHODS FOR VASCULAR PERMEABILITY-RELATED DISEASES OR CONDITIONS

(71) Applicant: Santen Pharmaceutical Co., Ltd., Osaka (JP)

(72) Inventors: David M. Kleinman, Rochester, NY (US); Thierry Nivaggioli, Atherton, CA (US); Mary E. Gerritsen, San Mateo, CA (US); David A. Weber, Danville, CA (US)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 428 days.

This patent is subject to a terminal disclaimer.

(21) Appl. No.: 13/874,405

(22) Filed: Apr. 30, 2013

(65) Prior Publication Data

US 2015/0265581 A1 Sep. 24, 2015

Related U.S. Application Data

(63) Continuation of application No. 13/530,025, filed on Jun. 21, 2012, now Pat. No. 8,486,960, which is a continuation of application No. 11/726,813, filed on Mar. 23, 2007, now Pat. No. 8,222,271.

(60) Provisional application No. 60/785,814, filed on Mar. 23, 2006.

(51) Int. Cl.
*A61K 31/436* (2006.01)
*A61K 47/10* (2006.01)

(52) U.S. Cl.
CPC ............. *A61K 31/436* (2013.01); *A61K 47/10* (2013.01)

(58) Field of Classification Search
CPC .................................................. A61K 31/436
See application file for complete search history.

(56) References Cited

U.S. PATENT DOCUMENTS

| | | |
|---|---|---|
| 3,416,530 A | 12/1968 | Ness |
| 3,630,200 A | 12/1971 | Higuchi |
| 3,828,777 A | 8/1974 | Ness |
| 3,914,402 A | 10/1975 | Shell |
| 3,926,188 A | 12/1975 | Baker et al. |
| 4,014,335 A | 3/1977 | Arnold |
| 4,093,709 A | 6/1978 | Choi et al. |
| 4,300,557 A | 11/1981 | Refojo et al. |
| 4,316,885 A | 2/1982 | Rakhit |
| 4,650,803 A | 3/1987 | Stella et al. |
| 4,853,224 A | 8/1989 | Wong |
| 4,946,450 A | 8/1990 | Erwin |
| 4,997,652 A | 3/1991 | Wong |
| 5,011,844 A | 4/1991 | Fehr |
| 5,023,262 A | 6/1991 | Caufield et al. |
| 5,078,999 A | 1/1992 | Warner et al. |
| 5,100,899 A | 3/1992 | Calne |
| 5,120,725 A | 6/1992 | Kao et al. |
| 5,120,727 A | 6/1992 | Kao et al. |
| 5,120,842 A | 6/1992 | Failli et al. |
| 5,147,647 A | 9/1992 | Darougar |
| 5,164,188 A | 11/1992 | Wong |
| 5,177,203 A | 1/1993 | Failli et al. |
| 5,178,635 A | 1/1993 | Gwon et al. |
| 5,189,042 A | 2/1993 | Goulet et al. |
| 5,192,773 A | 3/1993 | Armistead et al. |
| 5,192,802 A | 3/1993 | Rencher |
| 5,258,389 A | 11/1993 | Goulet et al. |
| 5,300,114 A | 4/1994 | Gwon et al. |
| 5,322,691 A | 6/1994 | Darougar et al. |
| 5,368,865 A | 11/1994 | Asakura et al. |
| 5,378,475 A | 1/1995 | Smith et al. |
| 5,387,589 A | 2/1995 | Kulkarni |
| 5,395,618 A | 3/1995 | Darougar et al. |
| 5,403,901 A | 4/1995 | Namdaran et al. |
| 5,443,505 A | 8/1995 | Wong et al. |
| 5,457,111 A | 10/1995 | Luly et al. |
| 5,466,233 A | 11/1995 | Weiner et al. |
| 5,514,686 A | 5/1996 | Mochizuki et al. |
| 5,516,522 A | 5/1996 | Peyman et al. |
| 5,516,770 A | 5/1996 | Waranis et al. |
| 5,516,781 A | 5/1996 | Morris et al. |
| 5,527,907 A | 6/1996 | Or et al. |
| 5,530,006 A | 6/1996 | Waranis et al. |
| 5,532,248 A | 7/1996 | Goulet et al. |
| 5,536,729 A | 7/1996 | Waranis et al. |
| 5,559,121 A | 9/1996 | Harrison et al. |
| 5,583,139 A | 12/1996 | Or et al. |
| 5,601,844 A | 2/1997 | Kagayama et al. |
| 5,614,547 A | 3/1997 | Hamilton et al. |

(Continued)

FOREIGN PATENT DOCUMENTS

| | | |
|---|---|---|
| CN | 1333018 A | 1/2002 |
| CN | 1340358 A | 3/2002 |

(Continued)

OTHER PUBLICATIONS

Thurau, S.R. Ophthalmologe, May 2005, vol. 102, No. 5, abstract.*
Correction for "Photodynamic Therapy of Subfoveal Choroidal Neovascularization in Age-Related Macular Degeneration with Verteporfin, One-Year Results of 2 Randomized Clinical Trials—TAP Report 1", Archives of Ophthalmology, Treatment of Age-Related Macular Degeneration with Photodynamic Therapy (TAP) Study Group, vol. 118, Apr. 2000, p. 488.

(Continued)

*Primary Examiner* — Samira Jean-Louis

(74) *Attorney, Agent, or Firm* — Morrison & Foerster LLP

(57) ABSTRACT

Described herein are formulations and methods for treating, inhibiting, preventing, delaying onset, or causing regression of a disease or condition relating to vascular permeability.

8 Claims, 4 Drawing Sheets

(56) References Cited

U.S. PATENT DOCUMENTS

| | | |
|---|---|---|
| 5,616,588 A | 4/1997 | Waranis et al. |
| 5,621,108 A | 4/1997 | Smith, III et al. |
| 5,632,984 A | 5/1997 | Wong et al. |
| 5,672,605 A | 9/1997 | Or et al. |
| 5,679,666 A | 10/1997 | Clark |
| 5,696,135 A | 12/1997 | Steiner et al. |
| 5,725,493 A | 3/1998 | Avery et al. |
| 5,743,274 A | 4/1998 | Peyman |
| 5,766,242 A | 6/1998 | Wong et al. |
| 5,766,619 A | 6/1998 | Aiache et al. |
| 5,770,592 A | 6/1998 | Clark |
| 5,773,019 A | 6/1998 | Ashton et al. |
| 5,773,021 A | 6/1998 | Gurtler et al. |
| 5,798,355 A | 8/1998 | Steiner et al. |
| 5,824,072 A | 10/1998 | Wong |
| 5,830,173 A | 11/1998 | Avery et al. |
| 5,883,082 A | 3/1999 | Bennett et al. |
| 5,902,598 A | 5/1999 | Chen et al. |
| 5,904,144 A | 5/1999 | Hammang et al. |
| 5,912,253 A | 6/1999 | Cottens et al. |
| 6,004,973 A | 12/1999 | Guitard et al. |
| 6,007,510 A | 12/1999 | Nigam |
| 6,015,815 A | 1/2000 | Mollison |
| 6,074,661 A | 6/2000 | Olejnik et al. |
| 6,110,485 A | 8/2000 | Olejnik et al. |
| 6,126,687 A | 10/2000 | Peyman |
| 6,142,969 A | 11/2000 | Nigam |
| 6,217,895 B1 | 4/2001 | Guo et al. |
| 6,239,102 B1 | 5/2001 | Tiemessen |
| 6,239,113 B1 | 5/2001 | Dawson et al. |
| 6,254,860 B1 | 7/2001 | Garst |
| 6,258,856 B1 | 7/2001 | Chamberlain et al. |
| 6,267,985 B1 | 7/2001 | Chen et al. |
| 6,306,422 B1 | 10/2001 | Batich et al. |
| 6,326,387 B1 | 12/2001 | Armistead |
| 6,329,386 B1 | 12/2001 | Mollison |
| 6,331,313 B1 | 12/2001 | Wong et al. |
| 6,350,442 B2 | 2/2002 | Garst |
| 6,361,760 B1 | 3/2002 | Murata et al. |
| 6,375,972 B1 | 4/2002 | Guo et al. |
| 6,376,517 B1 | 4/2002 | Ross et al. |
| 6,378,526 B1 | 4/2002 | Bowman et al. |
| 6,387,918 B1 | 5/2002 | Yamanaka et al. |
| 6,397,849 B1 | 6/2002 | Bowman et al. |
| 6,399,629 B1 | 6/2002 | Chamberland et al. |
| 6,413,245 B1 | 7/2002 | Yaacobi et al. |
| 6,413,540 B1 | 7/2002 | Yaacobi |
| 6,416,777 B1 | 7/2002 | Yaacobi |
| 6,440,990 B1 | 8/2002 | Cottens et al. |
| 6,455,518 B2 | 9/2002 | Zenke et al. |
| 6,482,802 B1 | 11/2002 | Hu et al. |
| 6,489,335 B2 | 12/2002 | Peyman |
| 6,534,693 B2 | 3/2003 | Fischell et al. |
| 6,569,443 B1 | 5/2003 | Dawson et al. |
| 6,576,224 B1 | 6/2003 | Osbakken et al. |
| 6,617,345 B1 | 9/2003 | Gregory et al. |
| 6,632,836 B1 | 10/2003 | Baker et al. |
| 6,656,460 B2 | 12/2003 | Benita et al. |
| 6,699,493 B2 | 3/2004 | Wong |
| 6,713,081 B2 | 3/2004 | Robinson et al. |
| 6,719,750 B2 | 4/2004 | Varner et al. |
| 6,777,000 B2 | 8/2004 | Ni et al. |
| 6,812,220 B2 | 11/2004 | Jackson et al. |
| 6,864,232 B1 | 3/2005 | Ueno |
| 6,872,383 B2 | 3/2005 | Ueno |
| 6,939,878 B2 | 9/2005 | Naicker et al. |
| 6,956,043 B2 | 10/2005 | Guitard et al. |
| 7,014,861 B2 | 3/2006 | Roorda et al. |
| 7,018,808 B2 | 3/2006 | Leadlay et al. |
| 7,026,374 B2 | 4/2006 | Nathan et al. |
| 7,033,604 B2 | 4/2006 | Ueno |
| 7,033,605 B2 | 4/2006 | Wong |
| 7,034,037 B2 | 4/2006 | Arnold et al. |
| 7,063,857 B1 | 6/2006 | Ueno |
| 7,083,802 B2 | 8/2006 | Peyman |
| 7,083,803 B2 | 8/2006 | Peyman |
| 7,087,237 B2 | 8/2006 | Peyman |
| 7,128,897 B2 | 10/2006 | Osbakken et al. |
| 7,160,867 B2 | 1/2007 | Abel et al. |
| 7,181,287 B2 | 2/2007 | Greenberg |
| 7,183,289 B2 | 2/2007 | Zhang et al. |
| 7,186,518 B2 | 3/2007 | Wang et al. |
| 7,223,286 B2 | 5/2007 | Wright et al. |
| 7,354,574 B2 | 4/2008 | Peyman |
| 7,402,399 B2 | 7/2008 | Mukherjeei et al. |
| 2002/0187998 A1 | 12/2002 | Ueno |
| 2003/0018044 A1 | 1/2003 | Peyman |
| 2003/0027744 A1 | 2/2003 | Dana et al. |
| 2003/0069232 A1 | 4/2003 | Chiou |
| 2003/0069560 A1 | 4/2003 | Adamis et al. |
| 2003/0077297 A1 | 4/2003 | Chen et al. |
| 2003/0171320 A1 | 9/2003 | Guyer |
| 2003/0190286 A1 | 10/2003 | Dugger, III |
| 2003/0203892 A1 | 10/2003 | Keller et al. |
| 2004/0018228 A1 | 1/2004 | Fischell et al. |
| 2004/0057958 A1 | 3/2004 | Waggoner, Jr. et al. |
| 2004/0167152 A1 | 8/2004 | Rubino et al. |
| 2004/0175428 A1 | 9/2004 | Appel et al. |
| 2004/0180075 A1 | 9/2004 | Robinson et al. |
| 2004/0198763 A1 | 10/2004 | Ueno |
| 2004/0219181 A1 | 11/2004 | Viscasillas |
| 2004/0224394 A1 | 11/2004 | Katz et al. |
| 2004/0234611 A1 | 11/2004 | Ahlheim et al. |
| 2005/0032826 A1 | 2/2005 | Mollison et al. |
| 2005/0042215 A1 | 2/2005 | Owen et al. |
| 2005/0048123 A1 | 3/2005 | Su et al. |
| 2005/0064010 A1 | 3/2005 | Cooper et al. |
| 2005/0074497 A1 | 4/2005 | Schultz |
| 2005/0084514 A1 | 4/2005 | Shebuski et al. |
| 2005/0085902 A1 | 4/2005 | Wright et al. |
| 2005/0123605 A1 | 6/2005 | Hunter et al. |
| 2005/0142162 A1 | 6/2005 | Hunter et al. |
| 2005/0143363 A1 | 6/2005 | De Juan et al. |
| 2005/0187241 A1 | 8/2005 | Wen et al. |
| 2005/0196440 A1 | 9/2005 | Masters et al. |
| 2005/0222191 A1 | 10/2005 | Falotico et al. |
| 2005/0232952 A1 | 10/2005 | Lambert et al. |
| 2005/0249710 A1 | 11/2005 | Wong |
| 2005/0250804 A1 | 11/2005 | Kannan et al. |
| 2005/0255144 A1 | 11/2005 | Schultz |
| 2006/0002971 A1 | 1/2006 | Saltzman et al. |
| 2006/0024350 A1 | 2/2006 | Varner et al. |
| 2006/0034891 A1 | 2/2006 | Lawin et al. |
| 2006/0073182 A1 | 4/2006 | Wong et al. |
| 2006/0182771 A1 | 8/2006 | Dor et al. |
| 2006/0182783 A1 | 8/2006 | Hughes et al. |
| 2006/0198867 A1 | 9/2006 | Toner et al. |
| 2006/0216288 A1 | 9/2006 | Chang |
| 2006/0228393 A1 | 10/2006 | Peyman |
| 2006/0228394 A1 | 10/2006 | Peyman |
| 2006/0247265 A1 | 11/2006 | Clackson et al. |
| 2006/0257450 A1 | 11/2006 | Mudumba et al. |
| 2006/0258698 A1 | 11/2006 | Mudumba et al. |
| 2006/0263409 A1 | 11/2006 | Peyman |
| 2006/0264453 A1 | 11/2006 | Mudumba et al. |
| 2006/0275218 A1 | 12/2006 | Tamarkin et al. |
| 2007/0014760 A1 | 1/2007 | Peyman |
| 2007/0015697 A1 | 1/2007 | Peyman |
| 2007/0134244 A1 | 6/2007 | Slakter et al. |
| 2007/0197567 A1 | 8/2007 | Sherris |
| 2007/0203173 A1 | 8/2007 | Mudumba et al. |
| 2007/0265294 A1 | 11/2007 | Kleinman et al. |

FOREIGN PATENT DOCUMENTS

| | | |
|---|---|---|
| CN | 1456350 A | 11/2003 |
| DE | 4022553 A1 | 1/1992 |
| DE | 19810655 A1 | 9/1999 |
| EP | 0041745 A1 | 12/1981 |
| EP | 0041795 A2 | 12/1981 |
| EP | 0467606 A1 | 1/1992 |
| EP | 0904787 A1 | 3/1999 |
| EP | 1142566 A1 | 10/2001 |
| EP | 1126849 B1 | 3/2005 |

(56) References Cited

FOREIGN PATENT DOCUMENTS

| | | |
|---|---|---|
| FR | 2382240 A1 | 9/1978 |
| GB | 2278780 A | 12/1994 |
| JP | 5-194212 A | 8/1993 |
| JP | 9-30966 A | 2/1997 |
| JP | 9-505299 A | 5/1997 |
| JP | 9-315954 A | 12/1997 |
| JP | 10-218787 A | 8/1998 |
| JP | 2001-64198 A | 3/2001 |
| JP | 2002-332225 A | 11/2002 |
| JP | 2003-9899 A | 1/2003 |
| JP | 2008-514719 A | 5/2008 |
| RU | 2123314 C1 | 12/1998 |
| RU | 2149615 C1 | 5/2000 |
| WO | 89/01772 A1 | 3/1989 |
| WO | 92/05179 A1 | 4/1992 |
| WO | 93/19763 A1 | 10/1993 |
| WO | 94/05257 A1 | 3/1994 |
| WO | 94/21642 A1 | 9/1994 |
| WO | 95/14023 A1 | 5/1995 |
| WO | 95/26734 A1 | 10/1995 |
| WO | 95/28984 A1 | 11/1995 |
| WO | 96/36377 A1 | 11/1996 |
| WO | 96/40140 A1 | 12/1996 |
| WO | 96/41865 A1 | 12/1996 |
| WO | 97/10806 A1 | 3/1997 |
| WO | 97/16068 A1 | 5/1997 |
| WO | 99/07418 A2 | 2/1999 |
| WO | 99/11244 A1 | 3/1999 |
| WO | 99/20261 A2 | 4/1999 |
| WO | 99/22722 A2 | 5/1999 |
| WO | 99/34830 A1 | 7/1999 |
| WO | 99/37667 A1 | 7/1999 |
| WO | 99/22722 A3 | 8/1999 |
| WO | 99/45920 A2 | 9/1999 |
| WO | 99/58126 A1 | 11/1999 |
| WO | 00/06121 A1 | 2/2000 |
| WO | 00/09109 A2 | 2/2000 |
| WO | 00/09112 A2 | 2/2000 |
| WO | 00/09479 A2 | 2/2000 |
| WO | 00/28945 A2 | 5/2000 |
| WO | 00/33878 A2 | 6/2000 |
| WO | 00/37066 A2 | 6/2000 |
| WO | 00/38703 A1 | 7/2000 |
| WO | 00/40089 A1 | 7/2000 |
| WO | 00/09109 A3 | 8/2000 |
| WO | 00/56340 A1 | 9/2000 |
| WO | 00/66122 A1 | 11/2000 |
| WO | 01/28522 A2 | 4/2001 |
| WO | 01/30386 A1 | 5/2001 |
| WO | 01/42219 A2 | 6/2001 |
| WO | 01/47495 A1 | 7/2001 |
| WO | 01/93830 A1 | 12/2001 |
| WO | 02/28387 A1 | 4/2002 |
| WO | 02/062335 A2 | 8/2002 |
| WO | 02/066019 A2 | 8/2002 |
| WO | 02/074196 A1 | 9/2002 |
| WO | 02/100318 A2 | 12/2002 |
| WO | 03/017990 A2 | 3/2003 |
| WO | 03/051385 A1 | 6/2003 |
| WO | 03/068186 A1 | 8/2003 |
| WO | 03/074027 A2 | 9/2003 |
| WO | 03/074029 A1 | 9/2003 |
| WO | 03/090684 A2 | 11/2003 |
| WO | 2004/007709 A2 | 1/2004 |
| WO | 2004/011000 A1 | 2/2004 |
| WO | 2004/014373 A1 | 2/2004 |
| WO | 2004/019904 A1 | 3/2004 |
| WO | 2004/027027 A2 | 4/2004 |
| WO | 2004/028477 A2 | 4/2004 |
| WO | 2004/027027 A3 | 5/2004 |
| WO | 2004/043480 A2 | 5/2004 |
| WO | 2004/060283 A2 | 7/2004 |
| WO | 2004/074445 A2 | 9/2004 |
| WO | 2004/096261 A1 | 11/2004 |
| WO | 2005/002625 A2 | 1/2005 |
| WO | 2005/011813 A2 | 2/2005 |
| WO | 2005/020962 A1 | 3/2005 |
| WO | 2005/027906 A1 | 3/2005 |
| WO | 2005/030205 A1 | 4/2005 |
| WO | 2005/051452 A2 | 6/2005 |
| WO | 2005/055945 A2 | 6/2005 |
| WO | 2005/082376 A1 | 9/2005 |
| WO | 2005/094279 A2 | 10/2005 |
| WO | 2005/099715 A2 | 10/2005 |
| WO | 2005/110436 A2 | 11/2005 |
| WO | 2005/110473 A2 | 11/2005 |
| WO | 2006/002365 A2 | 1/2006 |
| WO | 2006/002366 A2 | 1/2006 |
| WO | 2006/002399 A2 | 1/2006 |
| WO | 2006/014484 A2 | 2/2006 |
| WO | 2006/020755 A2 | 2/2006 |
| WO | 2006/023627 A1 | 3/2006 |
| WO | 2006026531 A1 | 3/2006 |
| WO | 2006/039336 A2 | 4/2006 |
| WO | 2006/041942 A2 | 4/2006 |
| WO | 2006/053007 A2 | 5/2006 |
| WO | 2006/039336 A3 | 7/2006 |
| WO | 2006/086744 A1 | 8/2006 |
| WO | 2006/086750 A1 | 8/2006 |
| WO | 2006/102378 A2 | 9/2006 |
| WO | 2006/108239 A1 | 10/2006 |
| WO | 2006/110487 A1 | 10/2006 |
| WO | 2006/116716 A2 | 11/2006 |
| WO | 2006/133052 A2 | 12/2006 |
| WO | 2007/011880 A2 | 1/2007 |
| WO | 2006/102378 A3 | 3/2007 |
| WO | 2007/065588 A1 | 6/2007 |
| WO | 2007/083316 A2 | 7/2007 |
| WO | 2007/092620 A2 | 8/2007 |
| WO | 2007/112052 A2 | 10/2007 |

OTHER PUBLICATIONS

"Photodynamic Therapy of Subfoveal Choroidal Neovascularization in Age-Related Macular Degeneration With Verteporfin, One-Year Results of 2 Randomized Clinical Trials—TAP Report 1", Archives of Ophthalmology, Treatment of Age-Related Macular Degeneration with Photodynamic Therapy (TAP) Study Group, vol. 117, Oct. 1999, pp. 1329-1345.

Aiello et al., "Rapid and Durable Recovery of Visual Function in a Patient with Von Hippel-Lindau Syndrome after Systemic Therapy with Vascular Endothelial Growth Factor Receptor Inhibitor su5416", Ophthalmology, vol. 109, 2002, pp. 1745-1751.

Akselband et al., "Rapamycin Inhibits Spontaneous and Fibroblast Growth Factor Beta-Stimulated Proliferation of Endothelial Cells and Fibroblasts", Transplantation Proceedings vol. 23, No. 6, Dec. 1991, pp. 2833-2836.

Alteheld et al., "Biodegradable Amorphous Copolyester-Urethane Networks Having Shape-Memory Properties", Angewandte Chemie International Edition, vol. 44, 2005, pp. 1188-1192.

Aoyama et al, "The Effect of FK 506, an Immunosuppressant, on Cerebral Infarction Volume in Focal Cerebral Ischemia in Rats", Journal Nippon Medical School, vol. 64, 1997, pp. 416-421.

Apel et al., "A Subconjuctival Degradable Implant for Cyclosporine Delivery in Corneal Transplant Therapy", Current Eye Research, vol. 14, No. 8, Aug. 1995, pp. 659-667.

Aramoto et al., "Vascular Endothelial Growth Factor Stimulates Differential Signaling Pathways in In Vivo Microcirculation", American Journal of Physiology—Heart and Circulatory Physiology, vol. 287, Oct. 2004, pp. H1590-H1598.

Arias, Luis, "Management of Diabetic Macular Edema with Antiangiogenic Therapy", Expert Review of Ophthalmology, vol. 2, No. 1, 2007, pp. 23-26.

Auricchio et al., "Pharmacological Regulation of Protein Expression from Adeno-Associated Viral Vectors in the Eye", Molecular Therapy, vol. 6, No. 2, 2002, pp. 238-242.

Averbukh et al., "Diabetic Macular Edema: Towards Therapy Aimed at the Underlying Pathogenic Mechanisms", The Israel Medical Association Journal, vol. 8, Feb. 2006, pp. 127-128.

Bainbridge et al., "Hypoxia-Regulated Transgene Expression in Experimental Retinal Choroidal Neovascularization", Gene Therapy, vol. 10, 2003, pp. 1049-1054.

(56) References Cited

OTHER PUBLICATIONS

Beeley et al., "Development, Implantation, In Vivo Elution, and Retrieval of a Biocompatible, Sustained Release Subretinal Drug Delivery System", Journal of Biomedical Materials Research Part A 76A, Mar. 15, 2006, pp. 690-698.

Behl, C., "Amyloid Beta-Protein Toxicity and Oxidative Stress in Alzheimer's Disease", Cell & Tissue Research, vol. 290, No. 3, Dec. 1997, pp. 471-480.

Bergers et al., "Tumorigenesis and the Angiogenic Switch", Nature Reviews-Cancer, vol. 3, No. 6, Jun. 2003, pp. 401-410.

Bertelmann et al., "Immunomodulatory Therapy in Ophthalmology—Is There a Place for Topical Application?", Ophthalmologica, vol. 218, 2004, pp. 359-367.

Bourne et al., "Epidemic Optic Neuropathy in Primary School Children in Dar es Salaam, Tanzania", British Journal of Ophthalmology, vol. 82, 1998, pp. 232-234.

Gucci et al., "In Vivo Delivery of the Caveolin-1 Scaffolding Domain Inhibits Nitric Oxide Synthesis and Reduces Inflammation", Nature Medicine, vol. 6, No. 12, Dec. 2000, pp. 1362-1367.

Cancer Weekly Editors, "Cancer Therapy: Study of Possible Anticancer Drug Reveals New Mechanism of Gene Regulation", Cancer Weekly via NewsRx.com and NewsRx.net, Jan. 14, 2003, 2 pages.

Chusid et al., "The Role of the Polymorphonuclear Leukocyte in the Induction of Corneal Edema.", Investigative Ophthalmology & Visual Science, vol. 27, No. 10., Oct. 1986, pp. 1466-1469.

Cicciarelli et al., "Pharmacokinetics of Subconjunctivally Administered Cyclosporine A: Local Delivery Prior to Chemotherapy for Retinoblastoma", IOVS. vol. 42, No. 4, Abstract 1792, 2001.

Ciulla et al., "Age-Related Macular Degeneration: A Review of Experimental Treatments", Survey of Ophthalmology, vol. 43, No. 2, Sep.-Oct. 1998, pp. 134-146.

Ciulla et al., "Diabetic Retinopathy and Diabetic Macular Edema: Pathophysiology, Screening, and Novel Therapies", Diabetes Care vol. 26, No. 9, Sep. 2003, pp. 2653-2664.

Edinger et al., "Differential Effects of Rapamycin on Mammalian Target of Rapamycin Signaling Functions in Mammalian Cells", Cancer Research, vol. 63, Dec. 1, 2003, pp. 8451-8460.

Gardner et al., "Novel Potential Mechanisms for Diabetic Macular Edema: Leveraging New Investigational Approaches", Current Diabetes Reports, vol. 8, 2008, pp. 263-269.

Geroski et al., "Transscleral Drug Delivery for Posterior Segment Disease", Advanced Drug Delivery Reviews vol. 52, 2001, pp. 37-48.

Gilbard, J.P., "EW Interview: Electrolyte Balance is Key to Dry-eye Product's Success", EyeWorld, Feb. 1999, pp. 20-21.

Guba et al., "Rapamycin Inhibits Primary and Metastatic Tumor Growth by Antiangiogenesis: Involvement of Vascular Endothelial Growth Factor", Nature Medicine, vol. 8, No. 2, Feb. 2002, pp. 128-135.

Guba et al., "Rapamycin Inhibits Tumor Growth and Metastasis by Antiangiogenesis", Chirurgisches Forum 2001, May 1, 2001, pp. 37-39.

Hackstein et al., "Rapamycin Inhibits Macropinocytosis and Mannose Receptor-Mediated Endocytosis by Bone Marrow-Derived Dendritic Cells", Blood, vol. 100, No. 3, Aug. 1, 2002, pp. 1084-1087.

Hafizi et al.,, "Differential Effects of Rapamycin, Cyclosporine A, and FK506 on Human Coronary Artery Smooth Muscle Cell Proliferation and Signaling", Vascular Pharmacology, vol. 41, 2005, pp. 167-176.

Harris et al., "Implantation of a Sustained-Release Ganciclovir Implant", Chapter 45 in Vitreoretinal Surgical Techniques, 2001, pp. 521-531.

Hayward et al., "Total Synthesis of Rapamycin via a Novel Titanium-Mediated Aldol Macrocyclization Reaction", Journal of the American Chemical Society, vol. 115, No. 20, 1993, pp. 9345-9346.

Humar et al., "Hypoxia Enhances Vascular Cell Proliferation and Angiogenesis In Vitro Via Rapamycin (mTOR)-Dependent Signaling", The FASEB Journal, vol. 16, 2002, pp. 771-780.

Kulkarni, Prasad S., "Steroidal and Nonsteroidal Drugs in Endotoxin-Induced Uveitis", Journal of Ocular Pharmacology, vol. 10, No. 1, 1994, pp. 329-334.

Kuroki et al., "Rapamycin Inhibits Retinal and Choroidal Neovascularization in Mice", Investigative Ophthalmology & Visual Science, 44:E-Abstract 573, 2003, 2 pages.

Lal, Avtar, "Drop Volume of Commercial Anti-Glaucoma Eye Drops", Indian Journal of Pharmacology, vol. 25, No. 3, 1993, pp. 163-164.

Lallemand, et al., "Cyclosporine a Delivery to the Eye: A Pharmaceutical Challenge," European Journal of Pharmaceutics and Biopharmaceutics, vol. 56, No. 3, 2003, pp. 307-318.

Lipner, Maxine, "Dry Eye 101: Developing Etiologies and Treatments for the Widespread Syndrome", EyeWorld, Feb. 1999, pp. 19-21.

Macular Photocoagulation, Study Group, "Subfoveal Neovascular Lesions in Age-Related Macular Degeneration, Guidelines for Evaluation and Treatment in the Macular Photocoagulation Study", Archives of Ophthalmology, vol. 109, Sep. 1991, pp. 1242-1257.

Macular Photocoagulation Study Group, "Laser Photocoagulation of Subfoveal Neovascular Lesions in Age-Related Macular Degeneration, Results of a Randomized Clinical Trial", Archives of Ophthalmology, vol. 109, Sep. 1991, pp. 1220-1231.

Macular Photocoagulation, Study Group, "Laser Photocoagulation of Subfoveal Recurrent Neovascular Lesions in Age-Related Macular Degeneration, Results of a Randomized Clinical Trial", Archives of Ophthalmology, vol. 109, Sep. 1991, pp. 1232-1241.

Macular Photocoagulation Study Group, "Argon Laser Photocoagulation for Neovascular Maculopathy, Three-Year Results from Randomized Clinical Trials", Archives of Ophthalmology, vol. 104, May 1986, pp. 694-701.

Macusight, Inc.,"Safety and Tolerability of MS-R001 in Patients with Diabetic Macular Edema Secondary to Diabetic Retinopathy", located at <http://clinicaltrials.gov/ct2/show/NCT00401115?term=macular+edema+and+rapamycin&rank=3> visited on Jan. 26, 2009, 3 pages.

Marsland et al., "The Macrolide Immunosuppressants in Dermatology: Mechanisms of Action", European Journal of Dermatology, vol. 12, Nov.-Dec. 2002, pp. 618-621.

Martin et al., "Synergistic Effect of Rapamycin and Cyclosporin A in the Treatment of Experimental Autoimmune Uveoretinitis", The Journal of Immunology, vol. 154, No. 2, Jan. 15, 1995, pp. 922-927.

Mayhan et al., "The Effect of Altering the External Calcium Concentration and a Calcium Channel Blocker, Verapamil, on Microvascular Leaky Sites and Dextran Clearance in the Hamster Cheek Pouch", Microvascular Research, vol. 28, No. 2, Sep. 1984, pp. 159-179.

Medivas, "MediVas Announces Signing of Collaboration Agreement with Pfizer", located at <www.medivas.com/News/news_MediVas_Announces_Signing_of_Collaboration_Agreement_with_Pfizer.html> visited on Jul. 28, 2008., 2007, 1 page.

Murphy,"Management of Diabetic Retinopathy", American Family Physician, vol. 51, No. 4, Mar. 1995, pp. 785-796.

Napoli et al., "From Beach to Bedside: History of the Development of Sirolimus", Therapeutic Drug Monitoring vol. 23, No. 5, 2001, pp. 559-586.

National Eye Institute (NEI),"Sirolimus to Treat Diabetic Macular Edema", located at <http://clinicaltrials.gov/ct2/show/NCT00711490?term=macular+edema+and+rapamycin&rank=1> visited on Jan. 26, 2009, 6 pages.

Nicolaou et al., "Total Synthesis of Rapamycin", Journal of the American Chemical Society, vol. 115, No. 10, 1993, pp. 4419-4420.

Ohia et al., "Effects of Steroids and Immunosuppressive Drugs on Endotoxin-Uveitis in Rabbits", Journal of Ocular Pharmacology, vol. 8, No. 4, 1992, pp. 295-307.

Olsen et al., "Rapamycin Inhibits Corneal Allograft Rejection and Neovascularization", Archives of Ophthalmology, vol. 112, Nov. 1994, pp. 1471-1475.

Paiva et al., "Incorporation of Acetate, Propionate, and Methionine Into Rapamycin by Streptomyces hygroscopicus", Journal of Natural Products, vol. 54, No. 1, Jan.-Feb. 1991, pp. 167-177.

(56) References Cited

OTHER PUBLICATIONS

Passos et al., "Ocular Toxcity of Intravitreal Tacrolimus", Ophthalmic Surgery and Lasers, vol. 33, No. 2, Mar./Apr. 2002, pp. 140-144.
Pavan-Langston, D., "Manual of Ocular Diagnosis and Therapy", Fourth Edition, Little, Brown and Company: New York, 1996, pp. 162-165.
Phung et al., "Pathological Angiogenesis is Induced by Sustained Akt Signaling and Inhibited by Rapamycin", Cancer Cell, vol. 10, Aug. 2006, pp. 159-170.
Raghava et al., "Periocular Routes for Retinal Drug Delivery", Expert Opinion on Drug Delivery, vol. 1, No. 1, Nov. 2004, pp. 99-114.
Renau et al., "Addressing the Stability of C-Capped Dipeptide Efflux Pump Inhibitors that Potentiate the Activity of Levofloxacin in Pseudomonas Aeruginosa", Bioorganic & Medicinal Chemistry Letters, vol. 11, 2001, pp. 663-667.
Renau et al., "Conformationally-Restricted Analogues of Efflux Pump Inhibitors that Potentiate the Activity of Levofloxaxin in Pseudomonas aeruginosa.", Bioorganic & Medicinal Chemistry Letters, vol. 13., 2003, pp. 2755-2758.
Rivera et al., "Long-Term Regulated Expression of Growth Hormone in Mice after Intramuscular Gene Transfer.", Proceedings of the National Academy of Sciences of the United States of America, vol. 96, Jul. 1999, pp. 8657-8662.
Robinson et al., "Bioadhesive and Phase-Change Polymers for Ocular Drug Delivery", Advanced Drug Delivery Reviews, vol. 16, 1995, pp. 45-50.
Romo et al., "Total Synthesis of (-)-Rapamycin Using an Evans-Tishchenko Fragment Coupling", Journal of the American Chemical Society, vol. 115, No. 17, 1993, pp. 7906-7907.
Schlingemann et al., "Role of Vascular Permeability Factor/Vascular Endothelial Growth Factor in Eye Disease.", British Journal of Ophthalmology, vol. 81, No. 6, Jun. 1997, pp. 501-512.
Sehgal et al., "Demethoxyrapamycin (AY-24,668), a New Antifungal Antibiotic", The Journal of Antibiotics, vol. 36, No. 4, Apr. 1983, pp. 351-354.
Sehgal et al., "Rapamycin (AY-22,989), a New Antifungal Antibiotic, II. Fermentation, Isolation and Characterization", The Journal of Antibiotics, vol. 28, No. 10, Oct. 1975, pp. 727-732.
Shen et al., "Combined Effect of Cyclosporine and Sirolimus on Improving the Longevity of Recombinant Adenovirus-Mediated Transgene Expression in the Retina", Archives of Ophthalmology, vol. 119, Jul. 2001, pp. 1033-1043.
Simamora et al., "Solubilization of Rapamycin", International Journal of Pharmaceutics, vol. 213, No. 1-2, 2001, pp. 25-29.
Spaide et al., "Combined Photodynamic Therapy With Verteporfin and Intravitreal Triamcinolone Acetonide for Choroidal Neovascularization", Ophthalmology, vol. 110, No. 8, Aug. 2003, pp. 1517-1525.
Stepkowski et al., "Rapamycin, a Potent Immunosuppressive Drug for Vascularized Heart, Kidney, and Small Bowel Transplantation in the Rat", Transplantation, vol. 51, No. 1, Jan. 1991, pp. 22-26.
Treins et al., "Insulin Stimulates Hypoxia-Inducible Factor 1 Through a Phosphatidylinositol 3-kinase/Target of Rapamycin-Dependent Signaling Pathway", The Journal of Biological Chemistry, vol. 277, No. 31, 2002, pp. 27975-27981.
Vezina et al., "Rapamycin (AY-22,989), a New Antifungal Antibiotic, I. Taxonomy of the Producing Streptomycete and Isolation of the Active Principle", The Journal of Antibiotics, vol. 28, No. 10, Oct. 1975, pp. 721-726.
Wen et al., "Rapamycin Inhibits Choroidal Neovascularization", Investigative Ophthalmology & Visual Science 44: E-Abstract 3928, 2003, 2 pages.
Xue et al., "Palomid 529, a Novel Small-Molecule Drug, Is a TORC1/TORC2 Inhibitor That Reduces Tumor Growth, Tumor Angiogenesis, and Vascular Permeability", Cancer Research, vol. 68. No. 22, Nov. 15, 2008, pp. 9551-9557.
Bartsch et al., "High Altitude Pulmonary Oedema", Swiss Medical Weekly, vol. 133, 2003, pp. 377-384.

Campochiaro et al., "Ocular Neovascularisation and Excessive Vascular Permeability", Expert Opinion on Biological Therapy, vol. 4, 2004, pp. 1395-1402.
Edelman et al., "Corticosteroids inhibit VEGF-Induced Vascular Leakage in a Rabbit Model of Blood-Retinal and Blood-Aqueous Barrier Breakdown", Experimental Eye Research, vol. 80, 2005, pp. 249-258.
El-Harazi et al., "Control of Intra-Ocular Inflammation Associated with Cataract Surgery", Current Opinion in Ophthalmology, vol. 12, 2001, pp. 4-9.
Heo et al., "Free Radicals as Triggers of Brain Edema Formation after Stroke", Free Radic Biol Med., vol. 39, 2005, pp. 51-70.
Ip et al., "Intravitreal Triamcinolone for the Treatment of Macular Edema Associated With Central Retinal Vein Occlusion", Arch Ophthalmol., vol. 122, 2004, pp. 1131-1136.
Irwin et al., "A Potential Role for Reactive Oxygen Species and the HIF-1 Alpha-VEGF Pathway in Hypoxia-Induced Pulmonary Vascular Leak", Free Radic Biol Med., vol. 47, 2009, pp. 55-61.
Iturralde et al., "Intravitreal bevacizumab (Avastin) Treatment of Macular Edema in Central Retinal Vein Occlusion: a Short Term Study", Retina., vol. 26, 2006, pp. 279-284.
Kleinman et al., "Sirolimus Inhibits VEGF-Induced Microvascular Hyperpermeability", Invest Opthalmol Vis Science, vol. 48, No. 1422, (E-Abstract), 2007.
Lange et al., "Assessment of Vascular Permeability in an Ovine Model of Acute Lung Injury and Ipneumonia-Induced Pseudomonas Aeruqinosa Sepsis", Crit Care Med, vol. 36, 2008, pp. 1284-1289.
International Search Report received for PCT Patent Application No. PCT/US2007/007353, mailed on Jan. 15, 2008, 6 pages.
Purvin et al., "Neuroretinitis: Review of the literature and New Observations", Journal of Neuro-Ophthalmology, vol. 31, 2011, pp. 58-68.
Rosenfeld et al., "Optical Coherence Tomography Findings after an Intravitreal Injection of Bevacizumab (Avastin) for Macular Edema from Central Retinal Vein Occlusion", Opthalmic Surg Lasers Imeaina, vol. 36, 2005, pp. 336-339.
Shiga et al., "Cyclosporin A Protects Against Ischemia-Reperfusion Injury in the Brain", Brain Research, vol. 595, 1992, pp. 145-148.
Takahashi et al., "Intraocular Expression of Endostatin Reduces VEGF induced Retinal Vascular Ipermeability, Neovascularization and retinal Detachment", FASEB J, vol. 17, 2003, pp. 896-898.
Taniguchi et al., "Role of Platelet-Activating Factor in Pulmonary Edema after Coronary Ligation in Doqs", Chest, vol. 102, No. 4, 1992, pp. 1245-1250.
Uhlig et al., "Mechanisms of Platelet-Activating Factor (PAF)-Mediated Responses in the Lung", Pharmaco/ Rep., vol. 57, 2005, pp. 206-211.
Yamamoto et al., "Vitrectomy for Diabetic Macular Edema: The Role of Posterior Vitreous Detachment and the Epimacular Membrane", American Journal of Ophthalmology, vol. 132, 2001, pp. 369-377.
International Written Opinion received for PCT Patent Application No. PCT/US2007/007353, mailed on Jan. 15, 2008, 6 pages.
International Preliminary Report on Patentability received for PCT Patent Application No. PCT/US2007/007353, issued on Sep. 23, 2008, 7 pages.
Dejneka et al., "Systemic Rapamycin Inhibits Retinal and Choroidal Neovascularization in Mice", Molecular Vision, vol. 10, 2004, pp. 964-972.
Dvorak et al., "Vascular Permeability FactorNascular Endothelial Growth Factor, Microvascular Hyperpermeability, and Angiogenesis", American Journal of Pathology, vol. 146, No. 5, May 1995, pp. 1029-1039.
Fine et al., "Aqueous Humor and Plasma Vascular Endothelial Growth Factor in Uveitis-Associated Cystoid Macular Edema", American Journal of Ophthalmology, vol. 132, No. 5, Nov. 2001, pp. 794-796.
Matsuda et al., "Sarcoidosis with High Serum Levels of Vascular Endothelial Growth Factor (VEGF), Showing RS3PE-Like Symptoms in Extremities", Clin Rheumatol, vol. 23, 2004, pp. 246-248.
Tranos et al., "Macular Edema", Survey of Ophthalmology, vol. 49, No. 5, Sep.-Oct. 2004, pp. 470-490.

* cited by examiner

FORMULATIONS AND METHODS FOR VASCULAR PERMEABILITY-RELATED DISEASES OR CONDITIONS

CROSS-REFERENCE TO RELATED APPLICATIONS

The present application is a continuation of U.S. application Ser. No. 13/530,025, filed Jun. 21, 2012, which is a continuation of U.S. application Ser. No. 11/726,813, filed Mar. 23, 2007, now U.S. Pat. No. 8,222,271, which is related to and claims priority from U.S. Provisional Patent Application Ser. No. 60/785,814, filed Mar. 23, 2006, which are incorporated herein by reference in their entirety.

FIELD

Described herein are formulations and methods for treatment, prevention, inhibition, delaying onset of, or causing regression of a vascular permeability-related disease or condition by delivery of a formulation comprising a therapeutic agent to a subject in need thereof, including but not limited to a human subject. In some variations the therapeutic agent includes limus compounds and immunophilin binding compounds, including but not limited to rapamycin (sirolimus).

BACKGROUND

The development and maturation of blood vessels results from a complex interplay of pro- and anti-angiogenic regulators. Dysregulation of the balance between these factors is thought to result in the formation of pathological blood vessels, such as blood vessels with increased vascular permeability (Bergers and Benjamin, *Nat. Rev. Cancer* 3:401-410, 2003). Increased vascular permeability has been implicated in numerous pathologies; non-limiting examples include vascular diseases and disorders of the eye, diabetes, cancer, pulmonary hypertension, and various edemas.

As one non-limiting example, consider the eye. The eye contains highly vascularized and completely avascular tissues in close apposition. This specialized anatomy requires regulation of the balance between vascular quiescence and vascular growth (Schlingemann et al., *Br. J. Ophthalmol.* 81:501-51, 1991). In eye diseases associated with angiogenesis and vascular permeability, this delicate balance is disturbed. Some leading causes of severe vision loss and blindness are ocular-related disorders wherein the vasculature of the eye is damaged or insufficiently regulated. Ocular-related diseases with a vascular permeability element include, for example, exudative age-related macular degeneration, diabetic retinopathy, corneal neovascularization, choroidal neovascularization, neovascular glaucoma, cyclitis, Hippel-Lindau disease, reinopathy of prematurity, pterygium, histoplasmosis, iris neovasularization, macular edema, glaucoma-associated neovascularization, and the like. Vision loss may be caused by increased vessel permeability, or increased vessel permeability may be correlated with one or more symptoms which impair the eye's function or otherwise inconvenience or cause discomfort in the patient. As non-limiting examples, accumulation of fluid within the eye and the vitreal cavity can instigate retinal detachment, degeneration of sensory cells of the eye, increased intraocular pressure, and inflammation, all of which adversely affect vision and the general health of the eye.

As another non-limiting example, there are two kinds of diabetic retinopathy. The first is non-proliferative retinopathy, which is an earlier stage of the disease characterized by increased capillary permeability, microaneurysms, hemorrhages, exudates, and edema. Most vision loss during this stage is due to the fluid accumulating in the macula due to vascular leakage. This accumulation of fluid is called macular edema and can cause temporary or permanent decreased vision. Prolonged periods of vascular leakage can ultimately lead to the thickening of the basement membrane and formation of soft and hard exudates. The second category of diabetic retinopathy is called proliferative retinopathy and is characterized by abnormal new vessel formation, which grows on the vitreous surface or extends into the vitreous cavity. These newly formed blood vessels of the retina or choroid are often permeable, which allows leakage of vascular fluid into the surrounding tissue and formation of fibrotic tissue and scarring. The leakage of material from the vasculature into the tissues of the eye and scarring can lead to vision loss.

For many ocular-related disorders, including retinal, choroidal, and macular edema, there are no efficient therapeutic options currently available. Laser photocoagulation is employed to administer laser burns. For example, focal macular photocoagulation is used to treat areas of vascular leakage outside the macula (Murphy, *Amer. Family Physician* 51:785-796, 1995). Advanced proliferative retinopathy is commonly treated with scatter or panretinal photocoagulation. The laser treatment may cause permanent blind spots corresponding to the treated areas. Laser treatment may also cause persistent or recurrent hemorrhage, induce neovascularization or fibrosis, or increase risk of retinal detachment. In addition, some patients fail to respond to laser treatments.

Treatments for ocular diseases or conditions and other types of permeability-related diseases or conditions which have decreased dangerous side-effects would be advantageous.

Another disease or disorder characterized by increased vascular permeability is pulmonary hypertension. Pulmonary hypertension is a rare blood vessel disorder of the lung in which the pressure in the pulmonary artery (the blood vessel leading from the heart to the lungs) rises above normal levels and may become life threatening. One cause of pulmonary hypertension is alveolar hypoxia, which results from localized inadequate ventilation of well-perfused alveoli or from a generalized decrease in alveolar ventilation. Pulmonary hypertension is also a vascular permeability related disease. Pulmonary hypertension has been historically chronic and incurable with a poor survival rate. Treatment of pulmonary hypertension usually involves continuous use of oxygen. Pulmonary vasodilators (e.g., hydralazine, calcium blockers, nitrous oxide, prostacyclin) have not proven effective, and lung transplant is often required for patients who do not respond to therapy.

While illustrative ocular disorders and pulmonary hypertension were described above, they are merely non-limiting examples of a few of the types of problems which can be caused by increased vascular permeability. In addition to ocular diseases and disorders and pulmonary hypertension, increased vascular permeability has been found to play a role in the pathophysiology of a variety of other diseases and disorders.

Despite the prevalence of vascular permeability-related disorders, there remains a need for better therapeutic treatments thereof.

SUMMARY

Described herein are methods of treating, inhibiting, preventing, delaying onset, or causing regression of a disease or condition relating to vascular permeability, wherein the method comprises administering an effective amount of a formulation comprising a therapeutic agent to a subject in need thereof, wherein the therapeutic agent is a limus compound, or a pharmaceutically acceptable prodrug, analog, salt, ester, or derivative thereof.

Described herein are methods of treating, inhibiting, preventing, delaying onset, or causing regression of a disease or condition relating to vascular permeability, wherein the method comprises administering an effective amount of a formulation comprising a therapeutic agent to a subject in need thereof, wherein the therapeutic agent is an immunophilin binding compound, or a pharmaceutically acceptable prodrug, analog, salt, ester, or derivative thereof.

In some variations the therapeutic agent is a limus compound or pharmaceutically acceptable salt or ester thereof.

In some variations the therapeutic agent is an immunophilin binding compound or pharmaceutically acceptable salt or ester thereof.

Described herein are methods of treating, inhibiting, preventing, delaying onset, or causing regression of a disease or condition relating to vascular permeability, wherein the method comprises administering an effective amount of a formulation comprising a therapeutic agent to a subject in need thereof, wherein the therapeutic agent is selected from the group consisting of rapamycin, SDZ-RAD, tacrolimus, everolimus, pimecrolimus, CCI-779, AP23841, ABT-578, TAFA-93, RAD-001, temsirolimus, AP23573, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, monoester derivatives of rapamycin, diester derivatives of rapamycin, 27-oximes of rapamycin; 42-oxo analogs of rapamycin; bicyclic rapamycins; rapamycin dimers; silyl ethers of rapamycin; rapamycin arylsulfonates, rapamycin sulfamates, monoesters at positions 31 and 42, diesters at positions 31 and 42, 30-demethoxy rapamycin, and pharmaceutically acceptable salts and esters thereof.

In some variations the therapeutic agent is selected from the group consisting of rapamycin, SDZ-RAD, tacrolimus, everolimus, pimecrolimus, CCI-779, AP23841, ABT-578, and pharmaceutically acceptable salts and esters thereof.

In some variations the amount of therapeutic agent in the formulation is equivalent to between 20 μg and 4 mg of rapamycin.

In some variations the disease or condition relating to vascular permeability is selected from the group consisting of edema associated with capillary leak, edema associated with capillary permeability, diseases with edema as a complication, edema associated with venous obstruction, edema associated with lymphatic obstruction, edema associated with pulmonary disease, edema associated with infectious conditions, edema associated with inflammatory, noninfectious, or autoimmune conditions, edema associated with neurologic conditions, edema associated with neoplasms or tumors, diseases associated with dermatologic diseases or conditions, edema associated with genetic, congenital, or cystic abnormalities, edema due to environmental or other exposure, edema caused by acute trauma or injury, edema associated with infarction and ischemia reperfusion, miscellaneous causes of edema, or edema associated with systemic conditions.

In some variations the disease or condition relating to vascular permeability is selected from the group consisting of cardiomyopathy, dilated cardiomyopathy, hypertrophic cardiomyopathy, restrictive cardiomyopathy, congestive heart failure, filariasis, kidney failure, lymphedema, preeclampsia, eclampsia, thyroid condition, varicosity, varicose veins, aortic coarctation, cor pulmonale, exudative dermatitis, Hodgkin's disease, pericarditis, nephrogenic pulmonary edema, thrombophlebitis, thrombosis, neoplasm, varicosity, arteriovenous fistula, lymph node mass, aneurysm, filariasis, cellulitis, neoplasm, surgical excision, pulmonary edema, chronic obstructive pulmonary disease, pleural effusion, aspiration pneumonitis, asthma induced edema, amniotic fluid embolism, boils, carbuncle, abscess, erysipelas, osteomyelitis, gas gangrene, erysipelas, anthrax, Ludwig's angina, parasitic infections, trichinosis, viral encephalitis, AIDS, herpes simplex virus infection, herpes zoster virus infection, tuberculosis (disseminated, military, etc.), neurosyphilis, prion diseases, meningitis, pneumococcal meningitis, rabies, neuroretinitis, anthrax exposure, endotoxin induced edema, Wegeners granulomatosis, Sjogren's syndrome, scleroderma, systemic Lupus erythematosis, sarcoidosis, multiple sclerosis, Reiter's syndrome, Pyogenic granuloma, vasculitis, demyelinating diseases, benign intracranial hypertension, papilledema, optic neuritis, multi-infarct dementia, Alzheimers disease, amyloid deposition diseases, toxic metabolic brain edema, cerebral amyloid angiopathy, post-ictal state, blood brain barrier dysfunction, Vogt-Koyanagi-Harada syndrome, prophylactic use in carotid endarterectomy, vasogenic brain edema, choroidal melanoma, choroidal nevus, melanoma, neuroma, epithelioma, lymphangioma, myxoma, fibroma, fibromyoma, osteoma, chondroma, angioma, angiosarcoma, peritumoral brain edema, hemangiomas, carcinoid, multiple endocrine neoplasia, porphyria cutanea tarda, pemphigoid, dermatitis herpetiformis, pemphigous, empitigo, erythema multiforme, exudative dermatitis, epidermolysis bullosa, contact dermatitis, actinic dermatitis, toxic erythema, dermatomyositis, eczema, toxic epidermal necrolysis, xeroderma pigmentosa, hydrocoele, dermoid cyst, ovarian cyst, amniotic band, arteriovenous fistula, meningocoele, hydrocephalus, hereditary angioneurotic edema, neurofibromatosis, Von Hippel Lindau disease, tuberous sclerosis, acute nephritis, angioneurotic edema, scleroderma, hypersensitivity reactions, transfusion reactions, acute mountain sickness, high altitude pulmonary edema (HAPE), high altitude cerebral edema (HACE), tropical edema, chilblains, drug toxicity, poisonings, anoxia due to smoke inhalation, carbon monoxide poisoning, or near drowning, exposure to noxious gases, poison ivy, poison oak, poison sumac, or nettles exposure, cholinergic intoxication, edema from systemic steroid therapy, ethanol induced brain injury, hyponatremic brain edema, acute trauma from bone, joint, soft tissue, or organ injury, prophylactic treatment to prevent swelling in athletics or sporting activities, bruise, contusion, ligamentous sprain or tendonous strain, bursitis, joint injuries, fracture, insect bite, snake bite, insect bites, marine intoxications or envenomations due to sponges, corals, sea anemones, sea urchins, sting ray, scorpion fish, or jelly fish stings, exposure to an irritant or corrosive, frostbite, burn, sunburn, electrical injury, traumatic brain injury, spinal cord injury, traumatic optic neuropathy, subdural hematoma, subarachnoid hematoma, carotid cavernous fistula, stroke, myocardial infarction, arterial obstruction, arterial laceration, extremity amputation requiring replantation, central retinal artery occlusion, branch retinal artery occlusion, anterior or posterior ischemic optic neuropathy, ischemia induced edema, gout, angioneurotic edema, Milroy's disease, corneal edema, episceritis, scleritis, choroidal effusion, conjunctival edema, exudative retinal detachment, ventriculoperitoneal shunt malfunction, CSF drainage obstruction, aphthous ulcer, leukoplakia, epiglotitis, cytotoxic edema, laryngeal edema, chronic cough, lichen planus, pancreatitis, blepharitis, eyelid swelling, polymyositis, anaphylactic shock, shock, sepsis, acute respiratory distress syndrome (ARDS), intensive care patient, heart lung bypass induced brain edema, cold induced brain edema, hepatic failure induced brain edema, sympathetic ophthalmia, sarcoma, high altitude retinal hemorrhages, blunt and penetrating ocular and orbital trauma, hypertensive retinopathy, macular star, orbital cellulitis, choroidal infarction, frosted branch angiitis, sickle cell disease, papillomas, keratitis, dacryoadenitis, canaliculitis, dacryocystitis, contact lens induced conjunctivitis, interstitial keratitis, ligneous conjunctivitis, pinguecula, pterygium, cornea gutata, adenomas, capillary hemangioma, cavernous hemangioma, hemangioendothelioma, hemangiopericytoma, kaposi's sarcoma, choristoma, benign reactive lymphoid hyperplasia, lymphoid neoplasia, hordeolum, chalazion, xanthomatous tumors, corneal graft edema, and corneal edema associated with refractive procedures, and ptosis.

In some variations the disease or condition is a member from the group consisting of cellulitis, eyelid edema, neoplasm, herpes simplex virus infection, herpes zoster virus infection, tuberculosis, neurosyphilis, Wegeners granulomatosis, Sjogren's syndrome, scleroderma, systemic Lupus erythematosis, sarcoidosis, multiple sclerosis, Reiter's syndrome, Pyogenic granuloma, vasculitis, or demyelinating diseases, pappiledema, optic neuritis, amyloid deposition diseases, Vogt-Koyanagi-Harada syndrome, choroidal melanoma, choroidal nevus, melanoma, neuroma, epithelioma, lymphangioma, myxoma, fibroma, fibromyoma, osteoma, chondroma, hemangioma, Rosacea, dermatitis, pemphigoid, erythema multiforme, neurofibromatosis, Von Hippel Lindau disease, or tuberous sclerosis, hypersensitivity reactions, drug toxicity, acute trauma, insect bite, burn, traumatic optic neuropathy, carotid cavernous fistula, central retinal artery occlusion, branch retinal artery occlusion, anterior or posterior ischemic optic neuropathy, or ischemia induced edema, corneal edema, episceritis, scleritis, choroidal effusion, conjunctival edema, exudative retinal detachment, ventriculoperitoneal shunt malfunction, CSF drainage obstruction, blepharitis, eyelid swelling Described herein are methods to treat the diseases or conditions described herein.

Described herein are methods to prevent the disease or condition.

In some variations the formulation comprising the therapeutic agent is placed rectally, vaginally, by infusion, intramuscularly, intraperitoneally, intraarterially, intrathecally, intrabronchially, intracisternally, cutaneously, subcutaneously, intradermally, transdermally, intravenously, intracervically, intraabdominally, intracranially, intraocularly, periocularly, intrapulmonarily, intrathoracically, intratracheally, nasally, buccally, sublingually, orally, parenterally, topically, by implantation, as part of an embolization procedure, transcutaneously, directly into a nerve, directly into the optic nerve, direct injection into the optic nerve head, transretinally, transsclerally into an area of effusion or exudation, or inhaled after nebulisation or aerosolization.

Described herein are methods of treatment comprising administering a formulation comprising an effective amount of a limus compound to treat, prevent, inhibit, delay onset of, or cause regression of any one or more of cardiomyopathy, dilated cardiomyopathy, hypertrophic cardiomyopathy, restrictive cardiomyopathy, congestive heart failure, filariasis, kidney failure, lymphedema, preeclampsia, eclampsia, thyroid condition, varicosity, varicose veins, aortic coarcation, cor pulmonale, exudative dermatitis, Hodgkin's disease, pericarditis, nephrogenic pulmonary edema, varicosity, arteriovenous fistula, lymph node mass, aneurysm, filariasis, neoplasm, surgical excision, pulmonary edema, chronic obstructive pulmonary disease, pleural effusion, aspiration pneumonitis, asthma induced edema, amniotic fluid embolism, boils, carbuncle, abscess, erysipelas, osteomyelitis, gas gangrene, erysipelas, anthrax, Ludwig's angina, parasitic infections, trichinosis, viral encephalitis, AIDS, herpes simplex virus infection, prion diseases, rabies, neuroretinitis, anthrax exposure, endotoxin induced edema, Wegeners granulomatosis, Sjogren's syndrome, scleroderma, systemic Lupus erythematosis, multiple sclerosis, Pyogenic granuloma, vasculitis, demyelinating diseases, benign intracranial hypertension, multi-infarct dementia, Alzheimers disease, amyloid deposition diseases, toxic metabolic brain edema, cerebral amyloid angiopathy, post-ictal state, blood brain barrier dysfunction, prophylactic use in carotid endarterectomy, vasogenic brain edema, choroidal nevus, neuroma, epithelioma, lymphangioma, myxoma, fibroma, fibromyoma, osteoma, chondroma, angioma, angiosarcoma, peritumoral brain edema, hemangiomas, carcinoid, multiple endocrine neoplasia, porphyria cutanea tarda, pemphigoid, dermatitis herpetiformis, pemphigous, empitigo, erythema multiforme, exudative dermatitis, epidermolysis bullosa, contact dermatitis, actinic dermatitis, toxic erythema, dermatomyositis, eczema, toxic epidermal necrolysis, xeroderma pigmentosa, hydrocoele, dermoid cyst, ovarian cyst, amniotic band, arteriovenous fistula, meningocoele, hydrocephalus, hereditary angioneurotic edema, neurofibromatosis, Von Hippel Lindau disease, tuberous sclerosis, acute nephritis, angioneurotic edema, scleroderma, hypersensitivity reactions, transfusion reactions, acute mountain sickness, high altitude pulmonary edema (HAPE), high altitude cerebral edema (HACE), tropical edema, chilblains, drug toxicity, poisonings, anoxia due to smoke inhalation, carbon monoxide poisoning, or near drowning, exposure to noxious gases, poison ivy, poison oak, poison sumac, or nettles exposure, cholinergic intoxication, edema from systemic steroid therapy, ethanol induced brain injury, hyponatremic brain edema, acute trauma from bone, joint, soft tissue, or organ injury, prophylactic treatment to prevent swelling in athletics or sporting activities, ligamentous sprain or tendonous strain, bursitis, joint injuries, fracture, insect bite, snake bite, insect bites, marine intoxications or envenomations due to sponges, corals, sea anemones, sea urchins, sting ray, scorpion fish, or jelly fish stings, frostbite, electrical injury, traumatic brain injury, spinal cord injury, traumatic optic neuropathy, subdural hematoma, subarachnoid hematoma, carotid cavernous fistula, stroke, myocardial infarction, arterial obstruction, arterial laceration, extremity amputation requiring replantation, gout, angioneurotic edema, Milroy's disease, corneal edema, choroidal effusion, conjunctival edema, ventriculoperitoneal shunt malfunction, CSF drainage obstruction, aphthous ulcer, leukoplakia, epiglotitis, cytotoxic edema, laryngeal edema, chronic cough, lichen planus, pancreatitis, polymyositis, anaphylactic shock, shock, sepsis, acute respiratory distress syndrome (ARDS), intensive care patient, heart lung bypass induced brain edema, cold induced brain edema, hepatic failure induced brain edema, high altitude retinal hemorrhages, macular star, choroidal infarction, frosted branch angiitis, papillomas, dacryoadenitis, canaliculitis, cornea gutata, adenomas, capillary hemangioma, cavernous hemangioma, hemangioendothelioma, hemangiopericytoma, choristoma, benign reactive lymphoid hyperplasia, lymphoid neoplasia, corneal graft edema, and corneal edema associated with refractive procedures.

Described herein are methods of treatment comprising administering a formulation comprising an effective amount of an immunophilin binding compound to treat, prevent, inhibit, delay onset of, or cause regression of any one or more of cardiomyopathy, dilated cardiomyopathy, hypertrophic cardiomyopathy, restrictive cardiomyopathy, congestive heart failure, filariasis, kidney failure, lymphedema, preeclampsia, eclampsia, thyroid condition, varicosity, varicose veins, aortic coarcation, cor pulmonale, exudative dermatitis, Hodgkin's disease, pericarditis, nephrogenic pulmonary edema, varicosity, arteriovenous fistula, lymph node mass, aneurysm, filariasis, neoplasm, surgical excision, pulmonary edema, chronic obstructive pulmonary disease, pleural effusion, aspiration pneumonitis, asthma induced edema, amniotic fluid embolism, boils, carbuncle, abscess, erysipelas, osteomyelitis, gas gangrene, erysipelas, anthrax, Ludwig's angina, parasitic infections, trichinosis, viral encephalitis, AIDS, herpes simplex virus infection, prion diseases, rabies, neuroretinitis, anthrax exposure, endotoxin induced edema, Wegeners granulomatosis, Sjogren's syndrome, scleroderma, systemic Lupus erythematosis, multiple sclerosis, Pyogenic granuloma, vasculitis, demyelinating diseases, benign intracranial hypertension, multi-infarct dementia, Alzheimers disease, amyloid deposition diseases, toxic metabolic brain edema, cerebral amyloid angiopathy, post-ictal state, blood brain barrier dysfunction, prophylactic use in carotid endarterectomy, vasogenic brain edema, choroidal nevus, neuroma, epithelioma, lymphangioma, myxoma, fibroma, fibromyoma, osteoma, chondroma, angioma, angiosarcoma, peritumoral brain edema, hemangiomas, carcinoid, multiple endocrine neoplasia, porphyria cutanea tarda, pemphigoid, dermatitis herpetiformis, pemphigous, empitigo, erythema multiforme, exudative dermatitis, epidermolysis bullosa, contact dermatitis, actinic dermatitis, toxic erythema, dermatomyositis, eczema, toxic epidermal necrolysis, xeroderma pigmentosa, hydrocoele, dermoid cyst, ovarian cyst, amniotic band, arteriovenous fistula, meningocoele, hydrocephalus, hereditary angioneurotic edema, neurofibromatosis, Von Hippel Lindau disease, tuberous sclerosis, acute nephritis, angioneurotic edema, scleroderma, hypersensitivity reactions, transfusion reactions, acute mountain sickness, high altitude pulmonary edema (HAPE), high altitude cerebral edema (HACE), tropical edema, chilblains, drug toxicity, poisonings, anoxia due to smoke inhalation, carbon monoxide poisoning, or near drowning, exposure to noxious gases, poison ivy, poison oak, poison sumac, or nettles exposure, cholinergic intoxication, edema from systemic steroid therapy, ethanol induced brain injury, hyponatremic brain edema, acute trauma from bone, joint, soft tissue, or organ injury, prophylactic treatment to prevent swelling in athletics or sporting activities, ligamentous sprain or tendonous strain, bursitis, joint injuries, fracture, insect bite, snake bite, insect bites, marine intoxications or envenomations due to sponges, corals, sea anemones, sea urchins, sting ray, scorpion fish, or jelly fish stings, frostbite, electrical injury, traumatic brain injury, spinal cord injury, traumatic optic neuropathy, subdural hematoma, subarachnoid hematoma, carotid cavernous fistula, stroke, myocardial infarction, arterial obstruction, arterial laceration, extremity amputation requiring replantation, gout, angioneurotic edema, Milroy's disease, corneal edema, choroidal effusion, conjunctival edema, ventriculoperitoneal shunt malfunction, CSF drainage obstruction, aphthous ulcer, leukoplakia, epiglotitis, cytotoxic edema, laryngeal edema, chronic cough, lichen planus, pancreatitis, polymyositis, anaphylactic shock, shock, sepsis, acute respiratory distress syndrome (ARDS), intensive care patient, heart lung bypass induced brain edema, cold induced brain edema, hepatic failure induced brain edema, high altitude retinal hemorrhages, macular star, choroidal infarction, frosted branch angiitis, papillomas, dacryoadenitis, canaliculitis, cornea gutata, adenomas, capillary hemangioma, cavernous hemangioma, hemangioendothelioma, hemangiopericytoma, choristoma, benign reactive lymphoid hyperplasia, lymphoid neoplasia, corneal graft edema, and corneal edema associated with refractive procedures.

Described herein are methods of treatment comprising administering a formulation comprising an effective amount of a therapeutic agent to treat, prevent, inhibit, delay onset of, or cause regression of any one or more of cardiomyopathy, dilated cardiomyopathy, hypertrophic cardiomyopathy, restrictive cardiomyopathy, congestive heart failure, filariasis, kidney failure, lymphedema, preeclampsia, eclampsia, thyroid condition, varicosity, varicose veins, aortic coarcation, cor pulmonale, exudative dermatitis, Hodgkin's disease, pericarditis, nephrogenic pulmonary edema, varicosity, arteriovenous fistula, lymph node mass, aneurysm, filariasis, neoplasm, surgical excision, pulmonary edema, chronic obstructive pulmonary disease, pleural effusion, aspiration pneumonitis, asthma induced edema, amniotic fluid embolism, boils, carbuncle, abscess, erysipelas, osteomyelitis, gas gangrene, erysipelas, anthrax, Ludwig's angina, parasitic infections, trichinosis, viral encephalitis, AIDS, herpes simplex virus infection, prion diseases, rabies, neuroretinitis, anthrax exposure, endotoxin induced edema, Wegeners granulomatosis, Sjogren's syndrome, scleroderma, systemic Lupus erythematosis, multiple sclerosis, Pyogenic granuloma, vasculitis, demyelinating diseases, benign intracranial hypertension, multi-infarct dementia, Alzheimers disease, amyloid deposition diseases, toxic metabolic brain edema, cerebral amyloid angiopathy, post-ictal state, blood brain barrier dysfunction, prophylactic use in carotid endarterectomy, vasogenic brain edema, choroidal nevus, neuroma, epithelioma, lymphangioma, myxoma, fibroma, fibromyoma, osteoma, chondroma, angioma, angiosarcoma, peritumoral brain edema, hemangiomas, carcinoid, multiple endocrine neoplasia, porphyria cutanea tarda, pemphigoid, dermatitis herpetiformis, pemphigous, empitigo, erythema multiforme, exudative dermatitis, epidermolysis bullosa, contact dermatitis, actinic dermatitis, toxic erythema, dermatomyositis, eczema, toxic epidermal necrolysis, xeroderma pigmentosa, hydrocoele, dermoid cyst, ovarian cyst, amniotic band, arteriovenous fistula, meningocoele, hydrocephalus, hereditary angioneurotic edema, neurofibromatosis, Von Hippel Lindau disease, tuberous sclerosis, acute nephritis, angioneurotic edema, scleroderma, hypersensitivity reactions, transfusion reactions, acute mountain sickness, high altitude pulmonary edema (HAPE), high altitude cerebral edema (HACE), tropical edema, chilblains, drug toxicity, poisonings, anoxia due to smoke inhalation, carbon monoxide poisoning, or near drowning, exposure to noxious gases, poison ivy, poison oak, poison sumac, or nettles exposure, cholinergic intoxication, edema from systemic steroid therapy, ethanol induced brain injury, hyponatremic brain edema, acute trauma from bone, joint, soft tissue, or organ injury, prophylactic treatment to prevent swelling in athletics or sporting activities, ligamentous sprain or tendonous strain, bursitis, joint injuries, fracture, insect bite, snake bite, insect bites, marine intoxications or envenomations due to sponges, corals, sea anemones, sea urchins, sting ray, scorpion fish, or jelly fish stings, frostbite, electrical injury, traumatic brain injury, spinal cord injury, traumatic optic neuropathy, subdural hematoma, subarachnoid hematoma, carotid cavernous fistula, stroke, myocardial infarction, arterial obstruction, arterial laceration, extremity amputation requiring replantation, gout, angioneurotic edema, Milroy's disease, corneal edema, choroidal effusion, conjunctival edema, ventriculoperitoneal shunt malfunction, CSF drainage obstruction, aphthous ulcer, leukoplakia, epiglotitis, cytotoxic edema, laryngeal edema, chronic cough, lichen planus, pancreatitis, polymyositis, anaphylactic shock, shock, sepsis, acute respiratory distress syndrome (ARDS), intensive care patient, heart lung bypass induced brain edema, cold induced brain edema, hepatic failure induced brain edema, high altitude retinal hemorrhages, macular star, choroidal infarction, frosted branch angiitis, papillomas, dacryoadenitis, canaliculitis, cornea gutata, adenomas, capillary hemangioma, cavernous hemangioma, hemangioendothelioma, hemangiopericytoma, choristoma, benign reactive lymphoid hyperplasia, lymphoid neoplasia, corneal graft edema, and corneal edema associated with refractive procedures, wherein the therapeutic agent is selected from the group consisting of rapamycin, SDZ-RAD, tacrolimus, everolimus, pimecrolimus, CCI-779, AP23841, ABT-578, TAFA-93, RAD-001, temsirolimus, AP23573, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, monoester derivatives of rapamycin, diester derivatives of rapamycin, 27-oximes of rapamycin; 42-oxo analogs of rapamycin; bicyclic rapamycins; rapamycin dimers; silyl ethers of rapamycin; rapamycin arylsulfonates, rapamycin sulfamates, monoesters at positions 31 and 42, diesters at positions 31 and 42, 30-demethoxy rapamycin, and pharmaceutically acceptable salts and esters thereof.

Described herein are methods to treat, prevent, inhibit, delay onset of, or cause regression of a disease or condition comprising administering to a subject in need thereof an effective antipermeability amount of a therapeutic agent, wherein the disease or condition is selected from the group consisting of retinal edema, influenza, viral encephalitis, neuroretinitis, endotoxin induced edema, vasculitis, toxic metabolic brain edema, hemangiomas, von Hippel Lindau disease, angioneurotic edema, snake bite, high altitude cerebral edema (HACE), high altitude pulmonary edema (HAPE), pulmonary edema associated with smoke inhalation, pulmonary edema associated with anoxia, hyponatremic brain edema, edema associated with blunt trauma, brain edema following stroke or closed head injury, and corneal edema.

Described herein are methods to treat, prevent, inhibit, delay onset of, or cause regression of a disease or condition comprising administering to a subject in need thereof an effective antipermeability amount of a therapeutic agent, wherein the therapeutic agent is administered to the subject in need thereof at a dose of no greater than an amount equivalent to 2 mg/kg of rapamycin, and the disease or condition is selected from the group consisting of diabetic macular edema, cystoid macular edema, macular edema from vein occlusion, congestive heart failure, pulmonary edema, ARDS, asthma induced pulmonary edema, hemangioblastoma, pemphigous, tuberous sclerosis, edema secondary to bites or stings, Vogt-Koyanagi-Harada disease, scleritis, and exudative retinal detachment.

In some variations the therapeutic agent is a limus compound or an analog, derivative, salt, or ester thereof. In some variations the therapeutic agent is an immunophilin binding compound or an analog, derivative, salt, or ester thereof. In some variations the therapeutic agent is selected from the group consisting of rapamycin, SDZ-RAD, tacrolimus, everolimus, pimecrolimus, CCI-779, AP23841, ABT-578, TAFA-93, RAD-001, temsirolimus, AP23573, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, monoester derivatives of rapamycin, diester derivatives of rapamycin, 27-oximes of rapamycin; 42-oxo analogs of rapamycin; bicyclic rapamycins; rapamycin dimers; silyl ethers of rapamycin; rapamycin arylsulfonates, rapamycin sulfamates, monoesters at positions 31 and 42, diesters at positions 31 and 42, 30-demethoxy rapamycin, and pharmaceutically acceptable salts and esters thereof. In some variations the therapeutic agent is selected from the group consisting of rapamycin, SDZ-RAD, tacrolimus, everolimus, pimecrolimus, CCI-779, AP23841, ABT-578, and pharmaceutically acceptable salts and esters thereof. In some variations the therapeutic agent is rapamycin or a pharmaceutically acceptable salt or ester thereof. In some variations the therapeutic agent is rapamycin.

Described herein are methods wherein the amount of the therapeutic agent administered results in a concentration of the therapeutic agent in a tissue associated with the disease or condition of no greater than an amount equivalent to 41 ng/g, no greater than an amount equivalent to 11 ng/g rapamycin, or no greater than an amount equivalent to 7 ng/g of rapamycin.

Described herein are methods wherein the therapeutic agent is administered to the subject in need thereof at a dose of no greater than an amount equivalent to 2 mg/kg, 0.5 mg/kg, 0.27 mg/kg, 0.07 mg/kg, or 0.014 mg/kg of rapamycin.

Described herein are methods to treat a disease or condition. Described herein are methods to prevent a disease or condition.

Described herein are methods wherein the therapeutic agent is rapamycin, and the rapamycin is administered in a formulation containing about 2% w/w rapamycin, about 4% w/w ethanol, and about 94% w/w PEG 400.

DETAILED DESCRIPTION

Figure 1:
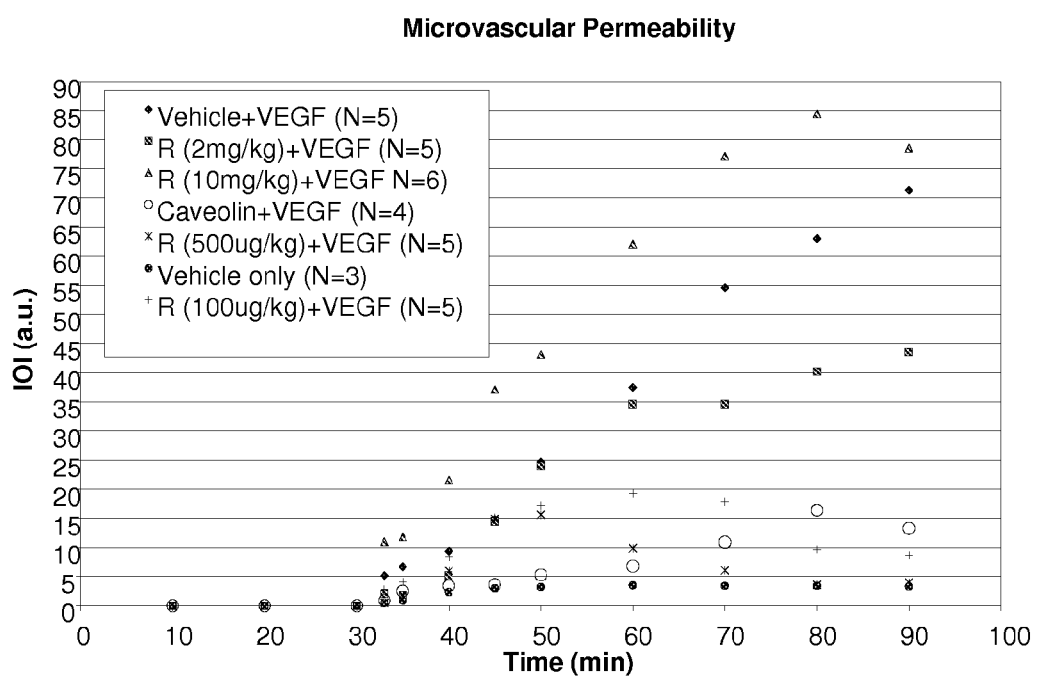
FIG. 1 depicts the vascular antipermeability effects of rapamycin in response to VEGF and various control treatments in a hamster cheek pouch model.

Described herein are formulations and methods relating to delivery of therapeutic agents to a subject, including but not limited to a human subject, and including but not limited to a therapeutic agent which is a limus compound, or a pharmaceutically acceptable prodrug, analog, salt, ester or derivative thereof. The formulations described herein may be used to treat, prevent, inhibit, delay onset of, or cause the regression of the vascular permeability-related diseases or conditions, including but not limited to the edema- or permeability-related diseases or conditions described herein. In some variations, the formulations and methods are used for the treatment of the aforementioned diseases or conditions.

Herein are described (1) the therapeutic agents that may be delivered to a subject, including but not limited to a human subject, (2) diseases and conditions that may be treated, prevented, inhibited, onset delayed, or regression caused by delivery of the therapeutic agents, (3) formulations that may be used to deliver the therapeutic agents, (4) methods of treatment, (5) doses and tissue levels, (6) routes of administration, (7) methods of preparation, and (8) extended delivery of therapeutic agents including but not limited to rapamycin.

Therapeutic Agents

Therapeutic agents that may be used include but are not limited to compounds that act by binding members of the immunophilin family of cellular proteins. Such compounds are known as "immunophilin binding compounds." Immunophilin binding compounds include but are not limited to the "limus" family of compounds. Examples of limus compounds that may be used include but are not limited to sirolimus (rapamycin) and its water soluble analog SDZ-RAD (Novartis), TAFA-93 (Isotechnika), tacrolimus, everolimus, RAD-001 (Novartis), pimecrolimus, temsirolimus, CCI-779 (Wyeth), AP23841 (Ariad), AP23573 (Ariad), and ABT-578 (Abbott Laboratories). Limus compound analogs and derivatives that may be used include but are not limited to the compounds described in U.S. Pat. Nos. 5,527,907; 6,376,517; and 6,329,386 and U.S. patent application Ser. No. 09/950,307, each of which is incorporated herein by reference in their entirety. Therapeutic agents also include analogs, prodrugs, salts, derivatives and esters of limus compounds.

In some variations the therapeutic agent is a limus compound. In some variations the therapeutic agent is an immunophilin binding compound. In some variations, the therapeutic agent is an mTOR inhibitor or an analog, derivative, salt, ester or prodrug thereof (e.g., TAFA93).

In some variations the therapeutic agent is a cyclophilin or an FK-506 binding protein (FKBP).

The terms rapamycin, rapa, and sirolimus are used interchangeably herein.

Other rapamycin derivatives that may be used include, without limitation, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, mono- and di-ester derivatives of rapamycin, 27-oximes of rapamycin; 42-oxo analog of rapamycin; bicyclic rapamycins; rapamycin dimers; silyl ethers of rapamycin; rapamycin arylsulfonates and sulfamates, mono-esters and di-esters at positions 31 and 42, 30-demethoxy rapamycin, and other derivatives described in Vezina et al., "Rapamycin (AY-22,989), A New Antifungal Antibiotic. I. Taxonomy Of The Producing Streptomycete And Isolation Of The Active Principle" J. Antibiot. (Tokyo) 28:721-726 (1975); Sehgal et al., "Rapamycin (AY-22,989), A New Antifungal Antibiotic. II. Fermentation, Isolation And Characterization" J. Antibiot. (Tokyo) 28:727-732 (1975); Sehgal et al., "Demethoxyrapamycin (AY-24, 668), A New Antifungal Antibiotic" J. Antibiot. (Tokyo) 36:351-354 (1983); and Paiva et al., "Incorporation Of Acetate, Propionate, And Methionine Into Rapamycin By *Streptomycetes hygroscopicus*" J Nat Prod 54:167-177 (1991), WO 92/05179, EP 467606, Caufield et al., "Hydrogenated Rapamycin Derivatives" U.S. Pat. No. 5,023,262; Kao et al., "Bicyclic Rapamycins" U.S. Pat. No. 5,120,725; Kao et al., "Rapamycin Dimers" U.S. Pat. No. 5,120,727; Failli et al., "Silyl Ethers Of Rapamycin" U.S. Pat. No. 5,120,842; Failli et al., "Rapamycin 42-Sulfonates And 42-(N-carboalkoxy) Sulfamates Useful As Immunosuppressive Agents" U.S. Pat. No. 5,177,203; Nicolaou et al., "Total Synthesis Of Rapamycin" J. Am. Chem. Soc. 115: 4419-4420 (1993); Romo et al, "Total Synthesis Of (−) Rapamycin Using An Evans-Tishchenko Fragment Coupling" J. Am. Chem. Soc. 115:7906-7907 (1993); and Hayward et al, "Total Synthesis Of Rapamycin Via A Novel Titanium-Mediated Aldol Macrocyclization Reaction" J. Am. Chem. Soc., 115:9345-9346 (1993), each of which is incorporated herein by reference in its entirety.

The limus family of compounds may be used in the formulations and methods for the treatment, prevention, inhibition, delaying the onset of, or causing the regression of the diseases and conditions described herein.

Other therapeutic agents that may be used include those disclosed in the following patents and publications, the contents of each of which is incorporated herein by reference in its entirety: PCT publication WO 2004/027027, published Apr. 1, 2004, titled Method of inhibiting choroidal neovascularization, assigned to Trustees of the University of Pennsylvania; U.S. Pat. No. 5,387,589, issued Feb. 7, 1995, titled Method of Treating Ocular Inflammation, with inventor Prassad Kulkarni, assigned to University of Louisville Research Foundation; U.S. Pat. No. 6,376,517, issued Apr. 23, 2003, titled Pipecolic acid derivatives for vision and memory disorders, assigned to GPI NIL Holdings, Inc; U.S. Pat. No. 5,100,899; U.S. Pat. No. 4,316,885, U.S. Pat. No. 4,650,803; US publication 2005/0032826, U.S. Pat. No. 6,890,546, and PCT publication WO 99/22722.

In some variations the formulation comprises a combination of one or more therapeutic agents.

The therapeutic agents may also be used in combination with other therapeutic agents and therapies, including but not limited to agents and therapies useful for the treatment, prevention, inhibition, delaying onset of, or causing regression of the diseases or conditions described herein.

Diseases or Conditions that May be Treated, Prevented, Inhibited, Onset Delayed, or Regression Caused Herein are described nonlimiting examples of diseases and conditions that may be treated, prevented, inhibited, onset delayed, or regression caused using the formulations and methods described herein. In some variations, the diseases or conditions are treated using one or more of the formulations or methods described herein. In some variations, the diseases or conditions are prevented using one or more of the formulations or methods described herein. In some variations, the diseases or conditions are inhibited using one or more of the formulations or methods described herein. In some variations, onset of the diseases or conditions is delayed using one or more of the formulations or methods described herein. In some variations, regression of the diseases or conditions is caused using one or more of the formulations or methods described herein. In some variations a disease or condition in a subject is treated, prevented, inhibited, onset delayed, or regression caused by administering to a subject in need thereof a formulation comprising a therapeutically effective amount of one or more therapeutic agents described herein. Unless the context indicates otherwise, the subjects on whom all of the methods of treatment may be performed include, but are not limited to, human subjects.

Generally, any vascular permeability related diseases or conditions susceptible to treatment, prevention, inhibition, delaying the onset of, or regression using the formulations and methods described herein may be treated, prevented, inhibited, onset delayed, or regression caused using the formulations and methods described herein. In some variations, the vascular permeability-related disease or condition is an ocular disease or condition.

Generally, any diseases or conditions relating to vasodilation susceptible to treatment, prevention, inhibition, delaying the onset of, or regression using the formulations and methods described herein may be treated, prevented, inhibited, onset delayed, or regression caused using the formulations and methods described herein. In some variations the diseases or conditions relating to vasodilation are permeability related diseases or conditions. In some variations, the vasodilation-related disease or condition is an ocular disease or condition.

In some variations, the vascular permeability related diseases or conditions are edema related diseases or conditions. In some variations, the edema related disease or condition is an ocular disease or condition.

In some variations, the formulations described herein are used to treat, prevent, inhibit, delay onset of, or cause regression of one or more of a vascular permeability-associated disease or disorder. In some variations, the formulations described herein are used to treat one or more of edema associated with capillary leak, diseases with edema as a complication, edema associated with endothelial cell dysfunction, edema associated with venous obstruction, edema associated with lymphatic obstruction, edema associated with pulmonary disease, edema associated with infectious conditions, edema associated with inflammatory, noninfectious, or autoimmune conditions, edema associated with neurologic conditions, edema associated with neoplasms or tumors (benign or malignant, solid or non-solid), diseases with dermatologic associations or findings, edema associated with genetic, congenital, or cystic abnormalities, edema due to environment, edema caused by injury, edema associated with infarction and ischemia reperfusion, miscellaneous causes of edema, or edema associated with systemic conditions. In some variations, the methods or formulations described herein are used to treat edema associated with neoplasms.

In some variations, the methods or formulations described herein are used to treat, prevent, inhibit, delay onset of, or cause regression of one or more diseases or conditions associated with edema correlated with capillary leak. In some variations the disease or condition associated with edema associated with capillary leak is any one or more of cardiomyopathy, dilated cardiomyopathy, hypertrophic cardiomyopathy, restrictive cardiomyopathy, congestive heart failure, filariasis, kidney failure, lymphedema, preeclampsia, eclampsia, thyroid condition, varicosity, or varicose veins. In some variations, the methods or formulations described herein are used to treat congestive heart failure.

In some variations, the methods or formulations described herein are used to treat, prevent, inhibit, delay onset of, or cause regression of one or more diseases or conditions associated with edema as a complication. In some variations the disease or condition associated with edema as a complication is any one or more of aortic coarctation, cor pulmonale, exudative dermatitis, Hodgkin's disease, pericarditis, or nephrogenic pulmonary edema.

In some variations, the methods or formulations described herein are used to treat, prevent, inhibit, delay onset of, or cause regression of one or more diseases or conditions associated with edema correlated with venous obstruction. In some variations the disease or condition associated with edema correlated with venous obstruction is any one or more of thrombophlebitis, thrombosis, neoplasm, varicosity, varicose veins, arteriovenous fistula, lymph node mass, or aneurysm.

In some variations, the methods or formulations described herein are used to treat, prevent, inhibit, delay onset of, or cause regression of one or more diseases or conditions associated with edema correlated with lymphatic obstruction. In some variations the disease or condition associated with edema correlated with lymphatic obstruction is filariasis, cellulitis, neoplasm, or surgical excision. In some variations, the methods or formulations described herein are used to treat cellulitis.

In some variations, the methods or formulations described herein are used to treat, prevent, inhibit, delay onset of, or cause regression of one or more diseases or conditions associated with edema correlated with pulmonary disease. In some variations the disease or condition associated with edema correlated with pulmonary disease is pulmonary edema, chronic obstructive pulmonary disease, pleural effusion, aspiration pneumonitis, asthma induced edema, or amniotic fluid embolism. In some variations, the methods or formulations described herein are used to treat pulmonary edema. In some variations, the methods or formulations described herein are used to treat asthma induced pulmonary edema.

In some variations, the methods or formulations described herein are used to treat, prevent, inhibit, delay onset of, or cause regression of one or more diseases or conditions associated with edema correlated with infectious diseases or conditions. In some variations the disease or condition associated with edema correlated with infectious diseases or conditions is boils, carbuncle, abscess, erysipelas, osteomyelitis, gas gangrene, erysipelas, anthrax, Ludwig's angina, parasitic infections, trichinosis, viral encephalitis, AIDS, herpes simplex virus infection, herpes zoster virus infection, tuberculosis (disseminated, military, etc.), neurosyphilis, prion diseases, meningitis, pneumococcal meningitis, rabies, neuroretinitis, anthrax exposure, or endotoxin induced edema. In some variations, the methods or formulations described herein are used to treat viral encephalitis. In some variations, the methods or formulations described herein are used to treat herpes simplex virus infection. In some variations, the methods or formulations described herein are used to treat herpes zoster virus infection. In some variations, the methods or formulations described herein are used to treat tuberculosis. In some variations, the methods or formulations described herein are used to treat neurosyphilis. In some variations, the methods or formulations described herein are used to treat neuroretinitis. In some variations, the methods or formulations described herein are used to treat endotoxin induced edema.

In some variations, the methods or formulations described herein are used to treat, prevent, inhibit, delay onset of, or cause regression of one or more diseases or conditions associated with edema correlated with inflammatory, noninfectious, or autoimmune diseases or conditions. In some variations the disease or condition associated with edema correlated with inflammatory, noninfectious, or autoimmune diseases or conditions is Wegeners granulomatosis, Sjogren's syndrome, scleroderma, systemic Lupus erythematosis, sarcoidosis, multiple sclerosis, Reiter's syndrome, Pyogenic granuloma, vasculitis, or demyelinating diseases. In some variations, the methods or formulations described herein are used to treat Reiter's syndrome. In some variations, the methods or formulations described herein are used to treat Pyogenic granuloma. In some variations, the methods or formulations described herein are used to treat systemic Lupus erythematosis. In some variations, the methods or formulations described herein are used to treat scleroderma. In some variations, the methods or formulations described herein are used to treat sarcoidosis. In some variations, the methods or formulations described herein are used to treat Wegeners granulomatosis. In some variations, the methods or formulations described herein are used to treat Sjogren's syndrome. In some variations, the methods or formulations described herein are used to treat multiple sclerosis. In some variations, the methods or formulations described herein are used to treat vasculitis. In some variations, the methods or formulations described herein are used to treat demyelinating disease. In some variations, the methods or formulations described herein are used to treat toxic metabolic brain edema. In some variations, the methods or formulations described herein are used to treat arthritis. In some variations, the arthritis is rheumatoid arthritis. In some variations, the arthritis is osteoarthritis. In some variations, the methods or formulations described herein are used to treat carpel tunnel syndrome.

In some variations, the methods or formulations described herein are used to treat, prevent, inhibit, delay onset of, or cause regression of one or more diseases or conditions associated with edema correlated with a neurological disease or condition. In some variations the disease or condition associated with edema correlated with a neurological disease or condition is benign intracranial hypertension, papilledema, optic neuritis, multi-infarct dementia, Alzheimers disease, amyloid deposition diseases, toxic metabolic brain edema, cerebral amyloid angiopathy (also known as congophilic angiopathy or cerebrovascular amyloidosis), post-ictal state, blood brain barrier dysfunction, Vogt-Koyanagi-Harada syndrome, prophylactic use in carotid endarterectomy, or vasogenic brain edema. In some variations, the methods or formulations described herein are used to treat papilledema. In some variations, the methods or formulations described herein are used to treat optic neuritis. In some variations, the methods or formulations described herein are used to treat amyloid deposition diseases. In some variations, the methods or formulations described herein are used to treat Vogt-Koyanagi-Harada syndrome.

In some variations, the methods or formulations described herein are used to treat, prevent, inhibit, delay onset of, or cause regression of one or more diseases or conditions associated with edema correlated with a solid or non-solid, benign or malignant, neoplasm or tumor. In some variations the disease or condition associated with edema correlated with a solid or non-solid, benign or malignant, neoplasm or tumor is choroidal melanoma, choroidal nevus, melanoma, neuroma, epithelioma, lymphangioma, myxoma, fibroma, fibromyoma, osteoma, chondroma, angioma, angiosarcoma, peritumoral brain edema, hemangiomas, carcinoid, or multiple endocrine neoplasia. In some variations, the methods or formulations described herein are used to treat choroidal melanoma. In some variations, the methods or formulations described herein are used to treat choroidal nevus. In some variations, the methods or formulations described herein are used to treat melanoma. In some variations, the methods or formulations described herein are used to treat neuroma. In some variations, the methods or formulations described herein are used to treat epithelioma. In some variations, the methods or formulations described herein are used to treat lymphangioma. In some variations, the methods or formulations described herein are used to treat myxoma. In some variations, the methods or formulations described herein are used to treat fibroma. In some variations, the methods or formulations described herein are used to treat fibromyoma. In some variations, the methods or formulations described herein are used to treat osteoma. In some variations, the methods or formulations described herein are used to treat chondroma. In some variations, the methods or formulations described herein are used to treat hemangioma. In some variations, the methods or formulations described herein are used to treat hemangioblastoma.

In some variations, the methods or formulations described herein are used to treat, prevent, inhibit, delay onset of, or cause regression of one or more diseases or conditions associated with a dermatological disease or disorder. In some variations the disease or condition associated with edema correlated with a dermatological disease or disorder is porphyria cutanea tarda, pemphigoid, dermatitis herpetiformis, pemphigous, empitigo, erythema multiforme, exudative dermatitis, epidermolysis bullosa, contact dermatitis, actinic dermatitis, toxic erythema, dermatomyositis, eczema, or toxic epidermal necrolysis. In some variations, the methods or formulations described herein are used to treat dermatitis. In some variations, the methods or formulations described herein are used to treat pemphigous. In some variations, the methods or formulations described herein are used to treat erythema multiforme.

In some variations, the methods or formulations described herein are used to treat, prevent, inhibit, delay onset of, or cause regression of one or more diseases or conditions associated with a genetic, congenital, or cystic abnormality. In some variations the disease or condition associated with edema correlated with a genetic, congenital, or cystic abnormality is xeroderma pigmentosa, hydrocoele, dermoid cyst, ovarian cyst, amniotic band, arteriovenous fistula, meningocoele, hydrocephalus, hereditary angioneurotic edema, neurofibromatosis, Von Hippel Lindau disease, or tuberous sclerosis. In some variations, the methods or formulations described herein are used to treat neurofibromatosis. In some variations, the methods or formulations described herein are used to treat Von Hippel Lindau disease. In some variations, the methods or formulations described herein are used to treat tuberous sclerosis.

In some variations, the methods or formulations described herein are used to treat, prevent, inhibit, delay onset of, or cause regression of one or more diseases or conditions associated with increased capillary permeability. In some variations the disease or condition associated with edema correlated with increased capillary permeability is acute nephritis, angioneurotic edema, scleroderma, hypersensitivity reactions, or transfusion reactions. In some variations, the methods or formulations described herein are used to treat hypersensitivity reactions. In some variations, the methods or formulations described herein are used to treat angioneurotic edema.

In some variations, the methods or formulations described herein are used to treat, prevent, inhibit, delay onset of, or cause regression of one or more diseases or conditions associated with edema correlated with an environmental or other exposure. In some variations the disease or condition associated with edema correlated with an environmental or other exposure is acute mountain sickness, high altitude pulmonary edema (HAPE), high altitude cerebral edema (HACE), tropical edema, chilblains, drug toxicity, poisonings, anoxia (by way of nonlimiting example, smoke inhalation, carbon monoxide poisoning, near drowning, etc.), exposure to noxious gases, poison ivy, poison oak, poison sumac, or nettles exposure, cholinergic intoxication, edema from systemic steroid therapy, ethanol induced brain injury, or hyponatremic brain edema. In some variations, the methods or formulations described herein are used to treat drug toxicity. In some variations, the methods or formulations described herein are used to treat high altitude pulmonary edema (HAPE). In some variations, the methods or formulations described herein are used to treat high altitude cerebral edema (HACE). In some variations, the methods or formulations described herein are used to treat pulmonary edema associated with anoxia. In some variations, the methods or formulations described herein are used to treat pulmonary edema associated with smoke inhalation. In some variations, the methods or formulations described herein are used to treat hyponatremic brain edema.

In some variations, the methods or formulations described herein are used to treat, prevent, inhibit, delay onset of, or cause regression of one or more diseases or conditions associated with edema correlated with trauma or injury. In some variations the disease or condition associated with edema correlated with trauma or injury is acute trauma (by way of non limiting example from bone, joint, soft tissue, or organ injury), prophylactic to prevent swelling in athletics or sporting activities, bruise, contusion, ligamentous sprain or tendonous strain, bursitis, joint injuries, fracture, insect bite, snake bite, marine intoxications or envenomations (by way of nonlimiting example from sponges, corals, sea anemones, sea urchins, sting ray, scorpion fish, jelly fish stings, etc.), exposure to an irritant or corrosive, frostbite, burn, sunburn, electrical injury, traumatic brain injury, spinal cord injury, traumatic optic neuropathy, subdural hematoma, subarachnoid hematoma, or carotid cavernous fistula. In some variations, the methods or formulations described herein are used to treat acute trauma. In some variations, the methods or formulations described herein are used to treat edema secondary to bites or stings. In some variations, the methods or formulations described herein are used to treat edema associated with blunt trauma. In some variations, the methods or formulations described herein are used to treat insect bite. In some variations, the methods or formulations described herein can be used to treat snake bites. In some variations, the methods or formulations described herein are used to treat burn. In some variations, the methods or formulations described herein are used to treat traumatic optic neuropathy. In some variations, the methods or formulations described herein are used to treat carotid cavernous fistula.

In some variations, the methods or formulations described herein are used to treat, prevent, inhibit, delay onset of, or cause regression of one or more diseases or conditions associated with edema correlated with infarction or ischemia reperfusion. In some variations the disease or condition associated with edema correlated with infarction or ischemia reperfusion is stroke, myocardial infarction, arterial obstruction, arterial laceration, extremity amputation requiring replantation, central retinal artery occlusion, branch retinal artery occlusion, anterior or posterior ischemic optic neuropathy, or ischemia induced edema. In some variations, the methods or formulations described herein are used to treat central retinal artery occlusion. In some variations, the methods or formulations described herein are used to treat branch retinal artery occlusion. In some variations, the methods or formulations described herein are used to treat anterior or posterior ischemic optic neuropathy. In some variations, the methods or formulations described herein are used to treat ischemia induced edema.

In some variations, the methods or formulations described herein are used to treat, prevent, inhibit, delay onset of, or cause regression of one or more diseases or conditions associated with edema due to one or more miscellaneous causes. In some variations the disease or condition associated with edema due to one or more miscellaneous causes is gout, angioneurotic edema, Milroy's disease, corneal edema, episceritis, scleritis, choroidal effusion, conjunctival edema, exudative retinal detachment, ventriculoperitoneal shunt malfunction, CSF drainage obstruction, aphthous ulcer, leukoplakia, epiglotitis, cytotoxic edema, laryngeal edema, chronic cough, lichen planus, pancreatitis, blepharitis, eyelid swelling, or polymyositis. In some variations, the methods or formulations described herein are used to treat eyelid edema. In some variations, the methods or formulations described herein are used to treat corneal edema. In some variations, the corneal edema is chronic corneal edema. In some variations, the methods or formulations described herein are used to treat episceritis. In some variations, the methods or formulations described herein are used to treat scleritis. In some variations, the methods or formulations described herein are used to treat choroidal effusion. In some variations, the methods or formulations described herein are used to treat conjunctival edema. In some variations, the methods or formulations described herein are used to treat exudative retinal detachment. In some variations, the methods or formulations described herein are used to treat ventriculoperitoneal shunt malfunction. In some variations, the methods or formulations described herein are used to treat blepharitis. In some variations, the methods or formulations described herein are used to treat eyelid swelling. In some variations, the methods or formulations described herein are used to treat CSF drainage obstruction.

In some variations, the methods or formulations described herein are used to treat, prevent, inhibit, delay onset of, or cause regression of one or more diseases or conditions associated with edema due to one or more systemic diseases or conditions. In some variations the disease or condition associated with edema due to one or more systemic diseases or conditions is anaphylactic shock, shock, sepsis, acute respiratory distress syndrome (ARDS), intensive care patient, heart lung bypass induced brain edema, cold induced brain edema, or hepatic failure induced brain edema. In some variations, the methods or formulations described herein are used to treat acute respiratory distress syndrome (ARDS). In some variations, the methods or formulations described herein are used to treat brain edema following stroke. In some variations, the methods or formulations described herein are used to treat brain edema following closed head injury.

In some variations, the methods or formulations described herein are used to treat, prevent, inhibit, delay onset of, or cause regression of influenza. In some variations, the influenza is bird flu. In some variations, the influenza is influenza A, influenza B, or influenza C. In some variations, the influenza is influenza A (H3), influenza A (H1), influenza A (H1N2), influenza A (H3N2), influenza A/Panama/2007/99 (H3N2), influenza A/Fujian/411/2002 (H3N2), or influenza A (H5N1).

In some variations, the methods or formulations described herein are used to treat, prevent, inhibit, delay onset of, or cause regression of macular edema. In some variations, the macular edema is diabetic macular edema. In some variations, the macular edema is macular edema from vein occlusion.

In some variations, the methods or formulations described herein are used to treat, prevent, inhibit, delay onset of, or cause regression of cystoid macular edema.

In some variations, the methods or formulations described herein are used to treat, prevent, inhibit, delay onset of, or cause regression of retinal artery occlusion. In some variations, the methods or formulations described herein are used to treat, prevent, inhibit, delay onset of, or cause regression of retinal vein occlusion.

In some variations, the methods or formulations described herein are used to treat, prevent, inhibit, delay onset of, or cause regression of central retinal artery occlusion. In some variations, the methods or formulations described herein are used to treat, prevent, inhibit, delay onset of, or cause regression of central retinal vein occlusion.

In some variations, the methods or formulations described herein are used to treat, prevent, inhibit, delay onset of, or cause regression of branch retinal artery occlusion. In some variations, the methods or formulations described herein are used to treat, prevent, inhibit, delay onset of, or cause regression of branch retinal vein occlusion.

In some variations, the methods or formulations described herein are used to treat, prevent, inhibit, delay onset of, or cause regression of exudative retinal detachment.

In some variations, the methods or formulations described herein are used to treat, prevent, inhibit, delay onset of, or cause regression of retinal edema associated with choroidal neovascularization.

In some variations, the methods or formulations described herein are used to treat, prevent, inhibit, delay onset of, or cause regression of choroidal effusion.

In some variations, the methods or formulations described herein are used to treat, prevent, inhibit, delay onset of, or cause regression of sympathetic ophthalmia, sarcoma, high altitude retinal hemorrhages, blunt and penetrating ocular and orbital trauma, hypertensive retinopathy, macular star, orbital cellulitis, choroidal infarction, frosted branch angiitis, sickle cell disease, papillomas, keratitis, dacryoadenitis, canaliculitis, dacryocystitis, contact lens induced conjunctivitis, interstitial keratitis, ligneous conjunctivitis, pinguecula, pterygium, cornea gutata, adenomas, capillary hemangioma, cavernous hemangioma, hemangioendothelioma, hemangiopericytoma, kaposi's sarcoma, choristoma, benign reactive lymphoid hyperplasia, lymphoid neoplasia, hordeolum, chalazion, xanthomatous tumors, corneal graft edema, corneal edema associated with refractive procedures, and ptosis.

In some variations, the methods or formulations described herein are used to treat, prevent, inhibit, delay onset of, or cause regression of age-related macular degeneration (e.g., wet age-related macular degeneration or dry to wet age-related macular degeneration), diabetic retinopathy, retinopathy of prematurity, central retinal vein occlusion, branch retinal vein occlusion, or uveitis.

In some variations, the methods or formulations described herein are used to treat, prevent, inhibit, delay onset of, or cause regression of macular edema (e.g., diabetic macular edema, cystoid macular edema, or macular edema from vein occlusion), retinal edema (e.g., retinal edema associated with choroidal neovascularization), influenza including bird flu, congestive heart failure, pulmonary edema, ARDS, asthma induced pulmonary edema, viral encephalitis, neuroretinitis, endotoxin induced edema, vasculitis, toxic metabolic brain edema, Vogt-Koyanagi-Harada disease, hemangiomas, hemangioblastoma, pemphigous; von Hippel Lindau disease, tuberous sclerosis, angioneurotic edema, snake bite, high altitude cerebral edema (HACE), high altitude pulmonary edema (HAPE), pulmonary edema associated with smoke inhalation, pulmonary edema associated with anoxia, hyponatremic brain edema, edema associated with blunt trauma, edema secondary to bites or stings, brain edema following stroke or closed head injury, exudative retinal detachment, corneal edema (e.g. chronic corneal edema), or scleritis.

In some variations, the methods or formulations described herein are used to treat, prevent, inhibit, delay onset of, or cause regression of cystoid macular edema, retinal edema (e.g., retinal edema associated with choroidal neovascularization), influenza including bird flu, viral encephalitis, neuroretinitis, endotoxin induced edema, vasculitis, toxic metabolic brain edema, hemangioma, angioneurotic edema, snake bite, high altitude cerebral edema (HACE), high altitude pulmonary edema (HAPE), hyponatremic brain edema, edema associated with blunt trauma, brain edema following stroke or closed head injury, or corneal edema (e.g. chronic corneal edema).

In some variations, the methods or formulations described herein are used to treat, prevent, inhibit, delay onset of, or cause regression of macular edema, retinal edema, Vogt-Koyanagi-Harada disease, von Hippel Lindau disease, retinal detachment (e.g., exudative retinal detachment) or corneal edema (e.g. chronic corneal edema).

In some variations, the methods or formulations described herein are used to treat, prevent, inhibit, delay onset of, or cause regression of hypotension due to peripheral vasodilation. In some variations, the methods or formulations described herein are used to treat, prevent, inhibit, delay onset of, or cause regression of aortic stenosis. In some variations, the methods or formulations described herein are used to treat a disease or disorder which is detrimental to a subject with aortic stenosis. In some variations, the methods or formulations described herein are used to treat a permeability-related disease or disorder which is detrimental to a subject with aortic stenosis.

In some variations any one or more of the formulations described herein comprising any one or more of the therapeutic agents described herein are used to treat, prevent, inhibit, delay onset of, or cause regression of any vascular permeability related disease or disorder, including but not limited to those vascular permeability related diseases or disorders described herein.

In some variations any one or more of the formulations described herein comprising any one or more of the therapeutic agents described herein are used to treat, prevent, inhibit, delay onset of, or cause regression of any vasodilation related disease or disorder, including but not limited to those vascular permeability related diseases or disorders described herein.

In some variations any one or more of the formulations described in U.S. 60/772,018, titled STABLE FORMULATIONS AND METHODS OF THEIR PREPARATION AND USE; U.S. Ser. No. 11/386,290, titled DRUG DELIVERY SYSTEMS FOR TREATMENT OF DISEASES OR CONDITIONS; U.S. Ser. No. 11/351,844, titled FORMULATIONS FOR OCULAR TREATMENT; U.S. Ser. No. 11/351,761, titled LIQUID FORMULATIONS FOR TREATMENT OF DISEASES OR CONDITIONS; U.S. Ser. No. 11/386,290, titled DRUG DELIVERY SYSTEMS FOR TREATMENT OF DISEASES OR CONDITIONS; and US 2005/0064010 are used to treat, prevent, inhibit, delay onset of, or cause regression of any vascular permeability related disease or disorder, including but not limited to those vascular permeability related diseases or disorders described herein.

In some variations any one or more of the therapeutic agents described herein are used to treat, prevent, inhibit, delay onset of, or cause regression of any vascular permeability related disease or disorder, excepting those vascular permeability related diseases or disorders described in PCT publication WO 04/027027, U.S. Pat. No. 6,376,517, US publication number 2005/0064010, or U.S. Pat. No. 5,387,589, the contents of each of which is hereby incorporated by reference in its entirety.

In some variations any of the therapeutic agents described herein are used to treat, prevent, inhibit, delay onset of, or cause regression of any vascular permeability related disease or disorder, excepting those vascular permeability related diseases or disorders described in PCT publication WO 04/027027, U.S. Pat. No. 6,376,517, or U.S. Pat. No. 5,387,589.

In some variations, any one or more of the therapeutic agents or formulations described herein are used to treat, prevent, inhibit, delay onset of, or cause regression of any one or more of cardiomyopathy, dilated cardiomyopathy, hypertrophic cardiomyopathy, restrictive cardiomyopathy, congestive heart failure, filariasis, kidney failure, lymphedema, preeclampsia, eclampsia, thyroid condition, varicosity, varicose veins, aortic coarcation, cor pulmonale, exudative dermatitis, Hodgkin's disease, pericarditis, nephrogenic pulmonary edema, varicosity, arteriovenous fistula, lymph node mass, aneurysm, filariasis, neoplasm, surgical excision, pulmonary edema, chronic obstructive pulmonary disease, pleural effusion, aspiration pneumonitis, asthma induced edema, amniotic fluid embolism, boils, carbuncle, abscess, erysipelas, osteomyelitis, gas gangrene, erysipelas, anthrax, Ludwig's angina, parasitic infections, trichinosis, viral encephalitis, AIDS, herpes simplex virus infection, prion diseases, rabies, neuroretinitis, anthrax exposure, endotoxin induced edema, Wegeners granulomatosis, Sjogren's syndrome, scleroderma, systemic Lupus erythematosis, multiple sclerosis, Pyogenic granuloma, vasculitis, demyelinating diseases, benign intracranial hypertension, multi-infarct dementia, Alzheimers disease, amyloid deposition diseases, toxic metabolic brain edema, cerebral amyloid angiopathy, post-ictal state, blood brain barrier dysfunction, prophylactic use in carotid endarterectomy, vasogenic brain edema, choroidal nevus, neuroma, epithelioma, lymphangioma, myxoma, fibroma, fibromyoma, osteoma, chondroma, angioma, angiosarcoma, peritumoral brain edema, hemangiomas, carcinoid, multiple endocrine neoplasia, porphyria cutanea tarda, pemphigoid, dermatitis herpetiformis, pemphigous, empitigo, erythema multiforme, exudative dermatitis, epidermolysis bullosa, contact dermatitis, actinic dermatitis, toxic erythema, dermatomyositis, eczema, toxic epidermal necrolysis, xeroderma pigmentosa, hydrocoele, dermoid cyst, ovarian cyst, amniotic band, arteriovenous fistula, meningocoele, hydrocephalus, hereditary angioneurotic edema, neurofibromatosis, Von Hippel Lindau disease, tuberous sclerosis, acute nephritis, angioneurotic edema, scleroderma, hypersensitivity reactions, transfusion reactions, acute mountain sickness, high altitude pulmonary edema (HAPE), high altitude cerebral edema (HACE), tropical edema, chilblains, drug toxicity, poisonings, anoxia due to smoke inhalation, carbon monoxide poisoning, or near drowning, exposure to noxious gases, poison ivy, poison oak, poison sumac, or nettles exposure, cholinergic intoxication, edema from systemic steroid therapy, ethanol induced brain injury, hyponatremic brain edema, acute trauma from bone, joint, soft tissue, or organ injury, prophylactic treatment to prevent swelling in athletics or sporting activities, ligamentous sprain or tendonous strain, bursitis, joint injuries, fracture, insect bite, snake bite, marine intoxications or envenomations due to sponges, corals, sea anemones, sea urchins, sting ray, scorpion fish, or jelly fish stings, frostbite, electrical injury, traumatic brain injury, spinal cord injury, traumatic optic neuropathy, subdural hematoma, subarachnoid hematoma, carotid cavernous fistula, stroke, myocardial infarction, arterial obstruction, arterial laceration, extremity amputation requiring replantation, gout, angioneurotic edema, Milroy's disease, corneal edema, choroidal effusion, conjunctival edema, ventriculoperitoneal shunt malfunction, CSF drainage obstruction, aphthous ulcer, leukoplakia, epiglotitis, cytotoxic edema, laryngeal edema, chronic cough, lichen planus, pancreatitis, polymyositis, anaphylactic shock, shock, sepsis, acute respiratory distress syndrome (ARDS), intensive care patient, heart lung bypass induced brain edema, cold induced brain edema, hepatic failure induced brain edema, high altitude retinal hemorrhages, macular star, choroidal infarction, frosted branch angiitis, papillomas, dacryoadenitis, canaliculitis, cornea gutata, adenomas, capillary hemangioma, cavernous hemangioma, hemangioendothelioma, hemangiopericytoma, choristoma, benign reactive lymphoid hyperplasia, lymphoid neoplasia, corneal graft edema, corneal edema associated with refractive procedures, arthritis (e.g., rheumatoid arthritis or osteoarthritis), and carpel tunnel syndrome.

Formulations

Most generally, the formulations described herein comprise any one or more of the therapeutic agents described herein and may generally be of any type that is capable of delivering the therapeutic agent for treating, preventing, inhibiting, delaying onset of, or causing regression of one or more of the diseases or conditions described herein. In some variations the therapeutic agent is a limus compound, or a pharmaceutically acceptable prodrug, analog, salt, ester or derivative thereof.

In some variations any of the formulations described herein are administered in multiple locations within a period of time, including without limitation within an hour of one another. Without being bound by theory, it is thought that such multiple administrations, including but not limited to multiple injections, allow for a greater total dose to be administered to the tissue than a single dose due to a potentially limited ability of the local tissue to absorb the larger volume or amount. In some variations any of the formulations described herein are administered at one or more times.

In some variations the formulation is a solid formulation, a liquid formulation, a drug delivery system, or a formulation associated, delivered by, or administered proximate to a device.

In some variations, the formulation is a nanoparticle formulation. In some variations, the nanoparticle formulation is made by milling.

In some variations the formulation is a stable formulation of rapamycin prepared or preparable by a method described in U.S. 60/772,018, filed Feb. 9, 2006, titled STABLE FORMULATIONS AND METHODS OF THEIR PREPARATION AND USE.

Solid Formulations

In some variations the formulations described herein are solid formulations. The solid formulations may be formulated for various routes of administration, including but not limited to delivery by any route of administration described herein, including but not limited to by implantation or oral delivery. Nonlimiting examples of solid dosage forms include controlled or sustained release formulations, coated or uncoated solid formulations, wafers, films, particles, microparticles, nanoparticles, beads, diffusion-based formulations, degradation-based formulations, formulations with a reservoir, chewable formulations, rapidly disintegrating formulations, buccal formulations, and polymer-based formulations.

In some variations, the therapeutic agent is administered as a solid formulation, including but not limited to solid a formulation consisting essentially of pure drug (e.g., about 99% w/w).

Non-limiting examples of solid drug delivery systems that may be used in the methods described herein are found in U.S. 60/664,119, titled DRUG DELIVERY SYSTEMS FOR TREATMENT OF DISEASES OR CONDITIONS and U.S. Ser. No. 11/386,290, titled DRUG DELIVERY SYSTEMS FOR TREATMENT OF DISEASES OR CONDITIONS, each of which is incorporated herein by reference in its entirety.

Liquid Formulations

In some variations the formulations described herein are liquid formulations. The liquid formulations described herein contain a therapeutic agent and may generally be any liquid formulation, including but not limited to solutions, suspensions, and emulsions.

One liquid formulation described herein is an in situ gelling formulation. In situ gelling formulations, as described herein, comprise a therapeutic agent and a plurality of polymers which give a formulation that forms a gel or a gel-like substance when placed in an aqueous medium, including but not limited to an aqueous medium of the eye.

In some variations of the liquid formulations described herein, the therapeutic agent is a solution or suspension of rapamycin in a liquid medium. Liquid media include but are not limited to solvents, including but not limited to those in the Solubilization of Therapeutic Agents section.

The liquid formulations described herein may comprise a solubilizing agent component. In some variations the solubilizing agent component is a surfactant. Note that there is some overlap between components that may be solvents and solubilizing agents, and therefore the same component may in some systems be used as either a solvent or a solubilizing agent. A liquid formulation that comprises a therapeutic agent and a component that may be considered either a solvent or a solubilizing agent or surfactant will be considered a solvent if it is playing the role of a solvent; if the component is not playing the role of the solvent, the component may be considered a solubilizing agent or surfactant.

Liquid formulations may optionally further comprise stabilizers, excipients, gelling agents, adjuvants, antioxidants, and/or other components as described herein.

In some variations all components in the liquid formulation, other than the therapeutic agent, are liquid at room temperature.

In some variations, the liquid formulation comprises nanoparticles. In some variations, the nanoparticles are made by milling.

In some variations, the liquid formulation comprises a release modifying agent. In some variations, the release modifying agent is a film-forming polymer component. The film-forming polymer component may comprise one or more film-forming polymers. Any film-forming polymer may be used in the excipient component. In some variations, the film-forming polymer component comprises a water insoluble film forming polymer. In some variations, the release modifying agent component comprises an acrylic polymer, including but not limited to polymethacrylate, including but not limited to Eudragit RL.

Described herein are compositions and liquid formulations for delivery of the therapeutic agents described in the Therapeutic Agents section. Delivery of therapeutic agents using the compositions and liquid formulations described herein may be used to treat, prevent, inhibit, delay the onset of, or cause the regression of the diseases and conditions described in the Diseases and Conditions section. The compositions and liquid formulations described herein may comprise any of the therapeutic agents described in the Therapeutic Agents section, including but not limited to rapamycin. The compositions and liquid formulations described herein may comprise one or more than one therapeutic agent. Other compositions and liquid formulations in addition to those explicitly described herein may be used.

When the therapeutic agent is rapamycin, the formulations may be used to maintain an amount of a therapeutic agent described herein, including but not limited to a limus compound such as rapamycin that is effective to treat one or more of the diseases or conditions described herein.

In some variations the therapeutic agent in the formulation comprises between 0.01 to 80% of the total weight of the composition; between 0.05 to 15%; between 0.1 to 10%; between 1 to 5%; or between 5 to 15%; between 8 to 10%; between about 0.01 to about 1%; between 0.05 to 5%; between 0.1 to 0.2%; between 0.2 to 0.3%; between 0.3 to 0.4%; between 0.4 to 0.5%; between 0.5 to 0.6%; between 0.6 to 0.7%; between 0.7 to 1%; between 1 to 5%; between 5 to 10%; between 5 to 30%; between 15 to 55%, between 20 to 30%; between 25 to 30%, between 35 to 55%; about 10%; about 20%, about 30%, about 35%, about 40%; about 45%; about 50%; about 55%, about 60%, about 65%; about 70%, about 75%; or about 80% w/w.

The solvent component may comprise, for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%.

The solubilizing agent component may comprise, for instance, between about 0.01 to about 30% of the total weight of the composition; between about 0.1 to about 20%; between about 2.5 to about 15%; between about 10 to about 15%; or between about 5 to about 10%; between about 8 to about 12%; between about 10 to about 20%; between about 20 to about 30%.

In some variations, the liquid formulations described herein have a viscosity of between 40% and 120% centipoise. In some variations the liquid formulations described herein have a viscosity of between 60% and 80% centipoise.

In some variations the liquid formulations described herein comprise a therapeutic agent and a solvent component. The solvent component may comprise a single solvent or a combination of solvents. The therapeutic agent component may comprise a single therapeutic agent or a combination of therapeutic agents. In some variations, the solvent is glycerin, dimethylsulfoxide, N-methylpyrrolidone, dimethyl acetamide (DMA), dimethyl formamide, glycerol formal, ethoxy diglycol, triethylene glycol dimethyl ether, triacetin, diacetin, corn oil, acetyl triethyl citrate (ATC), ethyl lactate, polyglycolated capryl glyceride, γ butyrolactone, dimethyl isosorbide, benzyl alcohol, ethanol, isopropyl alcohol, polyethylene glycol of various molecular weights, including but not limited to PEG 300 and PEG 400, or propylene glycol, or a mixture of one or more thereof.

In some variations the liquid formulations described herein are solutions, and comprise a therapeutic agent and a solvent component. In some variations the solvent component comprises ethanol. In some variations the solvent component comprises ethanol and a polyethylene glycol, including but not limited to a liquid polyethylene glycol, including but not limited to one or more of PEG 300 or PEG 400.

In some variations, the liquid formulations described herein are suspensions, and comprise a therapeutic agent and a diluent component. In some variations, the diluent component comprises one or more components listed herein as solvents or solubilizing agents, wherein the resulting mixture is a suspension.

In some variations the liquid formulation is partly a solution and partly a suspension.

In some variations the liquid formulation is an in situ gelling formulation, and comprises a therapeutic agent and a polymer component, wherein the polymer component may comprise a plurality of polymers. In some variations, the liquid formulation comprises a polymethacrylate polymer. In some variations, the liquid formulation comprises a polyvinylpyrrolidone polymer.

Some variations of liquid formulations include one or more therapeutic agent or agents such as but not limited to rapamycin between about 0.01% and about 20% by weight of the total, a solvent between about 5% and about 15% by weight of the total, a solubilizing agent including but not limited to a surfactant between about 5% and about 15% by weight of the total, with water as the primary remaining component. In some variations the formulations further comprise stabilizing agents, excipients, adjuvants, or antioxidants, between about 0 and about 40% by weight of the total.

In some variations, a liquid formulation comprises up to about 5% therapeutic agent, including but not limited to rapamycin, per weight of the total; and up to about 99.9% of a solvent component, by weight of the total. In some variations the liquid formulation comprises up to about 5% therapeutic agent, including but not limited to rapamycin, per weight of the total; and up to about 99.9% of a diluent component.

In some variations, a liquid formulation may comprise up to about 5% therapeutic agent, including but not limited to rapamycin, per weight of the total; up to about 10% solvent by weight of the total; and up to about 85% of a solubilizing component, by weight of the total. In some variations the solubilizing component is an aqueous solution of a surfactant.

A plurality of polymers component may comprise, for instance, between about 0.01 to about 30% of the total weight of the composition; between about 0.1 to about 20%; between about 2.5 to about 15%; between about 10 to about 15%; between about 3 to about 5%; between about 5 to about 10%; between about 8 to about 12%; between about 10 to about 20%; or between about 20 to about 30%.

Some variations of liquid formulations includes a therapeutic agent or agents such as but not limited to rapamycin between about 0.01% and about 20% by weight of the total, a solvent component between about 60% and about 98% by weight of the total, and a plurality of polymers, whose combined percentage is between about 0.1% and about 15% by weight of the total. In some variations the formulations further comprise stabilizing agents, excipients, adjuvants, or antioxidants, between about 0 and about 40% by weight of the total.

In some variations, a liquid formulation may comprise about 4% therapeutic agent, including but not limited to rapamycin, per weight of the total; about 91% solvent by weight of the total; and about 5% polymeric component, per weight of the total.

The following references, each of which is incorporated herein by reference in its entirety, show one or more formulations, including but not limited to rapamycin formulations, and which describe use of rapamycin at various doses and other therapeutic agents for treating various diseases or conditions: U.S. 60/651,790, titled FORMULATIONS FOR OCULAR TREATMENT; U.S. 60/664,040, titled LIQUID FORMULATIONS FOR TREATMENT OF DISEASES OR CONDITIONS; U.S. 60/664,119, titled DRUG DELIVERY SYSTEMS FOR TREATMENT OF DISEASES OR CONDITIONS; U.S. 60/664,306, titled IN SITU GELLING FORMULATIONS AND LIQUID FORMULATIONS FOR TREATMENT OF DISEASES OR CONDITIONS; U.S. Ser. No. 11/351,844, titled FORMULATIONS FOR OCULAR TREATMENT; U.S. Ser. No. 11/351,761, titled LIQUID FORMULATIONS FOR TREATMENT OF DISEASES OR CONDITIONS; U.S. Ser. No. 11/386,290, titled DRUG DELIVERY SYSTEMS FOR TREATMENT OF DISEASES OR CONDITIONS; U.S. 60/772,018, titled STABLE FORMULATIONS, AND METHODS OF THEIR PREPARATION AND USE; US 2005/0187241; and US 2005/0064010.

In some variations, the liquid formulation comprises a therapeutic agent or agents with a concentration of between about 0.01% and about 10% by weight of the total, and a solvent between about 10% and about 99% by weight of the total. In some variations the formulation further comprises a solubilizing agent including but not limited to a surfactant. In some variations the liquid formulation further comprises a stabilizing agent, excipient, adjuvant, or antioxidant, etc., between about 0 and about 40% by weight of the total. In some variations, the therapeutic agent is about 5% by weight of the total, and the solvent component is about 95% by weight of the total.

In some variations the rapamycin in the liquid formulation contains between about 0.01 to about 10% of the total weight of the composition; between about 0.05 to about 10%; between about 0.1 to about 5%; between about 1 to about 5%; or between about 5 to about 15%; between about 8 to about 10%; between about 0.01 to about 1%; between about 0.05 to about 5%; between about 0.1 to about 0.2%; between about 0.2 to about 0.3%; between about 0.3 to about 0.4%; between about 0.4 to about 0.5%; between about 0.5 to about 0.6%; between about 0.6 to about 0.7%; between about 0.7 to about 1%; between about 1 to about 3%; or between about 1.5 to about 2.5%. In some variations the liquid formulations described herein contain between about 0.1 to about 5% w/w of rapamycin.

In some variations the non-aqueous liquid component is, by way of nonlimiting example, between about 0.01 to about 99.9% of the total weight of the composition; between about 0.1 to about 99%; between about 75 to about 99.99%; between about 85 to about 99.99%; or between about 55 to about 95% w/w. In some variations the non-aqueous liquid component is between about 85 to about 99.99% w/w.

In some variations there is optionally a water component. In some variations the water component is less than about 30%, less than about 25%, less than about 20%, less than about 15%, less than about 10%, less than about 7.5%, less than about 5%, less than about 4%, less than about 3%, less than about 2%, less than about 1%, or less than about 0.5%. In some variations the water component is less than about 5% w/w.

Some variations of liquid formulations includes rapamycin between about 0.01 and about 5% by weight of the total, and a non-aqueous liquid component between about 95% and about 99.99% by weight of the total. In some variations the formulations further comprise stabilizing agents, excipients, adjuvants, or antioxidants, between about 0 and about 5% by weight of the total.

In some variations, a liquid formulation contains about 2% w/w rapamycin and about 98% w/w of a non-aqueous liquid component. In some variations, the non-aqueous liquid component comprises ethanol. In some variations, the non-aqueous liquid component comprises a liquid polyethylene glycol, including but not limited to PEG 400.

In some variations the formulation contains 2% w/w rapamycin, 4% w/w ethanol, and 94% w/w PEG 400.

In some variations, the formulation is diluted in a medium prior to administration to a subject in need thereof.

The liquid formulations may be formulated for various routes of administration, including but not limited to delivery by any route of administration described herein, including but not limited to oral administration of delivery by injection.

In Situ Gelling Formulations

In some variations, the formulations described herein are in situ gelling formulations.

An "in situ gelling formulation," as used herein, refers to a liquid formulation which forms a gel-like non-dispersed mass when the liquid formulation is placed in an aqueous medium, including but not limited to aqueous media that are water, the vitreous of an eye of a subject, and between the sclera and the conjunctiva of an eye of a subject. In some variations, an in situ gelling formulation forms a gel-like non-dispersed mass when placed in tap water.

In some variations, the in situ gelling formulation is a suspension prior to placement in an aqueous medium, and forms a gel in situ upon placement in an aqueous medium. In some variations, the in situ gelling formulation is a solution prior to placement in an aqueous medium, and forms a gel in situ upon placement in an aqueous medium. In some variations, the in situ gelling formulation is an emulsion prior to placement in an aqueous medium, and forms a gel in situ upon placement in an aqueous medium. In some variations a gel-like non-dispersed mass forms after placement of the in situ gelling formulation into an aqueous medium, including but not limited to any or all of water, an aqueous medium of a subject, the vitreous of an eye, or between the sclera and the conjunctiva of an eye. In some variations, the in situ gel is formed of a polymer matrix. In some variations a therapeutic agent is dispersed in the polymer matrix.

Described herein are in situ gelling formulations which may be used for treating, preventing, inhibiting, delaying the onset of, or causing the regression of the diseases and conditions of a subject including but not limited to a human subject. When used for treating, preventing, inhibiting, delaying the onset of, or causing the regression of the disease or condition of the subject, the in situ gelling formulation is administered to the subject.

In some variations, the in situ gelling formulation comprises one or more polymers. Described herein are various types of polymers, including polymers which are solvents, polymers which are solubilizing agents, polymers which are release modifying agents, polymers which are stabilizing agents, etc. In some variations, any combination of polymers is used wherein the polymers when combined with the therapeutic agent form any or all of a non-dispersed mass, a gel, a hydrogel, or polymeric matrix when placed in an aqueous medium, including but not limited to any or all of water, the vitreous, or between the sclera and the conjunctiva.

In some variations, the in situ gelling formulation delivers extended release of therapeutic agents to a subject when administered to the subject.

In some variations, the in situ gelling formulation comprises nanoparticles. In some variations, the nanoparticles are made by milling.

In some variations, the formulation comprises a therapeutic agent and a plurality of polymers, wherein one of the polymers is a polymethacrylate. Polymethacrylates are known by various names and are available in various preparations, including but not limited to polymeric methacrylates, methacrylic acid-ethyl acrylate copolymer (1:1), methacrylic acid-ethyl acrylate copolymer (1:1) dispersion 30 percent, methacrylic acid-methyl methacrylate copolymer (1:1), methacrylic acid-methyl methacrylate copolymer (1:2), acidum methacrylicum et ethylis acrylas polymerisatum 1:1, acidum methacrylicum et ethylis acrylas polymerisatum 1:1 dispersio 30 per centum, acidum methacrylicum et methylis methacrylas polymerisatum 1:1, acidum methacrylicum et methylis methacrylas polymerisatum 1:2, USPNF: ammonio methacrylate copolymer, methacrylic acid copolymer, methacrylic acid copolymer dispersion.

In some variations, one of the polymers is polyvinylpyrrolidone. Polyvinylpyrrolidone is known by various names and is available in various preparations, including but not limited to povidone, povidonum, kollidon; plasdone; poly [1-(2-oxo-1-pyrrolidinyl)ethylene]; polyvidone; PVP; 1-vinyl-2-pyrrolidinone polymer, and 1-Ethenyl-2-pyrrolidinone homopolymer.

One liquid formulation described herein comprises a therapeutic agent and a solvent component. The solvent component may comprise a single solvent or a combination of solvents.

In some variations, the solvent is glycerin, dimethylsulfoxide, N-methylpyrrolidone, ethanol, isopropyl alcohol, polyethylene glycol of various molecular weights, including but not limited to PEG 300 and PEG 400, or propylene glycol, or a mixture of one or more thereof.

In some variations, the solvent is polyethylene glycol. Polyethylene glycol is known by various names and is available in various preparations, including but not limited to macrogels, macrogel 400, macrogel 1500, macrogel 4000, macrogel 6000, macrogel 20000, macrogola, breox PEG; carbowax; carbowax sentry; Hodag PEG; Lipo; Lipoxol; Lutrol E; PEG; Pluriol E; polyoxyethylene glycol, and α-Hydro-ω-hydroxy-poly(oxy-1,2-ethanediyl).

Solubilization of Therapeutic Agents

One composition or liquid formulation that may be used is a composition or liquid formulation in which the therapeutic agent is dissolved in a solvent component. Generally, any solvent which has the desired effect may be used in which the therapeutic agent dissolves. In some variations the solvent is aqueous. In some variations the solvent is non-aqueous. An "aqueous solvent" is a solvent that contains at least about 50% water.

Generally, any concentration of solubilized therapeutic agent that has the desired effect can be used. The solvent component may be a single solvent or may be a mixture of solvents. The solvent component may be a single solvent or may be a mixture of solvents. Solvents and types of solutions are well known to those versed in such drug delivery technologies. See for example, Remington: The Science and Practice of Pharmacy, Twentieth Edition, Lippincott Williams and Wilkins; 20th edition (Dec. 15, 2000); Ansel's Pharmaceutical Dosage Forms and Drug Delivery Systems, Eighth Edition, Lippincott Williams and Wilkins (August 2004); Handbook Of Pharmaceutical Excipients 2003, American Pharmaceutical Association, Washington, D.C., USA and Pharmaceutical Press, London, UK; and Strickley, solubilizing Excipients in Oral and Injectable Formulations, Pharmaceutical Research, Vol. 21, No. 2, February 2004.

As noted previously, some solvents may also serve as solubilizing agents.

Solvents that may be used include but are not limited to DMSO, ethanol, methanol, isopropyl alcohol; castor oil, propylene glycol, glycerin, polysorbate 80, benzyl alcohol, dimethyl acetamide (DMA), dimethyl formamide (DMF), triacetin, diacetin, corn oil, acetyl triethyl citrate (ATC), ethyl lactate, glycerol formal, ethoxy diglycol (Transcutol, Gattefosse), tryethylene glycol dimethyl ether (Triglyme), dimethyl isosorbide (DMI), γ-butyrolactone, N-Methyl-2-pyrrolidinone (NMP), polyethylene glycol of various molecular weights, including but not limited to PEG 300 and PEG 400, and polyglycolated capryl glyceride (Labrasol, Gattefosse), combinations of any one or more of the foregoing, or analogs or derivatives of any one or more of the foregoing.

In some variations, the solvent is a polyethylene glycol. Polyethylene glycol is known by various names and is available in various preparations, including but not limited to macrogels, macrogel 400, macrogel 1500, macrogel 4000, macrogel 6000, macrogel 20000, macrogola, breox PEG; carbowax; carbowax sentry; Hodag PEG; Lipo; Lipoxol; Lutrol E; PEG; Pluriol E; polyoxyethylene glycol, and α-Hydro-ω-hydroxy-poly(oxy-1,2-ethanediyl).

In some variations the polyethylene glycol is a liquid PEG, and is one or more of PEG 300 or PEG 400.

Other solvents include an amount of a $C_6$-$C_{24}$ fatty acid sufficient to solubilize a therapeutic agent.

Phospholipid solvents may also be used, such as lecithin, phosphatidylcholine, or a mixture of various diglycerides of stearic, palmitic, and oleic acids, linked to the choline ester of phosphoric acid; hydrogenated soy phosphatidylcholine (HSPC), distearoylphosphatidylglycerol (DSPG), L-α-dimyristoylphosphatidylcholine (DMPC), L-α-dimyristoyl-phosphatidylglycerol (DMPG).

Further examples of solvents include, for example, components such as alcohols, propylene glycol, polyethylene glycol of various molecular weights, propylene glycol esters, propylene glycol esterified with fatty acids such as oleic, stearic, palmic, capric, linoleic, etc; medium chain mono-, di-, or triglycerides, long chain fatty acids, naturally occurring oils, and a mixture thereof. The oily components for the solvent system include commercially available oils as well as naturally occurring oils. The oils may further be vegetable oils or mineral oils. The oils can be characterized as non-surface active oils, which typically have no hydrophile lipophile balance value. Commercially available substances comprising medium chain triglycerides include, but are not limited to, Captex 100, Captex 300, Captex 355, Miglyol 810, Miglyol 812, Miglyol 818, Miglyol 829, and Dynacerin 660. Propylene glycol ester compositions that are commercially available encompass Captex 200 and Miglyol 840, and the like. The commercial product, Capmul MCM, comprises one of many possible medium chain mixtures comprising monoglycerides and diglycerides.

Other solvents include naturally occurring oils such as peppermint oil, and seed oils. Exemplary natural oils include oleic acid, castor oil, safflower seed oil, soybean oil, olive oil, sunflower seed oil, sesame oil, and peanut oil. Soy fatty acids may also be used. Examples of fully saturated non-aqueous solvents include, but are not limited to, esters of medium to long chain fatty acids (such as fatty acid triglycerides with a chain length of about $C_6$ to about $C_{24}$). Hydrogenated soybean oil and other vegetable oils may also be used. Mixtures of fatty acids may be split from the natural oil (for example coconut oil, palm kernel oil, babassu oil, or the like) and refined. In some embodiments, medium chain (about $C_8$ to about $C_{12}$) triglycerides, such as caprilyic/capric triglycerides derived from coconut oil or palm seed oil, may be used. Medium chain mono- and diglycerides may also be used. Other fully saturated non-aqueous solvents include, but are not limited to, saturated coconut oil (which typically includes a mixture of lauric, myristic, palmitic, capric and caproic acids), including those sold under the Miglyol™ trademark from Huls and bearing trade designations 810, 812, 829 and 840). Also noted are the NeoBee™ products sold by Drew Chemicals. Non-aqueous solvents include isopropyl myristate. Examples of synthetic oils include triglycerides and propylene glycol diesters of saturated or unsaturated fatty acids having 6 to 24 carbon atoms such as, for example hexanoic acid, octanoic (caprylic), nonanoic (pelargonic), decanoic (capric), undecanoic, lauric, tridecanoic, tetradecanoic (myristic), pentadecanoic, hexadecanoic (palmitic), heptadecanoic, octadecanoic (stearic), nonadecanoic, heptadecanoic, eicosanoic, heneicosanoic, docosanoic and lignoceric acids, and the like. Examples of unsaturated carboxylic acids include oleic, linoleic and linolenic acids, and the like. The non-aqueous solvent can comprise the mono-, di- and triglyceryl esters of fatty acids or mixed glycerides and/or propylene glycol mono- or diesters wherein at least one molecule of glycerol has been esterified with fatty acids of varying carbon atom length. A non-limiting example of a "non-oil" useful as a solvent is polyethylene glycol.

Exemplary vegetable oils include cottonseed oil, corn oil, sesame oil, soybean oil, olive oil, fractionated coconut oil, peanut oil, sunflower oil, safflower oil, almond oil, avocado oil, palm oil, palm kernel oil, babassu oil, beechnut oil, linseed oil, rape oil and the like. Mono-, di-, and triglycerides of vegetable oils, including but not limited to corn, may also be used.

Polyvinyl pyrrolidone (PVP), cross-linked or not, may also be used as a solvent. Further solvents include but are not limited to $C_6$-$C_{24}$ fatty acids, oleic acid, Imwitor 742, Capmul, F68, F68 (Lutrol), PLURONICS including but not limited to PLURONICS F108, F127, and F68, Poloxamers, Jeffamines), Tetronics, F127; cyclodextrins such as α-cyclodextrin, β-cyclodextrin, hydroxypropyl-β-cyclodextrin, sulfobutylether-β-cyclodextrin (Captisol); CMC, polysorbitan 20, Cavitron, polyethylene glycol of various molecular weights including but not limited to PEG 300 and PEG 400.

Beeswax and d-α-tocopherol (Vitamin E) may also be used as solvents.

Solvents for use in the liquid formulations can be determined by a variety of methods known in the art, including but not limited to (1) theoretically estimating their solubility parameter values and choosing the ones that match with the therapeutic agent, using standard equations in the field; and (2) experimentally determining the saturation solubility of therapeutic agent in the solvents, and choosing the ones that exhibit the desired solubility.

Solubilization of Rapamycin

Where the therapeutic agent is rapamycin, solvents that may be used for making solutions or suspensions of rapamycin include but are not limited to any solvent described herein, including but not limited to any one or more of DMSO, glycerin, ethanol, methanol, isopropyl alcohol; castor oil, propylene glycol, polyvinylpropylene, glycerin, polysorbate 80, benzyl alcohol, dimethyl acetamide (DMA), dimethyl formamide (DMF), glycerol formal, ethoxy diglycol (Transcutol, Gattefosse), tryethylene glycol dimethyl ether (Triglyme), dimethyl isosorbide (DMI), γ-butyrolactone, N-Methyl-2-pyrrolidinone (NMP), polyethylene glycol of various molecular weights, including but not limited to PEG 300 and PEG 400, and polyglycolated capryl glyceride (Labrasol, Gattefosse).

Further solvents include but are not limited to $C_6$-$C_{24}$ fatty acids, oleic acid, Imwitor 742, Capmul, F68, F68 (Lutrol), PLURONICS including but not limited to PLURONICS F108, F127, and F68, Poloxamers, Jeffamines), Tetronics, F127, beta-cyclodextrin, CMC, polysorbitan 20, Cavitron, softigen 767, captisol, and sesame oil.

Other methods that may be used to dissolve rapamycin are described in Solubilization of Rapamycin, P. Simamora et al. *Int'l J. Pharma* 213 (2001) 25-29, the contents of which is incorporated herein in its entirety.

As a nonlimiting example, rapamycin can be dissolved in 5% DMSO or methanol in a balanced salt solution. The rapamycin solution can be unsaturated, a saturated or a supersaturated solution of rapamycin. The rapamycin solution can be in contact with solid rapamycin. In one nonlimiting example, rapamycin can be dissolved in a concentration of up to about 400 mg/ml. Rapamycin can also, for example, be dissolved in propylene glycol esterified with fatty acids such as oleic, stearic, palmic, capric, linoleic, etc.

Many other solvents are possible. Those of ordinary skill in the art will find it routine to identify solvents for rapamycin given the teachings herein.

Solubilizing Agents

Generally, any solubilizing agent or combination of solubilizing agents may be used in the liquid formulations described herein.

In some variations, the solubilizing agent is a surfactant or combination of surfactants. Many surfactants are possible. Combinations of surfactants, including combinations of various types of surfactants, may also be used. For instance, surfactants which are nonionic, anionic (i.e. soaps, sulfonates), cationic (i.e. CTAB), zwitterionic, polymeric or amphoteric may be used.

Surfactants that can be used may be determined by mixing a therapeutic agent of interest with a putative solvent and a putative surfactant, and observing the characteristics of the formulation after exposure to a medium.

Examples of surfactants include but are not limited to fatty acid esters or amides or ether analogues, or hydrophilic derivatives thereof; monoesters or diesters, or hydrophilic derivatives thereof; or mixtures thereof; monoglycerides or diglycerides, or hydrophilic derivatives thereof; or mixtures thereof; mixtures having enriched mono- or/and diglycerides, or hydrophilic derivatives thereof; surfactants with a partially derivatized with a hydrophilic moiety; monoesters or diesters or multiple-esters of other alcohols, polyols, saccharides or oligosaccharides or polysaccharides, oxyalkylene oligomers or polymers or block polymers, or hydrophilic derivatives thereof, or the amide analogues thereof; fatty acid derivatives of amines, polyamines, polyimines, aminoalcohols, aminosugars, hydroxyalkylamines, hydroxypolyimines, peptides, polypeptides, or the ether analogues thereof.

Hydrophilic Lipophilic Balance ("HLB") is an expression of the relative simultaneous attraction of a surfactant for water and oil (or for the two phases of the emulsion system being considered).

Surfactants are characterized according to the balance between the hydrophilic and lipophilic portions of their molecules. The hydrophilic-lipophilic balance (HLB) number indicates the polarity of the molecule in an arbitrary range of 1-40, with the most commonly used emulsifiers having a value between 1-20. The HLB increases with increasing hydrophilicity.

Surfactants that may be used include but are not limited to those with an HLB greater than 10, 11, 12, 13 or 14. Examples of surfactants include polyoxyethylene products of hydrogenated vegetable oils, polyethoxylated castor oils or polyethoxylated hydrogenated castor oil, polyoxyethylene-sorbitan-fatty acid esters, polyoxyethylene castor oil derivatives and the like, for example, Nikkol HCO-50, Nikkol HCO-35, Nikkol HCO-40, Nikkol HCO-60 (from Nikko Chemicals Co. Ltd.); Cremophor (from BASF) such as Cremophor RH40, Cremophor RH60, Cremophor EL, TWEENs (from ICI Chemicals) e.g., TWEEN 20, TWEEN 21, TWEEN 40, TWEEN 60, TWEEN 80, TWEEN 81, Cremophor RH 410, Cremophor RH 455 and the like.

The surfactant component may be selected from compounds having at least one ether formed from at least about 1 to 100 ethylene oxide units and at least one fatty alcohol chain having from at least about 12 to 22 carbon atoms; compounds having at least one ester formed from at least about 1 to 100 ethylene oxide units and at least one fatty acid chain having from at least about 12 to 22 carbon atoms; compounds having at least one ether, ester or amide formed from at least about 1 to 100 ethylene oxide units and at least one vitamin or vitamin derivative; and combinations thereof consisting of no more than two surfactants.

Other examples of surfactants include Lumulse GRH-40, TGPS, Polysorbate-80 (TWEEN-80), Polysorbate-20 (TWEEN-20), polyoxyethylene (20) sorbitan mono-oleate), glyceryl glycol esters, polyethylene glycol esters, polyglycolyzed glycerides, and the like, or mixtures thereof; polyethylene sorbitan fatty acid esters, polyoxyethylene glycerol esters, such as Tagat TO, Tagat L, Tagat I, tagat I2 and Tagat 0 (commercially available from Goldschmidt Chemical Co., Essen, Germany); ethylene glycol esters, such as glycol stearate and distearate; propylene glycol esters, such as propylene glycol myristate; glyceryl esters of fatty acids, such as glyceryl stearates and monostearates; sorbitan esters, such as spans and TWEENs; polyglyceryl esters, such as polyglyceryl 4-oleate; fatty alcohol ethoxylates, such as Brij type emulsifiers; ethoxylated propoxylated block copolymers, such as poloxamers; polyethylene glycol esters of fatty acids, such as PEG 300 linoleic glycerides or Labrafil 2125 CS, PEG 300 oleic glycerides or Labrafil M 1944 CS, PEG 400 caprylic/capric glycerides or Labrasol, and PEG 300 caprylic/capric glycerides or Softigen 767; cremophors, such as Cremophor E, polyoxyl 35 castor oil or Cremophor EL, Cremophor EL-P, Cremophor RH 4OP, polyoxyl 40 hydrogenated castor oil, Cremophor RH40; polyoxyl 60 hydrogenated castor oil or Cremophor RH 60, glycerol monocaprylate/caprate, such as Campmul CM 10; polyoxyethylated fatty acids (PEG-stearates, PED-laurates, Brij®), polyoxylated glycerides of fatty acid, polyoxylated glycerol fatty acid esters i.e. Solutol HS-15; PEG-ethers (Mirj®), sorbitan derivatives (TWEENs), sorbitan monooleate or Span 20, aromatic compounds (Tritons®), PEG-glycerides (PECEOL™), PEG-PPG (polypropylene glycol) copolymers (PLURONICS including but not limited to PLURONICS F108, F127, and F68, Poloxamers, Jeffamines), Tetronics, Polyglycerines, PEG-tocopherols, PEG-LICOL 6-oleate; propylene glycol derivatives, sugar and polysaccharide alkyl and acyl derivatives (octylsucrose, sucrose stearate, laurolydextran etc.) and/or a mixture thereof; surfactants based on an oleate or laureate ester of a polyalcohol copolymerized with ethylene oxide; Labrasol Gelucire 44/14; polyoxytheylene stearates; saturated polyglycolyzed glycerides; or poloxamers; all of which are commercially available. Polyoxyethylene sorbitan fatty acid esters can include polysorbates, for example, polysorbate 20, polysorbate 40, polysorbate 60, and polysorbate 80. Polyoxyethylene stearates can include polyoxyl 6 stearate, polyoxyl 8 stearate, polyoxyl 12 stearate and polyoxyl 20 stearate. Saturated polyglycolyzed glycerides are, for example, GELUCIRE 44/14 or GELUCIRE™ 50/13 (Gattefosse, Westwood, N.J., U.S.A.). Poloxamers used herein include poloxamer 124 and poloxamer 188.

Surfactants include d-α-tocopheryl polyethylene glycol 1000 succinate (TPGS), polyoxyl 8 stearate (PEG 400 monostearate), polyoxyl 40 stearate (PEG 1750 monostearate) and peppermint oil.

In some variations, surfactants having an HLB lower than 10 are used. Such surfactants may optionally be used in combination with other surfactants as co-surfactants. Examples of some surfactants, mixtures, and other equivalent compositions having an HLB less than or equal to 10 are propylene glycols, glyceryl fatty acids, glyceryl fatty acid esters, polyethylene glycol esters, glyceryl glycol esters, polyglycolyzed glycerides and polyoxyethyl steryl ethers. Propylene glycol esters or partial esters form the composition of commercial products, such as Lauroglycol FCC, which contains propylene glycol laureate. The commercially available excipient Maisine 35-1 comprises long chain fatty acids, for example glyceryl linoleate. Products, such as Acconon E, which comprise polyoxyethylene stearyl ethers, may also be used. Labrafil M 1944 CS is one example of a surfactant wherein the composition contains a mixture of glyceryl glycol esters and polyethylene glycol esters.

Solubilizing Agents for Rapamycin

Many solubilizing agents may be used for rapamycin, including but not limited to those in the solubilizing agents section above.

In some variations the solubilizing agent is a surfactant. Nonlimiting examples of surfactants that may be used for rapamycin include but are not limited to surfactants with an HLB greater than 10, 11, 12, 13 or 14. One nonlimiting example is Cremophor EL. In some variations, the surfactant may be a polymeric surfactant including but not limited to PLURONICS F108, F127, and F68, and Tetronics. As noted herein, some solvents may also serve as surfactants. Those of ordinary skill in the art will find it routine to identify which solubilizing agents and surfactants may be used for rapamycin given the teachings herein.

Viscosity Modifying Agents

The liquid formulations described herein may be administered with or further comprise a viscosity modifying agent.

One exemplary viscosity modifying agent that may be used is hyaluronic acid. Hyaluronic acid is a glycosaminoglycan. It is made of a repetitive sequence of glucuronic acid and glucosamine. Hyaluronic acid is present in many tissues and organs of the body, and contributes to the viscosity and consistency of such tissues and organs. Hyaluronic acid is present in the eye, including the vitreous of the eye, and along with collagen contributes to the viscosity thereof. The liquid formulations described herein may further comprise or be administered with hyaluronic acid.

Other nonlimiting examples of viscosity modifying agents include polyalkylene oxides, glycerol, carboxymethyl cellulose, sodium alginate, chitosan, dextran, dextran sulfate and collagen. These viscosity modifying agents can be chemically modified.

Other viscosity modifying agents that may be used include but are not limited to carrageenan, cellulose gel, colloidal silicon dioxide, gelatin, propylene carbonate, carbonic acid, alginic acid, agar, carboxyvinyl polymers or carbomers and polyacrylamides, acacia, ester gum, guar gum, gum arabic, ghatti, gum karaya, tragacanth, terra, pectin, tamarind seed, larch arabinogalactan, alginates, locust bean, xanthan gum, starch, veegum, tragacanth, polyvinyl alcohol, gellan gum, hydrocolloid blends, and povidone. Other viscosity modifying agents known in the art can also be used, including but not limited to sodium carboxymethyl cellulose, algin, carageenans, galactomannans, hydropropyl methyl cellulose, hydroxypropyl cellulose, polyethylene glycol, polyvinylpyrrolidone, sodium carboxymethyl chitin, sodium carboxymethyl dextran, sodium carboxymethyl starch, xanthan gum, and zein.

Other Components of Formulations

The formulations described herein may further comprise various other components such as stabilizers, for example. Stabilizers that may be used in the formulations described herein include but are not limited to agents that will (1) improve the compatibility of excipients with the encapsulating materials such as gelatin, (2) improve the stability (e.g. prevent crystal growth of a therapeutic agent such as rapamycin) of a therapeutic agent such as rapamycin and/or rapamycin derivatives, and/or (3) improve formulation stability. Note that there is overlap between components that are stabilizers and those that are solvents, solubilizing agents or surfactants, and the same component can carry out more than one role.

Stabilizers may be selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers, and combinations thereof. Amide analogues of the above stabilizers can also be used. The chosen stabilizer may change the hydrophobicity of the formulation (e.g. oleic acid, waxes), or improve the mixing of various components in the formulation (e.g. ethanol), control the moisture level in the formula (e.g. PVP), control the mobility of the phase (substances with melting points higher than room temperature such as long chain fatty acids, alcohols, esters, ethers, amides etc. or mixtures thereof; waxes), and/or improve the compatibility of the formula with encapsulating materials (e.g. oleic acid or wax). Some of these stabilizers may be used as solvents/co-solvents (e.g. ethanol). Stabilizers may be present in sufficient amount to inhibit the therapeutic agent's (such as rapamycin's) crystallization.

Examples of stabilizers include, but are not limited to, saturated, monoenoic, polyenoic, branched, ring-containing, acetylenic, dicarboxylic and functional-group-containing fatty acids such as oleic acid, caprylic acid, capric acid, caproic acid, lauric acid, myristic acid, palmitic acid, stearic acid, behenic acid, linoleic acid, linolenic acid, eicosapentaenoic acid (EPA), DHA; fatty alcohols such as stearyl alcohol, cetyl alcohol, ceteryl alcohol; other alcohols such as ethanol, isopropyl alcohol, butanol; long chain fatty acid esters, ethers or amides such as glyceryl stearate, cetyl stearate, oleyl ethers, stearyl ethers, cetyl ethers, oleyl amides, stearyl amides; hydrophilic derivatives of fatty acids such as polyglyceryl fatty acids, polyethylene glycol fatty acid esters; polyvinylpyrrolidones, polyvinylalcohols (PVAs), waxes, docosahexaenoic acid and de-hydroabietic acid etc.

The formulations described may further contain a gelling agent that alters the texture of the final formulation through formation of a gel.

The therapeutic agents for use as described herein, such as rapamycin, may be subjected to conventional pharmaceutical operations, such as sterilization and compositions containing the therapeutic agent may also contain conventional adjuvants, such as preservatives, stabilizers, wetting agents, emulsifiers, buffers etc. The therapeutic agents may also be formulated with pharmaceutically acceptable excipients for clinical use to produce a pharmaceutical composition. Formulations may be presented as a solution, suspension, particles of solid material, a discrete mass of solid material, nanoparticles, incorporated within a polymer matrix, liquid formulations or in any other form appropriate for the selected route of administration. The therapeutic agents may be used to prepare a medicament to treat, prevent, inhibit, delay onset, or cause regression of any of the conditions described herein. In some variations, the therapeutic agents may be used to prepare a medicament to treat any of the conditions described herein.

A composition containing a therapeutic agent such as rapamycin may contain one or more adjuvants appropriate for the indicated route of administration. Adjuvants with which the therapeutic agent may be admixed with include but are not limited to lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. When a solubilized formulation is required the therapeutic agent may be in a solvent including but not limited to polyethylene glycol of various molecular weights, propylene glycol, carboxymethyl cellulose colloidal solutions, methanol, ethanol, DMSO, corn oil, peanut oil, cottonseed oil, sesame oil, tragacanth gum, and/or various buffers. Other adjuvants and modes of administration are well known in the pharmaceutical art and may be used in the practice of the methods, compositions and liquid formulations described herein. The carrier or diluent may include time delay material, such as glyceryl monostearate or glyceryl distearate alone or with a wax, or other materials well known in the art. The formulations for use as described herein may also include gel formulations, erodible and non-erodible polymers, microspheres, and liposomes.

Other adjuvants and excipients that may be used include but are not limited to $C_8$-$C_{10}$ fatty acid esters such as softigen 767, polysorbate 80, PLURONICS, Tetronics, Miglyol, and Transcutol.

Additives and diluents normally utilized in the pharmaceutical arts can optionally be added to the pharmaceutical composition and the liquid formulation. These include thickening, granulating, dispersing, flavoring, sweetening, coloring, and stabilizing agents, including pH stabilizers, other excipients, anti-oxidants (e.g., tocopherol, BHA, BHT, TBHQ, tocopherol acetate, ascorbyl palmitate, ascorbic acid propyl gallate, and the like), preservatives (e.g., parabens), and the like. Exemplary preservatives include, but are not limited to, benzylalcohol, ethylalcohol, benzalkonium chloride, phenol, chlorobutanol, and the like. Some useful anti-oxidants provide oxygen or peroxide inhibiting agents for the formulation and include, but are not limited to, butylated hydroxytoluene, butylhydroxyanisole, propyl gallate, ascorbic acid palmitate, α-tocopherol, and the like. Thickening agents, such as lecithin, hydroxypropylcellulose, aluminum stearate, and the like, may improve the texture of the formulation.

In some variations, the therapeutic agent is rapamycin, and the rapamycin is formulated as RAPAMUNE in solid or liquid form. In some variations, the RAPAMUNE is formulated as an oral dosage.

In addition, a viscous polymer may be added to the suspension, assisting the localization and ease of placement and handling. In some uses of the liquid formulation, a pocket in the sclera may be surgically formed to receive an injection of the liquid formulations. The hydrogel structure of the sclera can act as a rate-controlling membrane. Particles of therapeutic agent substance for forming a suspension can be produced by known methods including but not limited to via ball milling, for example by using ceramic beads. For example, a Cole Parmer ball mill such as Labmill 8000 may be used with 0.8 mm YTZ ceramic beads available from Tosoh or Norstone Inc.

The formulations may conveniently be presented in unit dosage form and may be prepared by conventional pharmaceutical techniques. Such techniques include the step of bringing into association the therapeutic agent and the pharmaceutical carrier(s) or excipient(s). The formulations may be prepared by uniformly and intimately bringing into associate the active ingredient with liquid carriers or finely divided solid carriers or both, and then, if necessary, shaping the product.

In some variations, the formulations described herein are provided in one or more unit dose forms, wherein the unit dose form contains an amount of a liquid formulation described herein that is effective to treat or prevent the disease or condition for which it is being administered. In some variations, the formulations described herein are provided in one or more unit dose forms, wherein the unit dose form contains an amount of a liquid rapamycin formulation described herein that is effective to treat or prevent the disease or condition for which it is being administered.

In some embodiments, the unit dose form is prepared in the concentration at which it will be administered. In some variations, the unit dose form is diluted prior to administration to a subject. In some variations, a liquid formulation described herein is diluted in an aqueous medium prior to administration to a subject. In some variations the aqueous medium is an isotonic medium. In some variations, a liquid formulation described herein is diluted in an non-aqueous medium prior to administration to a subject.

In a further aspect, provided herein are kits comprising one or more unit dose forms as described herein. In some embodiments, the kit comprises one or more of packaging and instructions for use to treat one or more diseases or conditions. In some embodiments, the kit comprises a diluent which is not in physical contact with the formulation or pharmaceutical formulation. In some embodiments, the kit comprises any of one or more unit dose forms described herein in one or more sealed vessels. In some embodiments, the kit comprises any of one or more sterile unit dose forms.

In some variations, the unit dose form is in a container, including but not limited to a sterile sealed container. In some variations the container is a vial, ampule, or low volume applicator, including but not limited to a syringe. In some variations, a low-volume applicator is pre-filled with rapamycin for treatment of an ophthalmic disease or condition, including but not limited to a limus compound for treatment of age-related macular degeneration. Described herein is a pre-filled low-volume applicator pre-filled with a formulation comprising a therapeutic agent, including but not limited to rapamycin. In some variations a low-volume applicator is pre-filled with a solution comprising a therapeutic agent, including but not limited to rapamycin and a polyethylene glycol, and optionally further comprises one or more additional components including but not limited to ethanol. In some variations a pre-filled low-volume applicator is pre-filled with a solution comprising about 2% rapamycin, about 94% PEG-400, about 4% ethanol.

Described herein are kits comprising one or more containers. In some variations a kit comprises one or more low-volume applicators is pre-filled with a formulation described herein comprising a therapeutic agent, including but not limited to formulations comprising rapamycin, formulations comprising rapamycin and a polyethylene glycol, and optionally further comprises one or more additional components including but not limited to ethanol, and formulations in liquid form comprising about 2% rapamycin, about 94% PEG-400, about 4% ethanol. In some variations the kit comprises one or more containers, including but not limited to pre-filled low-volume applicators, with instructions for its use. In a further variation a kit comprises one or more low-volume applicators pre-filled with rapamycin, with instructions for its use in treating a disease or condition described herein. In some variations, the containers described herein are in a secondary packaging.

Methods of Treatment

Unless the context clearly indicates otherwise, any of the therapeutic agents described herein may be used in a method described herein for treating, preventing, inhibiting, delaying on set of, or causing the regression of any of the diseases and conditions described herein.

In some variations any one or more of the formulations described herein are used to deliver one or more therapeutic agents described herein via a method described herein. Generally, the therapeutic agent may be formulated in any formulation capable of delivery of a therapeutically effective amount of the therapeutic agent to a subject or to the subject for the required treatment period. In some variations the required treatment period is met by a single administration of a sustained release formulation that is predicted to deliver an effective amount of the therapeutic agent for the predicted duration period of the disease or condition. In some variations the required treatment period is met by a schedule of multiple administrations.

In some variations the required treatment period is met by multiple administrations of a formulation, including but not limited to a sustained release formulation.

As used herein, to "inhibit" a disease or condition by administration of a therapeutic agent means that the progress of at least one detectable physical characteristic or symptom of the disease or condition is slowed or stopped following administration of the therapeutic agent as compared to the progress of the disease or condition without administration of the therapeutic agent.

As used herein, to "prevent" a disease or condition by administration of a therapeutic agent means that the detectable physical characteristics or symptom of the disease or condition do not develop following administration of the therapeutic agent.

As used herein, to "delay onset of" a disease or condition by administration of a therapeutic agent means that at least one detectable physical characteristic or symptom of the disease or condition develops later in time following administration of the therapeutic agent as compared to the progress of the disease or condition without administration of the therapeutic agent.

As used herein, to "treat" a disease or condition by administration of a therapeutic agent means that the progress of at least one detectable physical characteristic or symptom of the disease or condition is slowed, stopped, or reversed following administration of the therapeutic agent as compared to the progress of the disease or condition without administration of the therapeutic agent.

As used herein, to "cause regression of" a disease or condition by administration of a therapeutic agent means that the progress of at least one detectable physical characteristic or symptom of the disease or condition is reversed to some extent following administration of the therapeutic agent.

A subject, including but not limited to a human subject, having a predisposition for or in need of prevention may be identified by the skilled practitioner by established methods and criteria in the field given the teachings herein. The skilled practitioner may also readily diagnose individuals as in need of inhibition or treatment based upon established criteria in the field for identifying angiogenesis and/or neovascularization given the teachings herein.

As used herein, a "subject" is generally any animal that may benefit from administration of the formulations described herein. In some variations the therapeutic agents are administered to a mammalian subject. In some variations the formulations are administered to a human subject. In some variations the formulations are administered to a veterinary animal subject. In some variations the formulations are administered to a model experimental animal subject. In some variations the formulations are administered to a veterinary animal that is a pet. In some variations the formulations are administered to a veterinary animal that is of agronomic relevance.

An "effective amount," which is also referred to herein as a "therapeutically effective amount," of a therapeutic agent for administration as described herein is that amount of the therapeutic agent that provides the therapeutic effect sought when administered to the subject, including but not limited to a human subject. The achieving of different therapeutic effects may require different effective amounts of therapeutic agent. For example, the therapeutically effective amount of a therapeutic agent used for preventing a disease or condition may be different from the therapeutically effective amount used for treating, inhibiting, delaying the onset of, or causing the regression of the disease or condition. In addition, the therapeutically effective amount may depend on the age, weight, and other health conditions of the subject as is well know to those versed in the disease or condition being addressed. Thus, the therapeutically effective amount may not be the same in every subject to which the therapeutic agent is administered.

An effective amount of a therapeutic agent for treating, preventing, inhibiting, delaying the onset of, or causing the regression of a specific disease or condition is also referred to herein as the amount of therapeutic agent effective to treat, prevent, inhibit, delay the onset of, or cause the regression of the disease or condition.

Those of skill in the art will know how to determine the appropriate level of a therapeutic agent described herein to treat a disease or condition described herein, based on the teachings provided in this specification and in the drawings. As one example, to determine whether a level of a therapeutic agent is a "therapeutically effective amount" to treat, prevent, inhibit, delay on set of, or cause the regression of the diseases and conditions described in the Diseases and Conditions section, a formulation may be administered in in vitro or in animal models for the diseases or conditions of interest, and the effects may be observed. A nonlimiting example of scientific references related to tissue accumulation and pharmokinetics of rapamycin is Napoli and Taylor, *From Beach to Bedside: History of the Development of Sirolimus*, 23:559-586 (2001). In addition, dose ranging human clinical trials may be conducted to determine the therapeutically effective amount of a therapeutic agent.

An "effective anti-permeability amount," which is also referred to herein as a "therapeutically effective anti-permeability amount," of a therapeutic agent as described herein is that amount of the therapeutic agent that provides an anti-permeability effect when administered to a subject, including but not limited to a human subject. The achieving of anti-permeability effects may require different effective amounts of therapeutic agent depending on the disease being treated, prevented, inhibited, onset delayed, or regression caused. The achieving of anti-permeability effects may require different effective amounts of therapeutic agent depending on the tissue being treated. In addition, the effective anti-permeability amount may depend on the age, weight, and other health conditions of the subject as is well know to those versed in the disease or condition being addressed. Thus, the effective anti-permeability amount may not be the same in every subject to which the therapeutic agent is administered. Those of skill in the art are versed in determining the effective amount for a given subject given these parameters and the teachings herein.

Doses and Tissue Levels

Unless the context clearly indicates otherwise, any of the formulations described herein may be used to administer the doses or deliver the tissue levels of any of the therapeutic agents described herein to a subject in need thereof. Unless the context clearly indicates otherwise, the subject may be a veterinary, a mammalian, or a human subject. In some variations, the subject is a human subject.

In some variations, an amount or concentration of a therapeutic agent is administered that is equivalent to an amount or concentration of rapamycin. Those of skill in the art, based on the teachings herein can determine what amount or concentration of a given therapeutic agent is equivalent to an amount or concentration of rapamycin by, for example, administering the therapeutic agent at various amounts or concentrations to a disease model system, such as an in vivo or in vivo model system, and comparing the results in the model system relative to the results of various amounts or concentrations of rapamycin. Those of skill in the art, based on the teachings herein can also determine what amount or concentration of a given therapeutic agent is equivalent to an amount or concentration of rapamycin by reviewing the scientific literature for experiments performed comparing rapamycin to other therapeutic agents. It is understood that even the same therapeutic agent may have a different equivalent level of rapamycin when, for example, a different disease or disorder is being evaluated, or a different type of formulation is used. Nonlimiting examples of scientific references with comparative studies of rapamycin and other therapeutic agents on ocular disease are Ohia et al., *Effects of steroids and immunosuppressive drugs on endotoxin-uveitis in rabbits*, J. Ocul. Pharmacol. 8(4):295-307 (1992); Kulkarni, *Steroidal and nonsteroidal drugs in endotoxin-induced uveitis*, J. Ocul. Pharmacol. 10(1):329-34 (1994); Hafizi et al., *Differential effects of rapamycin, cyclosporine A, and FK506 on human coronary artery smooth muscle cell proliferation and signaling*, Vascul Pharmacol. 41(4-5):167-76 (2004); and US 2005/0187241.

As one nonlimiting example, in a model for retinal edema, if a therapeutic agent is found to be approximately 10-fold less potent or efficacious than rapamycin in the treatment of retinal edema, a dose of 10× of the therapeutic agent would be equivalent to a 1× dose of rapamycin. Or if a therapeutic agent is found to be approximately 10-fold more potent or efficacious than rapamycin in the treatment of retinal edema, a 0.1× dose of the therapeutic agent would be administered relative to a 1× dose of rapamycin. Other models for the diseases or conditions described herein may be used to determine the appropriate amount of a therapeutic agent that is equivalent to a given amount of rapamycin for the therapeutic effect sought, such as treating or preventing the disease or disorder.

Unless the context clearly indicates otherwise, any of the therapeutic agents described herein may be delivered in an amount equivalent to an amount of rapamycin. Unless the context clearly indicates otherwise, any analogs, derivatives, prodrugs, salts or esters of the therapeutic agents described herein may be delivered in an amount equivalent to an amount of rapamycin. Unless the context clearly indicates otherwise, any analogs, derivatives, prodrugs, salts or esters of rapamycin described herein may be delivered in an amount equivalent to an amount of rapamycin.

In some variations, the therapeutic agent is an immunophilin binding compound or an analog, derivative, prodrug, salt or ester thereof. In some variations, the therapeutic agent is a limus compound or an analog, derivative, prodrug, salt or ester thereof. In some variations, the therapeutic agent is rapamycin or an analog, derivative, prodrug, salt or ester thereof. In some variations, the therapeutic agent is SDZ-RAD, tacrolimus, everolimus, pimecrolimus, CCI-779, AP23841, ABT-578, TAFA-93, RAD-001, temsirolimus, AP23573, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, monoester derivatives of rapamycin, diester derivatives of rapamycin, 27-oximes of rapamycin; 42-oxo analogs of rapamycin; bicyclic rapamycins; rapamycin dimers; silyl ethers of rapamycin; rapamycin arylsulfonates, rapamycin sulfamates, monoesters at positions 31 and 42, diesters at positions 31 and 42, 30-demethoxy rapamycin, and pharmaceutically acceptable salts and esters thereof. In some variations, the therapeutic agent is rapamycin, SDZ-RAD, tacrolimus, everolimus, pimecrolimus, CCI-779, AP23841, ABT-578, and pharmaceutically acceptable salts and esters thereof. In some variations the therapeutic agent is rapamycin.

In some nonlimiting variations, the diseases or conditions described herein are treated, prevented, inhibited, regression caused, or onset delayed by administering an amount of therapeutic agent giving a tissue level concentration in the tissue associated with the disease or condition which is equivalent to a rapamycin concentration of between about 0.001 pg/mg and about 20 µg/mg. In some nonlimiting variations, the diseases or conditions described herein are treated, prevented, inhibited, regression caused, or onset delayed by providing an amount of therapeutic agent giving a tissue level concentration in the tissue associated with the disease or condition which is equivalent to a rapamycin concentration of between 0.001 ng/ml and 10 mg/ml.

In some nonlimiting variations, the diseases or conditions described herein are treated, prevented, inhibited, regression caused, or onset delayed by providing an amount of therapeutic agent giving a tissue level concentration in the tissue associated with the disease or condition which is equivalent to a rapamycin concentration of between 0.001 pg/mg and 20 µg/mg, between 0.001 pg/mg and 1 ng/mg, between 0.001 pg/mg and 10 ng/mg, between 0.01 pg/mg and 100 ng/mg, between 0.01 pg/mg and 10 ng/mg, between 0.1 pg/mg and 100 ng/mg, between 1 ng/mg and 1 µg/mg, between 1 ng/mg and 500 ng/mg, between 10 n/mg and 400 µg/mg, between between 1 ng/mg and 300 ng/mg, between 200 ng/mg and 700 ng/mg, between 500 ng/mg and 1 µg/mg, between 800 ng/mg and 1.2 µg/mg, or between 1 µg/mg and 5 µg/mg. In some variations, the therapeutic agent is rapamycin.

In some nonlimiting variations, the diseases or conditions described herein are treated, prevented, inhibited, regression caused, or onset delayed by providing an amount of therapeutic agent giving a tissue level concentration in the tissue associated with the disease or condition which is equivalent to a rapamycin concentration of between about 0.001 ng/ml and about 10 mg/ml, between 0.01 ng/ml and 1 µg/ml, between 1 ng/ml and 1 µg/ml, between 0.01 ng/ml and 100 µg/ml, between 0.01 ng/ml and 10 ng/ml, between 0.1 ng/ml and 100 µg/ml, between 100 ng/ml and 1 µg/ml, between 1 µg/ml and 500 µg/ml, between 10 mg/ml and 400 mg/ml, between between 1 µg/ml and 300 µg/ml, between 200 ng/mg and 700 µg/ml, between 500 ng/mg and 5 mg/ml, between 500 µg/ml and 1 mg/ml, or between 1 mg/ml and 5 mg/ml. In some variations, the therapeutic agent is rapamycin.

Those of skill in the art will perceive that the dose and the route of administration depend upon the disease or disorder being treated, prevented, inhibited, regression caused, or onset delayed.

In some variations, an effective amount of rapamycin is delivered to a subject. In some variations, an effective antipermeability amount of rapamycin is delivered to a subject. In some variations, an amount of rapamycin is administered in a formulation which results in a concentration of between 0.001 pg/mg and 20 µg/mg of rapamycin in a tissue associated with the disease or disorder being treated, prevented, inhibited, regression caused, or onset delayed. In some variations, an amount of rapamycin is administered in a formulation which results in a concentration of between 0.001 ng/ml and about 10 mg/ml in a tissue associated with the disease or disorder being treated, prevented, inhibited, regression caused, or onset delayed.

Those of skill in the art, based on the teachings herein and by reviewing scientific literature can determine the human equivalent dosage of a given therapeutic agent based on the amount or concentration of rapamycin given to an animal (i.e., a hamster). One such method of calculating human equivalent doses is provided in the FDA Guidance for Industry and Reviewers, Estimating the Safe Start Dose of Clinical Trial for Therapeutics in Adult Healthy Volunteers, available at http://www.fda.gov/cber/gdlns/dose.htm. For example, to convert hamster doses in mg/kg to human equivalent doses in mg/kg, the hamster dosage in mg/kg may be divided by 7.4 to equal a human equivalent dosage in mg/kg. Those of skill in the art, in view of the teachings described herein and their knowledge about the relative dosings of certains animal subjects and, for example, human subjects, will be able to determine the appropriate amount of the therapeutic agent.

In some nonlimiting variations, the diseases or conditions described herein are treated, prevented, inhibited, regression caused, or onset delayed by administering a dose of a therapeutic agent to a subject which is equivalent to a dose of rapamycin of no greater than about 2 mg/kg, or no greater than about 0.5 mg/kg, or no greater than about 0.1 mg/kg. In some variations, the diseases or conditions described herein are treated, prevented, inhibited, regression caused, or onset delayed by administering a dose of a therapeutic agent to a subject which is equivalent to a dose of rapamycin of any of about between 0.1 mg/kg to 0.5 mg/kg or between 0.1 mg/kg to 2.0 mg/kg. In some variations, the diseases or conditions described herein are treated, prevented, inhibited, regression caused, or onset delayed by administering a dose of a therapeutic agent to a subject which is equivalent to a dose of rapamycin of any of about 0.1 mg/kg, 0.5 mg/kg, or 2.0 mg/kg.

In some nonlimiting variations, the diseases or conditions described herein are treated, prevented, inhibited, regression caused, or onset delayed by administering a dose of a therapeutic agent to a subject which is equivalent to a dose of rapamycin of no greater than about 0.27 mg/kg, or no greater than about 0.067 mg/kg, or no greater than about 0.0135 mg/kg. In some variations, the diseases or conditions described herein are treated, prevented, inhibited, regression caused, or onset delayed by administering a dose of a therapeutic agent to a subject which is equivalent to a dose of rapamycin of either of between 0.0135 mg/kg to 0.067 mg/kg or between 0.0135 mg/kg to 0.27 mg/kg. In some variations, the diseases or conditions described herein are treated, prevented, inhibited, regression caused, or onset delayed by administering a dose of a therapeutic agent to a subject which is equivalent to a dose of rapamycin of any of about 0.0135 mg/kg, 0.067 mg/kg, or 0.27 mg/kg.

In some nonlimiting variations, the diseases or conditions described herein are treated, prevented, inhibited, regression caused, or onset delayed by administering to a subject in need thereof an effective amount or effective antipermeability amount of a formulation that when injected intraperitoneally into a hamster delivers an amount of the therapeutic agent sufficient to achieve an average concentration of therapeutic agent in cheek tissue of the hamster equivalent to a rapamycin concentration of any of no greater than about 7 ng/g, no greater than about 11 ng/g, or no greater than about 40 ng/g. In some variations, the diseases or conditions described herein are treated, prevented, inhibited, regression caused, or onset delayed by administering to a subject in need thereof an effective amount or effective antipermeability amount of a formulation that when injected intraperitoneally into a hamster delivers an amount of the therapeutic agent sufficient to achieve an average concentration of therapeutic agent in cheek tissue of the hamster equivalent to a rapamycin concentration of any of about between 7 ng/g to 11 ng/g or between 11 ng/g to 40 ng/g. In some variations, the diseases or conditions described herein are treated, prevented, inhibited, regression caused, or onset delayed by administering to a subject in need thereof an effective amount or effective antipermeability amount of a formulation that when injected intraperitoneally into a hamster delivers an amount of the therapeutic agent sufficient to achieve an average concentration of therapeutic agent in cheek tissue of the hamster equivalent to a rapamycin concentration of any of about 7 ng/g, 11 ng/g, or 40 ng/g. In some variations, the diseases or conditions described herein are treated, prevented, inhibited, regression caused, or onset delayed by administering to a subject in need thereof an effective amount or effective antipermeability amount of a formulation that when injected intraperitoneally into a hamster delivers an amount of the therapeutic agent sufficient to achieve an average concentration of therapeutic agent in cheek tissue of the hamster equivalent to a rapamycin of any of between 0.01 pg/g and 7 ng/g, between 0.1 pg/g and 7 ng/g, between 0.1 pg/g and 1 ng/g, between 0.01 ng/g and 1 ng/g, between 0.1 pg/g and 5 ng/g, between 5 ng/g and 15 ng/g, between 1 ng/g and 11 ng/g, between 1 ng/g and 20 ng/g, between 10 ng/g and 40 ng/g, between 20 ng/g and 45 ng/g.

In some variations, the diseases or conditions described herein are treated, prevented, inhibited, regression caused, or onset delayed by administering to a subject in need thereof an effective amount or effective antipermeability amount of a formulation that delivers an amount of a therapeutic agent sufficient to achieve a concentration equivalent to an amount of rapamycin in a tissue associated with the disease or condition of any of between 0.01 pg/g and 7 ng/g, between 0.1 pg/g and 7 ng/g, between 0.1 pg/g and 1 ng/g, between 0.01 ng/g and 1 ng/g, between 0.1 pg/g and 5 ng/g, between 5 ng/g and 15 ng/g, between 1 ng/g and 11 ng/g, between 1 ng/g and 20 ng/g, between 10 ng/g and 40 ng/g, between 20 ng/g and 45 ng/g.

In some variations, the diseases or conditions described herein are treated, prevented, inhibited, regression caused, or onset delayed by administering to a subject in need thereof an effective amount or effective antipermeability amount of a formulation that delivers an amount of a therapeutic agent sufficient to achieve a concentration equivalent to an amount of rapamycin in a tissue associated with the disease or condition of any of no greater than about 7 ng/g, no greater than about 11 ng/g, or no greater than about 40 ng/g. In some variations, the diseases or conditions described herein are treated, prevented, inhibited, regression caused, or onset delayed by administering to a subject in need thereof an effective amount or effective antipermeability amount of a formulation that delivers an amount of a therapeutic agent sufficient to achieve a concentration equivalent to an amount of rapamycin in a tissue associated with the disease or condition of any of about between 7 ng/g to 11 ng/g or between 11 ng/g to 40 ng/g. In some variations, the diseases or conditions described herein are treated, prevented, inhibited, regression caused, or onset delayed by administering to a subject in need thereof an effective amount or effective antipermeability amount of a formulation that delivers an amount of a therapeutic agent sufficient to achieve a concentration equivalent to an amount of rapamycin in a tissue associated with the disease or condition of any of about 7 ng/g, 11.01 ng/g, or 40 ng/g.

In some variations, the diseases or conditions described herein are treated, prevented, inhibited, regression caused, or onset delayed by administering to a subject in need thereof an effective amount or effective antipermeability amount of a formulation that delivers an amount of rapamycin sufficient to achieve a concentration of rapamycin in a tissue associated with the disease or condition of any of between 0.01 pg/g and 7 ng/g, between 0.1 pg/g and 7 ng/g, between 0.1 pg/g and 1 ng/g, between 0.01 ng/g and 1 ng/g, between 0.1 pg/g and 5 ng/g, between 5 ng/g and 15 ng/g, between 1 ng/g and 11 ng/g, between 1 ng/g and 20 ng/g, between 10 ng/g and 40 ng/g, between 20 ng/g and 45 ng/g.

In some variations, the diseases or conditions described herein are treated, prevented, inhibited, regression caused, or onset delayed by administering to a subject in need thereof an effective amount or effective antipermeability amount of a formulation that delivers an amount of rapamycin sufficient to achieve a concentration of rapamycin in a tissue associated with the disease or condition of any of no greater than about 7 ng/g, no greater than about 11 ng/g, or no greater than about 40 ng/g. In some variations, the diseases or conditions described herein are treated, prevented, inhibited, regression caused, or onset delayed by administering to a subject in need thereof an effective amount or effective antipermeability amount of a formulation that delivers an amount of rapamycin sufficient to achieve a concentration of rapamycin in a tissue associated with the disease or condition of any of about between 7 ng/g to 11 ng/g or between 11 ng/g to 40 ng/g. In some variations, the diseases or conditions described herein are treated, prevented, inhibited, regression caused, or onset delayed by administering to a subject in need thereof an effective amount or effective antipermeability amount of a formulation that delivers an amount of rapamycin sufficient to achieve a concentration of rapamycin in a tissue associated with the disease or condition of any of about 7 ng/g, 11 ng/g, or 40 ng/g.

Routes of Administration

The methods and formulations described herein deliver one or more therapeutic agents to a subject, including but not limited to a human subject.

In some variations, the methods and formulations described herein deliver one or more therapeutic agents to an aqueous medium of a human subject.

In some variations, the methods and formulations described herein deliver one or more therapeutic agents to an aqueous medium in or proximal to an area where a disease or condition is to be treated, prevented, inhibited, onset delayed, or regression caused. In some variations, the methods and formulations described herein systemically deliver one or more therapeutic agents to human subject to treat, prevent, inhibit, delay onset, or cause regression of a disease or conditions described herein.

In some variations, the methods and formulations described herein deliver one or more therapeutic agents to an eye of a subject, including the macula and the retina choroid tissues, in an amount and for a duration effective to treat, prevent, inhibit, delay the onset of, or cause the regression of the diseases and conditions described in the Diseases and Conditions section.

"Retina choroid" and "retina choroid tissues," as used herein, are synonymous and refer to the combined retina and choroid tissues of the eye.

"Subconjunctival" placement or injection, as used herein, refers to placement or injection between the sclera and conjunctiva. Subconjunctival is sometimes referred to herein as "sub-conj" administration.

Routes of administration that may be used in the methods described herein to administer a formulation include but are not limited to placement of the formulation, for example by injection, into a subject, including but not limited to an aqueous medium in the subject. In some variations a formulation is administered systemically, including but not limited to the following delivery routes: rectally, vaginally, by infusion, intramuscularly, intraperitoneally, intraarterially, intrathecally, intrabronchially, intracisternally, cutaneously, subcutaneously, intradermally, transdermally, intravenously, intracervically, intraabdominally, intracranially, intraocularly, periocularly, intrapulmonarily, intrathoracically, intratracheally, nasally, buccally, sublingually, orally, parenterally, topically, by implantation, as part of an embolization procedure, transcutaneously, directly into a nerve, directly into the optic nerve, direct injection into the optic nerve head, transretinally, transsclerally into an area of effusion or exudation, or inhaled after nebulisation or aerosolization.

In some variations formulations comprising therapeutic agent are administered directly to the eye using one or more of a variety of procedures, including but not limited to procedures in which (1) the therapeutic agent is administered by injection using a syringe and hypodermic needle, (2) a specially designed device is used to inject the therapeutic agent, (3) prior to injection of the therapeutic agent, a pocket is surgically formed within the sclera to serve as a receptacle for the therapeutic agent or therapeutic agent composition. For example, in one administration procedure a surgeon forms a pocket within the sclera of the eye followed by injection of a solution or formulation comprising the therapeutic agent into the pocket.

Other administration procedures include, but are not limited to procedures in which (1) a formulation of the therapeutic agent is injected through a specially designed curved cannula to place the therapeutic agent directly against a portion of the eye, (2) a compressed form of the therapeutic agent is placed directly against a portion of the eye, (3) the therapeutic agent is inserted into the sclera by a specially designed injector or inserter, (4) the formulation comprising the therapeutic agent is incorporated within a polymer, (5) a surgeon makes a small conjunctival incision through which to pass a suture and any therapeutic agent delivery structure so as to secure the structure adjacent to the sclera, (6) a needle is used for injection directly into the vitreous of an eye, or into any other site described.

In some variations, rapamycin is incorporated into or coats a suture.

The formulations described herein may be used directly, for example, by injection, as an elixir, for topical administration including but not limited to via eye drops, or in hard or soft gelatin or starch capsules. The capsules may be banded to prevent leakage.

When the route of administration is oral, non-limiting examples of the formulation include solid, liquid, controlled-release, coated-bead, diffusion-based, reservoir-containing, tablets, chewable tablets, rapidly disintegrating, buccal, effervescent, and polymer-based formulations.

In some variations the route of administration is by infusion. In some variations, non-limiting examples of methods that may be used to deliver the formulations described herein include infusion devices, IV administration sets, IV pumps and/or controllers, IV catheters, premixed IV solutions, hypodermic products, prefilled syringes, hypodermic syringes, hypodermic needles, gene/protein targeting or delivery systems, hemodialysis, peritoneal dialysis, and enteral feeding products.

In some variations the route of administration is by inhalation. In some variations, non-limiting examples of methods that may be used to deliver the formulations described herein include metered dose inhalers, dry powder inhalers, nasal spray dispensers, ventilators, and nebulizers.

In some variations the route of administration is by a transdermal or implantable systems. Non-limiting examples of methods that may be used to deliver the formulations described herein include transdermal drug delivery systems, implantable drug delivery systems, pulse generators, drug inserts, drug-containing devices, drug-coated devices, drug-eluting devices, and drug-eluting stents.

One method that may be used to deliver the formulations described herein is delivery by injection into a subject, including but not limited to a human subject.

In some variation the formulations described herein are placed proximate to the eye of a subject, including but not limited to intraocular and periocular placement or injection. Nonlimiting examples of positions that are in or proximate to an eye of a subject include intracameral, anterior chamber, periocular, subconjunctival, subtenon, retrobulbar, peribulbar and posterior juxtascleral delivery. A "periocular" route of administration means placement near or around the eye. For a description of exemplary periocular routes for retinal drug delivery, see *Periocular routes for retinal drug delivery*, Raghava et al. (2004), Expert Opin. Drug Deliv. 1(1): 99-114, which is incorporated herein by reference in its entirety.

In some variations the formulations described herein are administered intraocularly. Intraocular administration includes placement or injection within the eye, including in the vitreous.

Ocular sites to which the formulations may be administered include but are not limited to the vitreous, aqueous humor, sclera, conjunctiva, between the sclera and conjunctiva, the retina choroid tissues, macula, or other area in or proximate to the eye of a subject. Methods that may be used for placement of the formulations include but are not limited to injection.

Method of Preparing Formulations

One nonlimiting method that may be used for preparing the formulations described herein, including but not limited to liquid formulations comprising rapamycin, is by mixing a solvent and a therapeutic agent together at room temperature or at slightly elevated temperature until a solution or suspension is obtained, with optional use of a sonicator, and then cooling the formulation. Other components including but not limited to those described above may then be mixed with the formulation. Other preparation methods that may be used are described herein including in the examples, and those of skill in the art will be able to select other preparation methods based on the teachings herein and by consulting relevant references such as Remington: The Science and Practice of Pharmacy, Twentieth Edition, Lippincott Williams and Wilkins; 20th edition (Dec. 15, 2000).

In some variations, the formulations described herein comprise rapamycin. In some variations, a rapamycin-containing formulation described herein is stable for a period of time. In some variations, a rapamycin-containing formulation described herein is stable for a period of time, and is prepared by a method described in co-pending U.S. provisional patent application No. 60/772,018, filed Feb. 9, 2006. In some variations, a rapamycin-containing formulation described herein is stable for a period of time, and is preparable by a method described in co-pending U.S. provisional patent application No. 60/772,018, filed Feb. 9, 2006.

Extended Delivery of Therapeutic Agents

For treatment, prevention, inhibition, delaying the onset of, or causing the regression of certain diseases or conditions, it may be desirable to maintain delivery of a therapeutically effective amount of the therapeutic agent for an extended period of time. Depending on the disease or condition being treated, prevented, inhibited, having onset delayed, or being caused to regress this extended period of time may be at least about 1 week, at least about 2 weeks, at least about 3 weeks, at least about 1 month, at least about 3 months, at least about 6 months, at least about 9 months, or at least about 1 year. Generally, however, any extended period of delivery may be possible. A therapeutically effective amount of agent may be delivered for an extended period by a formulation that maintains for the extended period a concentration of agent in a subject or in a tissue of a subject sufficient to deliver a therapeutically effective amount of agent for the extended time.

In some variations a formulation described herein delivers an approximately constant level of the therapeutic agent for one or more of the extended periods of time described herein. "Approximately constant," as used herein, means that the average level does not vary by more than one order of magnitude over the extended period of time, i.e., the difference between the maximum and minimum is less than a 10-fold difference for measurements of the average concentration at times in the relevant period of time.

Delivery of a therapeutically effective amount of the therapeutic agent for an extended period may be achieved via a single placement of a formulation or may be achieved by two or more placements of a formulation. The optimal dosage regime will depend on the therapeutic amount of the therapeutic agent needing to be delivered, and the period over which it need be delivered. Those versed in such extended therapeutic agent delivery dosing will understand how to identify dosing regimes that may be used based on the teachings provided herein.

When using certain therapeutic agents or for the treatment, prevention, inhibition, delaying the onset of, or causing the regression of certain diseases, it may be desirable for delivery of the therapeutic agent not to commence immediately upon placement of the formulation into the subject, but for delivery to commence after some delay. For example, but in no way limiting, such delayed release may be useful where the therapeutic agent inhibits or delays wound healing and delayed release is desirable to allow healing of any wounds occurring upon placement of the formulation. Depending on the therapeutic agent being delivered and/or the diseases and conditions being treated, prevented, inhibited, onset delayed, and regression caused this period of delay before delivery of the therapeutic agent commences may be about 1 hour, about 6 hours, about 12 hours, about 18 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 21 days, about 28 days, about 35 days, or about 42 days. Other delay periods may be possible. Delayed release formulations that may be used are known to people versed in the technology.

In some variations, a formulation as described herein contains an amount of a therapeutic agent equivalent to an amount of rapamycin.

In some variations, any one or more of the formulations described herein are administered systemically every 3 or more months, every 6 or more months, every 9 or more months, or every 12 or more months, or longer, to treat one or more of the diseases or conditions described herein. In some variations, any one or more of the formulations described herein are administered parenterally every 3 or more months, every 6 or more months, every 9 or more months, or every 12 or more months, or longer, to treat one or more of the diseases or conditions described herein.

In some variations, any one or more of the formulations described herein are administered locally every 3 or more months, every 6 or more months, every 9 or more months, or every 12 or more months, or longer, to treat one or more of the diseases or conditions described herein. In some variations, any one or more of the formulations described herein are administered by implantation every 3 or more months, every 6 or more months, every 9 or more months, or every 12 or more months, or longer, to treat one or more of the diseases or conditions described herein.

In some variations, any one or more of the formulations described herein are administered intravitreally every 3 or more months, every 6 or more months, every 9 or more months, or every 12 or more months, or longer, to treat one or more of the diseases or conditions described herein. In some variations, any one or more of the formulations described herein are administered subconjunctivally every 3 or more months, every 6 or more months, every 9 or more months, or every 12 or more months, or longer, to treat one or more of the diseases or conditions described herein.

Dosages of various therapeutic agents for treatment, prevention, inhibition, delay of onset, or cause of regression of various diseases and conditions described herein can be refined by the use of clinical trials.

EXAMPLES

Example 1

Antipermeability Effect of Rapamycin in Hamster Cheek Pouch Model Using VEGF

A hamster cheek pouch model was used to study the antipermeability effect of rapamycin. In this model, a tracer molecule was injected intravenously into a hamster, and various combinations of VEGF (a permeability enhancer in hamster cheek pouch microcirculation), rapamycin (the test compound), and various controls were administered to the hamster to determine their effect on VEGF-induced permeability. The level of tracer was measured by imaging with computer-assisted digital image analysis. A higher integrated optical intensity indicated a higher degree of permeability.

This protocol was modeled directly upon the Materials and Methods section of Aramoto et al., Vascular endothelial growth factor stimulates differential signaling pathways in the in vivo microcirculation, Am J Physiol:Heart Circ Physiol. 287: H1590-H1598, (2004) ("Aramoto 2004."), with the following features.

A total of 42 male golden Syrian hamsters, weighing 80-120 g, were used. The hamsters were anesthetized with sodium pentobarbital (50 mg/kg, ip). Tracheotomy was performed to facilitate breathing; cannulation of left jugular vein was used for administration of flourochrome and additional anesthetic. The left carotid was cannulated for collection of blood and blood pressure monitoring. The right hamster cheek pouch was prepared for direct visualization and intervention using the methods of Mayhan and Joyner, *The Effect Of Altering The External Calcium Concentration And A Calcium Channel Blocker, Verapamil, On Microvascular Leaky Sites And Dextran Clearance In The Hamster Cheek Pouch*, Microvasc. Res. 28(2): 159-79 (1984); see also Aramoto 2004. A removable plastic two piece Lucite chamber with 1 ml reservoir capacity was placed in the cheek pouch to observe and collect suffusate from the microvasculature.

The chamber reservoir was filled with bicarbonate buffer (in millimolar: NaCl 131.9, KCl 4.7, CaCl2 2.0, MgSO4 1.2 NaHCO3 18.0; pH 7.35; buffer bubbled with a 95% N2 and 5% CO2 gas mixture to maintain oxygen tension at approximately 10 mm Hg and pH at 7.4) and tested for leakage.

Vascular leak in the hamsters was observed A Nikon Optiphot or Olympus BH microscope for one hour with suffusate 1 ml/min prior to topical application of VEGF.

Forty-five minutes into the stabilization period the tracer was administered. Fluorescein isothiocyanate-dextran 150 (FITC-Dx 150; MW=150 kDa; Sigma Chemicals Co., St. Louis, Mo.) was used as a tracer for microvascular permeability to macromolecules. It was administered intravenously as a 100 mg/kg bolus and followed by continuous infusion (0.15 mg/kg/min) to maintain a steady plasma concentration throughout the duration of the study. Microvascular transport was assessed by measuring integrated optical intensity (JOT) by computer-assisted digital image analysis. Two or three fields were randomly selected in the cheek pouch and recorded on an Image-1 computer system (Universal Imaging Corporation) before and after the application of the VEGF. Each field included 4-6 postcapillary venules ranging from 15 to 30 µm in diameter; the field was relatively free of capillaries. The maximal IOI was measured at 10, 20, 30, 33, 35, 40, 50, 60, 70, 80 and 90 minutes after topical application of VEGF. The higher the IOI, the higher the permeability.

RAPAMUNE (oral rapamycin suspension) was used for intraperitoneal dosing as follows. The RAPAMUNE oral suspension was formulated as a 1 mg/mL solution, and is made by Wyeth and was obtained from a pharmacy. RAPAMUNE Oral Solution bottles were stored protected from light and refrigerated at 2° C. to 8° C. (36° F. to 46° F.). Once the bottle was opened, the contents were used within one month. After any necessary dilution, the preparation was used immediately.

There were four RAPAMUNE treatment groups corresponding to four doses of RAPAMUNE administered: 10 mg/kg (6 animals), 2 mg/kg (5 animals), 0.5 mg/kg (5 animals), and 0.1 mg/kg (5 animals). Hamsters were weighed and dosed accordingly. For example, a 100 g Hamster in the 2 mg/kg dose group was dosed intraperitoneally with 0.2 cc of the RAPAMUNE suspension. Each treatment group was intraperitoneally administered the appropriate amount of RAPAMUNE at day −1, and again 1 hour prior to start of VEGF topical application.

0.5 mL of the RAPAMUNE vehicle was intraperitoneally administered to each of 3 animals. The RAPAMUNE vehicle is 99% Phosal 50 PG obtained from American Lecithin Co. (Oxford Conn.) (phosphatidylcholine, propylene glycol, mono- and di-glycerides, ethanol, soy fatty acids, and ascorbyl palmitate) and 1% Tween 80 obtained from Sigma-Aldrich (St Louis, Mo.).

As a positive control group, four hamsters were intraperitoneally administered 1 mg/kg caveolin-1 ("Cav-1") scaffold 1 day prior to study of the cheek pouch permeability. Cav-1 is a potent endothelial nitric oxide syntase (eNOS) inhibitor. Bucci et al. have shown that Cav-1 scaffolding domain peptide IP injection attenuated vascular leakage and overall interstitial edema. Nature Medicine 6: 1362-1367 (2000). Bucci et al. also showed that Cav-1 scaffolding domain peptide suppressed carrageenan-induced edema formation and that its anti-inflammatory properties had a similar effect as dexamethasone application. More recently it has also been shown that caveolin-1 impairs microvascular permeability and angiogenesis through the Akt-eNOS pathway. PNAS 102: 204-209 (2005).

The VEGF was a recombinant human VEGF165, obtained from R&D Systems (Minneapolis, Minn.). VEGF was applied topically via a side-port to achieve a $10^{-8}$ M concentration in the hamster cheek pouch chamber, as described further in Aramoto 2004. One dose of VEGF was applied per each animal in each treatment group, except the RAPAMUNE vehicle group received no VEGF. Suffusion was reestablished and effluent collected for 90 minutes. Images were acquired at 10, 20, 30, 33, 35, 40, 50, 60, 70, 80 and 90 minutes after VEGF administration. Images were acquired directly to a computer via either Universal Imaging's Image-1 program or the Universal Imaging's MetaMorph program.

The permeability data is shown in FIG. 1 and Table 1. "R" refers to rapamycin treatment in the figure legend. At 90 minutes, treatment with 0.1 mg/kg was correlated with a greater than 85% reduction in mean permeability relative to the vehicle and VEGF treatment. At 90 minutes, treatment with 0.5 mg/kg was correlated with a greater than 90% reduction in mean permeability relative to the vehicle and VEGF treatment. At 90 minutes, treatment with 2 mg/kg RAPAMUNE and VEGF was correlated with a greater than 30% reduction in mean permeability relative to the vehicle and VEGF treatment. At 90 minutes, treatment with 10 mg/kg RAPAMUNE and VEGF was correlated with greater permeability than treatment with just VEGF.

Thus, the data show that VEGF increased permeability of the microvasculature in the hamster cheek pouch. Rapamycin antagonizes permeability at very low doses. At the 2 mg/kg dose, rapamycin continued to antagonize VEGF-induced permeability, but to a lesser degree than the 0.1 and 0.5 mg/kg doses. At 10 mg/kg of rapamycin, rapamycin's antipermeability effect was inhibited.

Statistical analysis. Because the baseline remained constant throughout the experiment at values ranging from 3 to 5 IOI units, the baseline was subtracted and the transport data are presented as net IOI values. All data are presented as mean±the standard deviation. Statistical analysis was performed using a one-way analysis of variance. When significant values were obtained, the Student-Newman-Keuls test was applied to determine which measurements differed significantly from one another. Differences were considered significant for values of $P<0.05$.

The onset of rapamycin's antipermeability effect was delayed compared to that of Cav-1, and the period of the delay was dependent upon the amount of RAPAMUNE administered.

At later timepoints in the assay rapamycin was a more potent antipermeability agent than Cav-1. Though not bound by theory, it is believed that the later timepoints are particularly relevant in the clinical setting.

TABLE 1

Permeability Study Data

| | A | | B | | C | | D | | E | | F | | G | |
|---|---|---|---|---|---|---|---|---|---|---|---|---|---|---|
| | Vehicle + VEGF (N = 5) | | 2 mg/kg R + VEGF (N = 5) | | 10 mg/kg R + VEGF (N = 6) | | Caveolin 1 mg/kg + VEGF (N = 4) | | 500 µg/kg R + VEGF (N = 5) | | Vehicle only (N = 3) | | 100 µg/kg R + VEGF (N = 5) | |
| Time (min) | Mean | SEM | Mean | SEM | Mean | SEM | Mean | SEM | Mean | SEM | Mean | SEM | Mean | SEM |
| 10 | 0 | 0 | 0 | 0 | 0 | 0 | 0 | 0 | 0 | 0 | 0 | 0 | 0 | 0 |
| 20 | 0 | 0 | 0 | 0 | 0 | 0 | 0 | 0 | 0 | 0 | 0 | 0 | 0 | 0 |
| 30 | 0 | 0 | 0 | 0 | 0 | 0 | 0 | 0 | 0 | 0 | 0 | 0 | 0 | 0 |
| 33 | 5.2 | 3.3 | 2 | 1 | 11 | 4.5 | 0.9 | 0.5 | 0.5 | 0.4 | 0.5 | 0.5 | 2.8 | 2.2 |
| 35 | 6.7 | 3.7 | 1.8 | 1.1 | 11.8 | 3.7 | 2.5 | 1.1 | 1.8 | 1.8 | 0.9 | 0.9 | 4.1 | 2.7 |
| 40 | 9.4 | 5.6 | 5.2 | 3 | 21.6 | 5.5 | 3.4 | 1.8 | 6 | 3.5 | 2.3 | 2.3 | 8.4 | 3.4 |
| 45 | 14.8 | 7.2 | 14.5 | 6.3 | 37.1 | 10 | 3.6 | 1.8 | 14.9 | 9.1 | 3 | 3 | 15.1 | 5.6 |
| 50 | 24.7 | 6.8 | 24 | 8.8 | 43.1 | 11.8 | 5.3 | 2.9 | 15.6 | 9.2 | 3.2 | 3.2 | 17.2 | 7.4 |
| 60 | 37.5 | 5.7 | 34.6 | 7.7 | 62.1 | 15.3 | 6.8 | 3.5 | 9.9 | 6.3 | 3.5 | 3 | 19.3 | 8.4 |
| 70 | 54.6 | 5.2 | 34.6 | 5.1 | 77.2 | 8.4 | 10.9 | 4.4 | 6.1 | 5.4 | 3.4 | 3.4 | 17.9 | 7.8 |
| 80 | 63 | 4.2 | 40.2 | 7.7 | 84.4 | 7.8 | 16.4 | 9 | 3.6 | 2.7 | 3.4 | 3.4 | 9.7 | 5 |
| 90 | 71.3 | 7.7 | 43.5 | 12.4 | 78.6 | 9.1 | 13.3 | 7 | 4 | 1.1 | 3.3 | 3.3 | 8.7 | 4.3 |

Upon sacrifice of the animals, samples of both of the Hamster cheeks were obtained and frozen at −80 degrees Celsius. The samples were labeled as to the amount of intraperitoneal dose received, and whether they were right (studied with chamber) or left. The full tissue sample was homogenized and analyzed for rapamycin levels by LC/MS. Results are provided in Table 2.

TABLE 2

Rapamycin Assayed Concentration in Hamster Check Pouch

| Dosing | Sample ID | Homogenate Conc. (ng/mL) | Homogenate Conc. (ng/g) | Average (ng/g or pg/mg) | SEM (ng/g or pg/mg) |
|---|---|---|---|---|---|
| 0.1 mg/kg | 37 L | 0.510 | 5.10 | 7.37 | 3.09 |
| | 37 R | 1.18 | 11.8 | | |
| | 38 L | 0.248 | 2.48 | | |
| | 38 R | 0.714 | 7.14 | | |
| | 39 L | 0.741 | 7.41 | | |
| | 39 R | 1.15 | 11.5 | | |
| | 40 L | 0.418 | 4.18 | | |
| | 40 R | 0.919 | 9.19 | | |
| | 41 L | 0.561 | 5.61 | | |
| | 41 R | 0.926 | 9.26 | | |
| 0.5 mg/kg | 1 L | 1.07 | 10.7 | 11.01 | 10.72 |
| | 1 R | 1.31 | 13.1 | | |
| | 2 L | 1.45 | 14.5 | | |
| | 2 R | 3.46 | 34.6 | | |
| | 3 L | 0.0784 | 0.784 | | |
| | 3 R | 0.0805 | 0.805 | | |
| | 4 L | 0.0743 | 0.743 | | |
| | 4 R | 0.272 | 2.72 | | |
| | 5 L | 1.24 | 12.4 | | |
| | 5 R | 1.97 | 19.7 | | |
| 2 mg/kg | 18 R | 4.34 | 43.4 | 40.83 | 23.85 |
| | 19 L | 2.00 | 20.0 | | |
| | 19 R | 5.69 | 56.9 | | |
| | 21 L | 4.65 | 46.5 | | |
| | 21 R | 6.91 | 69.1 | | |
| | 23 L | 3.09 | 30.9 | | |
| | 23 R | 7.65 | 76.5 | | |
| | 24 L | 1.25 | 12.5 | | |
| | 24 R | 1.17 | 11.7 | | |
| 10 mg/kg | 13 L | 4.33 | 43.3 | 55.15 | 12.86 |
| | 13 R | 5.76 | 57.6 | | |
| | 14 L | 3.95 | 39.5 | | |
| | 14 R | 4.79 | 47.9 | | |
| | 15 L | 3.93 | 39.3 | | |
| | 15 R | 5.86 | 58.6 | | |
| | 25 L | 8.12 | 81.2 | | |
| | 25 R | 7.27 | 72.7 | | |
| | 26 L | 5.00 | 50.0 | | |
| | 26 R | 5.11 | 51.1 | | |
| | 27 L | 5.64 | 56.4 | | |
| | 27 R | 6.42 | 64.2 | | |
| Vehicle | 6 L | BQL | BQL | 1.28 | 0.74 |
| | 6 R | BQL | BQL | | |
| | 35 L | 0.203 | 2.03 | | |
| | 35 R | 0.0559 | 0.559 | | |
| | 36 L | BQL | BQL | | |
| | 36 R | 0.124 | 1.24 | | |

BQL = below quantitation limit (0.03 ng/mL). A dilution factor of 10 was applied to report this data in ng/g units.

The 0.1 mg/kg treatment group was correlated with an average tissue level of 7.37 ng/g of rapamycin in the hamster cheek pouch. The 0.5 mg/kg treatment group was correlated with an average tissue level of 11.01 ng/g of rapamycin in the hamster cheek pouch. The 2.0 mg/kg treatment group was correlated with an average tissue level of 40.83 ng/g of rapamycin in the hamster cheek pouch. The 10 mg/kg treatment group was correlated with an average tissue level of 55.15 ng/g of rapamycin in the hamster cheek pouch. The vehicle control treatment group was correlated with an average tissue level of 1.28 ng/g of rapamycin in the hamster cheek pouch. Thus, increased dosing was correlated with higher tissue levels of rapamycin in the hamster cheek pouch. Additionally, the vehicle control revealed some background in the rapamycin concentration assay.

Example 2

Antipermeability Effect of Rapamycin in Hamster Cheek Pouch Model Using PAF

The antipermeability effect of rapamycin in response to platelet-activating factor (PAF) was analyzed. The protocol of Example 1, using PAF (1-o-alkyl-2-acetyl-sn-3-glycero-phosphoryl-choline; Sigma Chemical Co., St. Louis, Mo.) in the place of VEGF, was performed, except PAF was applied topically via a side-port to achieve a $10^{-7}$ M concentration in the hamster cheek pouch chamber. A 0.5 mg/kg dose of RAPAMUNE was intraperitoneally administered at day −1, and again 1 hour prior to start of PAF topical application. A vehicle-only negative control and a vehicle+PAF positive control were also used. There were 3 animals per treatment group.

Figure 2:
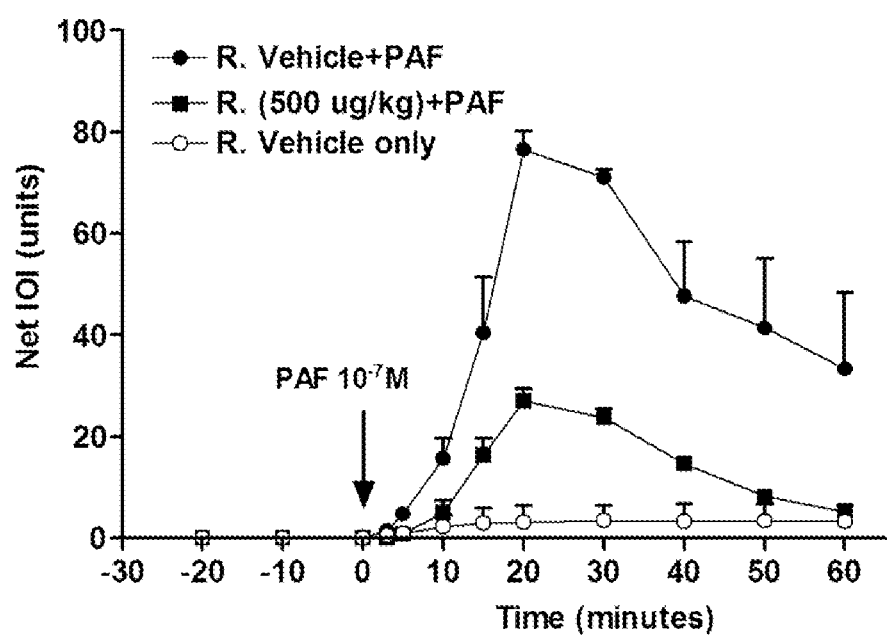
FIG. 2 depicts the vascular antipermeability effects of rapamycin in response to PAF and various control treatments in a hamster cheek pouch model. This figure shows the time course of integrated optical intensity (IOI) of fluorescein isothiocyanate-Dextran 70 (FITC-Dx 70). After baseline measurements, $10^{-7}$ M PAF was applied at the time indicated by the arrow. Rapamycin (R.) or R. vehicle was applied intraperitoneally at 24 hours and again 1 hour before PAF application. Data are mean±SEM.

The permeability data are shown in FIG. 2. "R" refers to rapamycin treatment in the figure legend. The PAF treatment was correlated with a significantly higher level of permeability than the vehicle control. Treatment with 0.5 mg/kg rapamycin plus PAF was correlated with reduced permeability relative to the PAF treatment alone. At 20 minutes, for example, treatment with 0.5 mg/kg was correlated with a 65% reduction in mean permeability relative to the vehicle plus PAF treatment. Rapamycin plus PAF treatment resulted in reduced permeability relative to PAF-treated animals throughout the experiment.

VEGF is a permeability-altering agent associated with vasodilation, whereas PAF is a permeability-altering agent associated with vasoconstriction. Results with PAF confirm the anti-permeability results of rapamycin which were observed with VEGF.

Example 3

Arteriolar Diameter Effect of Rapamycin

Arteriolar diameter was measured as the width of epi-illuminated blood column using a MetaMorph image system. Two or three arterioles with diameter of 20-30 μm were studied per animal. Baseline diameter measurements were normalized to a value of one. For each vessel, the experimental diameter was expressed as a ratio of baseline diameter (relative luminal diameter). To compare diameter before and after an agonist application, diameters were measured at the same place in the arterioles of interest.

Figure 3:
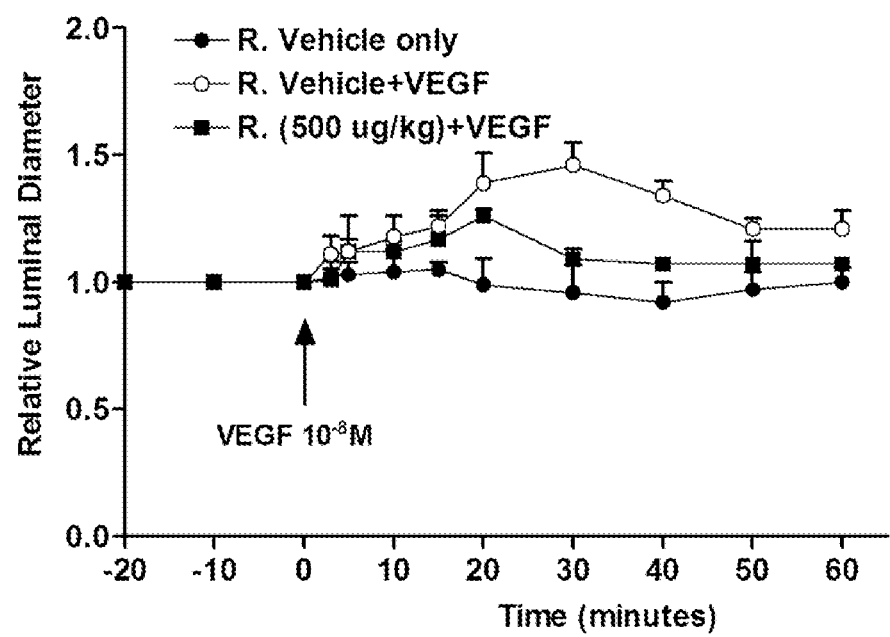
FIG. 3 depicts the arterial vasodilation effects of rapamycin in a hamster cheek pouch model. This figure shows the time course of relative luminal diameter. After baseline measurements, $10^{-8}$ VEGF was applied at the time indicated by the arrow. Rapamycin (R.) or R. vehicle was applied intraperitoneally at 24 hours and again 1 hour before VEGF application. Data are mean±SEM.
Figure 4:
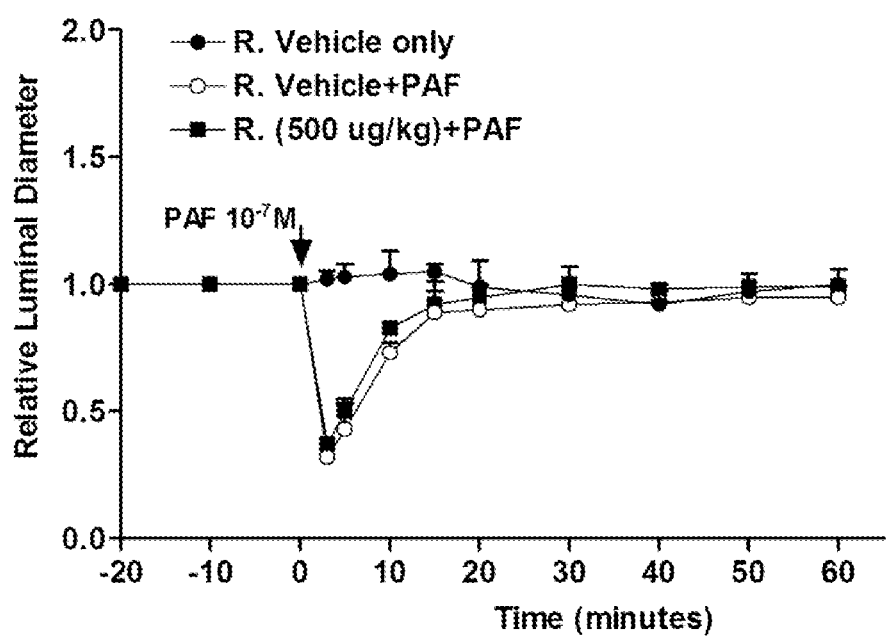
FIG. 4 depicts the arterial vasodilation effects of rapamycin in a hamster cheek pouch model. This figure shows the time course of relative luminal diameter. After baseline measurements, $10^{-7}$ PAF was applied at the time indicated by the arrow. Rapamycin (R.) or R. vehicle was applied intraperitoneally at 24 hours and again 1 hour before PAF application. Data are mean±SEM.

The arterial vasodilation data is shown in FIG. 3 and FIG. 4. In FIG. 3, there were 3 animals per treatment group. "R vehicle" refers to the rapamycin vehicle, as indicated in the figure legend. VEGF treatment resulting in a significantly increased relative luminal diameter as compared to the vehicle treatment. Pretreatment with rapamycin vehicle did not cause any significant change of arteriolar diameter. Topical application of $10^{-8}$ M VEGF for 3 minutes produced strong vasodilation. The ratio of experimental to baseline arteriolar diameter gradually increased and achieved its peak at 30 min after application of VEGF; the arteriolar diameter ratio increased from 1.0 to 1.46±0.09 (P<0.05). After the peak, the arteriolar diameter ratio gradually decreased and reached ~80% of baseline value at 50 min after application of VEGF. At 30-min after VEGF application, 500 μg/kg rapamycin attenuated the increase in relative luminal diameter induced by VEGF 10-8 M from 1.46±0.09 to 1.09±0.04 (P=0.02; FIG. 3).

FIG. 4 shows the effect of 500 μg/kg rapamycin on PAF-stimulated vasoconstriction. In FIG. 4, there were 3 animals per treatment group. The baseline values of arteriolar diameter did not change significantly in a 30-min period. PAF applied topically for 3 min at $10^{-7}$ M produced strong vasoconstriction. The ratio of experimental to baseline arteriolar diameter fell from 1.0 to 0.32±0.02 within 5 min after the topical application of PAF. On removal of PAF and reinstitution of suffusate flow, the arteriolar diameter ratio gradually increased and achieved ~90% of baseline value within 15 min. Pretreatment with 500 μg/kg rapamycin did not attenuate the vasoconstrictor action of PAF.

All references cited herein, including patents, patent applications, and publications, are hereby incorporated by reference in their entireties, whether previously specifically incorporated or not.

We claim:

1. A method to decrease vascular permeability in a subject with diabetic macular edema, comprising administering a therapeutic agent to the subject at a dose of no greater than an amount equivalent to 2 mg/kg of rapamycin, wherein the therapeutic agent is rapamycin, or a pharmaceutically acceptable salt thereof.

2. The method of claim 1, wherein the subject is a human subject.

3. The method of claim 1, wherein the therapeutic agent is rapamycin.

4. The method of claim 1, wherein the therapeutic agent is administered to the subject in need thereof at a dose of no greater than an amount equivalent to 0.5 mg/kg of rapamycin.

5. The method of claim 1, wherein the therapeutic agent is administered to the subject in need thereof at a dose of no greater than an amount equivalent to 0.27 mg/kg of rapamycin.

6. The method of claim 1, wherein the therapeutic agent is administered to the subject in need thereof at a dose of no greater than an amount equivalent to 0.07 mg/kg of rapamycin.

7. The method of claim 1, wherein the therapeutic agent is administered to the subject in need thereof at a dose of no greater than an amount equivalent to 0.014 mg/kg of rapamycin.

8. The method of claim 1, wherein the therapeutic agent is rapamycin, and the rapamycin is administered in a formulation containing about 2% w/w rapamycin, about 4% w/w ethanol, and about 94% w/w PEG 400.

* * * * *